US006770478B2

(12) United States Patent
Crowe et al.

(10) Patent No.: US 6,770,478 B2
(45) Date of Patent: Aug. 3, 2004

(54) ERYTHROCYTIC CELLS AND METHOD FOR PRESERVING CELLS

(75) Inventors: John H. Crowe, Davis, CA (US); Lois M. Crowe, Davis, CA (US); Fern Tablin, Davis, CA (US); Willem F Wolkers, Davis, CA (US); Nelly M. Tsvetkova, Davis, CA (US); Ann F. Oliver, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/052,162

(22) Filed: Jan. 16, 2002

(65) Prior Publication Data

US 2002/0114791 A1 Aug. 22, 2002

Related U.S. Application Data

(63) Continuation-in-part of application No. 09/927,760, filed on Aug. 9, 2001, and a continuation-in-part of application No. 09/828,627, filed on Apr. 5, 2001, and a continuation of application No. 09/501,773, filed on Feb. 10, 2000, now abandoned.

(51) Int. Cl.[7] ............................ C12N 5/00; C12N 5/08; C12P 19/12; A01N 1/02
(52) U.S. Cl. ........................ 435/374; 435/2; 435/100; 435/325; 435/372
(58) Field of Search ............................ 435/2, 100, 325, 435/372, 374

(56) References Cited

U.S. PATENT DOCUMENTS

| | | |
|---|---|---|
| 3,932,943 A | 1/1976 | Briggs et al. |
| 4,145,185 A | 3/1979 | Brinkhous et al. |
| 4,251,995 A | 2/1981 | Pert et al. |
| 4,287,087 A | 9/1981 | Brinkhous et al. |
| 4,302,355 A | 11/1981 | Turner, Jr. et al. |
| 4,585,735 A | 4/1986 | Meryman et al. |
| 4,695,460 A | 9/1987 | Holme |
| 4,717,654 A | 1/1988 | Savoca et al. |
| 4,874,690 A | 10/1989 | Goodrich, Jr. et al. |
| 4,880,788 A | 11/1989 | Moake et al. |
| 4,891,319 A | 1/1990 | Roser |
| 4,994,367 A | 2/1991 | Bode et al. |
| 5,026,566 A | 6/1991 | Roser |
| 5,030,560 A | 7/1991 | Sinor et al. |
| 5,043,261 A | 8/1991 | Goodrich et al. |
| 5,045,446 A | 9/1991 | Goodrich, Jr. et al. |
| 5,059,518 A | 10/1991 | Kortright et al. |
| 5,149,653 A | 9/1992 | Roser |
| 5,151,360 A | 9/1992 | Handa et al. |
| 5,153,004 A | 10/1992 | Goodrich, Jr. et al. |
| 5,165,938 A | 11/1992 | Knighton |
| 5,171,661 A | 12/1992 | Goodrich, Jr. et al. |
| 5,178,884 A | 1/1993 | Goodrich et al. |
| 5,213,814 A | 5/1993 | Goodrich, Jr. et al. |
| 5,236,716 A | 8/1993 | Carmen et al. |
| 5,242,792 A | 9/1993 | Rudolph et al. |
| 5,248,506 A | 9/1993 | Holme et al. |
| 5,250,303 A | 10/1993 | Meryman et al. |
| 5,328,840 A | 7/1994 | Coller |
| 5,332,578 A | 7/1994 | Chao |
| 5,344,752 A | 9/1994 | Murphy |
| 5,358,844 A | 10/1994 | Stossel et al. |
| 5,376,524 A | 12/1994 | Murphy et al. |
| 5,378,601 A | 1/1995 | Gepner-Puszkin |
| 5,428,008 A | 6/1995 | Chao et al. |
| 5,510,263 A | 4/1996 | Quaranta et al. |
| 5,827,741 A | 10/1998 | Beattie et al. |
| 5,902,608 A | 5/1999 | Read et al. |
| 5,958,670 A | 9/1999 | Goodrich, Jr. et al. |

FOREIGN PATENT DOCUMENTS

| | | |
|---|---|---|
| EP | 0356257 A2 | 2/1990 |
| EP | 0356257 B1 | 3/1995 |
| EP | 0668013 A2 | 8/1995 |
| WO | WO 86/03938 | 7/1986 |
| WO | WO 87/05300 | 9/1987 |
| WO | WO 90/04329 | 5/1990 |
| WO | WO 93/00806 | 1/1993 |
| WO | WO 93/14191 | 7/1993 |

OTHER PUBLICATIONS

E.A.J. Bateson et al., "Electrokinetic Properties of Human Cryopreserved Platelets", proceeds from Clinical Chemistry Department, Guy's Hospital, London; Department of Cell Biology and Biochemistry, Hunterian Institute, Royal College of Surgeons, pp. 213–219, 1994.

Kenneth Hughes and Neville Crawford, "Reversibly Electropermeabilized Platelets: Potential Use as Vehicles for Drug Delivery", Department of Biochemistry, Hunterian Institute, Royal College of Surgeons of England, Biochemical Society Transactions, pp. 871–873, Mar. 1990.

A.A. Rayos et al., "Quick Freezing of Unfertilized Mouse Oocytes Using Ethylene Glycol with Sucros or Trehalose", Department of Theriogenology, Faculty of Veterinary Medicine, Hokkaido University, Japan, Journal of Reproduction and Fertility, pp. 123–129, Mar. 1993.

(List continued on next page.)

Primary Examiner—Shin-Lin Chen
(74) Attorney, Agent, or Firm—John W. Carpenter; Carpenter & Kulas LLP

(57) ABSTRACT

A dehydrated composition is provided that includes freeze-dried erythrocytic cells. Alcohol (e.g., sterol or cholesterol) is at least partially removed from erythrocytic cells including erythrocytic membranes. After removal of at least part of the alcohol, the erythrocytic cells have a low phase transition temperature range, an intermediate phase transition temperature range, and a high phase transition temperature range. The erythrocytic cells may be loaded with an oligosaccharide (e.g., trehalose) which preserves biological properties during freeze-drying and rehydration. A process for increasing cooperativity of a phase transition of an erythrocytic cell. A process for preserving and/or increasing the survival of dehydrated erythrocytic cells, including storing dehydrated erythrocytic cells having a residual water content equal to or less than about 0.30 gram of water per gram of dry weight erythrocytic cells.

15 Claims, 35 Drawing Sheets

OTHER PUBLICATIONS

Ali, A.M. et al., "Platelet Concentrates Stored for 5 Days in a Reduced Volume of Plasma Maintain Hemostatic Function and Viability", The Canadian Red Cross Society and the Departments of Pathology, Medicine and Clinical Epidemiology and Biostatistics, McMaster University Faculty of Health Science, Hamilton, Ontario Canada, vol. 34, No. 1, 1994.

Allain, J.P. et al., "Platelets Fixed with Paraformaldehyde: A New Reagent for Assay of Vo Willebrand Factor and Platelet Aggregating Factor", Department of Pathology, University of North Carolina, J. Lab: Clin. Med., vol. 85, No. 2, pp. 318–328, Feb. 1975.

Argall, Mary E. and Smith, Geoffrey D., "The Use of Trehalose–Stabilized Lyophilized Methanol Dehydrogenase from Hyphomicrobium X for the Detection of Methanol", Division of Biochemistry and Molecular Biology, School of Life Sciences, Faculty of Science, The Australian National University, Canberra, Australia, vol. 30, No.3, Jul. 1993.

Bando, Toru, et al., "Effects of Newly Developed Solutions Containing Trehalose on Twenty–hour Canine Lung Preservation", Department of Thoracic Surgery, Chest Disease Research Institute, Kyoto University, Kyoto, Japan, vol. 108, No. 1, pp. 92–98, Jul. 1994.

Bando, T. et al., "Twenty–Hour Canine Lung Preservation Using Newly Developed Solutions Containing Trehalose", Transplantation Proceedings, vol. 26, No. 2, pp. 871–872, Apr. 1994.

Blajchman, Morris A. et al., "The Contribution of the Haematocrit to Thrombocytopenic Bleeding in Experimental Animals", Departments of Pathology and Medicine, McMaster university and the Canadian Red Cross Society, Ontario, Canada, British Journal of Haematology 86, pp. 347–350, 1994.

Blakeley, Diane et al., "Dry Instant Blood Typing Plate for Bedside Use", The Lancet 336, pp. 854–855, 1990.

Bock, M. et al., "Cryopreservation of Human Platelets with Dimethyl Sulfoxide: Changes in Biochemistry and Cell Function", Department of Transfusion Medicine, University of Magdeburg, Magdeburg, Germany and the Transfusion Center, Klinikum Grosshadern, University of Munich, Transfusion 35, pp. 921–924, 1995.

Bode, Arthur P. et al., "Sustained Elevation of Intracellular Cyclic 3'–5' Adenosine Monophosphate is Necessary for Preservation of Platelet Integrity During Long–Term Storage at 22° C.", Departments of Pathology and Laboratory Medicine and Surgery, East Carolina University School of Medicine, vol. 83, No. 5, pp. 1235–1243, Mar. 1994.

Bode, Arthur P. and Miller, David T. "The Use of Thrombin Inhibitors and Aprotinin in the Preservation of Platelets Stored for Transfusion", Department of Clinical Pathology and Diagnostic Medicine, East Carolina University School of Medicine, pp. 753–758, Jun. 1989.

Colaco, Camilo et al., "Extraordinary Stability of Enzymes Dried in Trehalose: Simplified Molecular Biology", Quadrance Research Foundation, Biotechnology vol. 10, pp. 1007–1011, Sep. 1992.

Colaco, C. et al., "Trehalose Stabilisation of Biological Molecules", Quadrant Research Foundation, Biotechnology International, pp. 345–350.

Carpenter, John F. et al., "Cryoprotection of Phosphofructokinase with Organic Solutes: Characterization of Enhanced Protection in the Presence of Divalent Cations", Department of Zoology, University of California, Davis, Archives of Biochemistry and Biophysics, vol. 250, No. 2, pp. 505–512, Nov. 1986.

Chao, F.C., et al., "Infusible Platelet Membrane Microvesicles: A Potential Transfusion Substitute for Platelets", Transfusion, vol. 36 No. 6, pp. 536–542, 1996.

Colvin, B.T., et al., "Effect of Dry Heating of Coagulation Factor Concentrates at 80° C. for 72 Hours on Transmission of Non–A, Non–B Hepatitis" The Lancet, pp. 814–816, Oct., 1988.

Crook, M. and Crawford, N., "Platelet Surface Charge Hetergology: Characterization of Human Platelet Subpopulations Separated by High Voltage Continuous Flow Electrophoresis", British Journal of Haematology 69, pp. 265–273, 1988.

Crowe, John H. et al., "Are Freezing and Dehydration Similar Stress Vectors? A Comparison of Modes of Interaction of Stabilizing Solutes with Biomolecules", Symposium on Cryosensitizing and Cryoprotective Agents at the $26^{th}$ Annual Meeting of the Society for Cryobiology, 27, pp. 219–231, 1990.

Crowe, John H. et al., Cryoprotection of Phosphofructokinase with Organic Solutes: Characterization of Enhanced Protection in the Presence of Divalent Cations:, Department of Zoology, University of California, Davis, Archives of Biochemistry and Biophysics, vol. 250, No. 2, pp. 505–512, Nov. 1986.

Crowe, John W. et al., "Is Vitrification Involed in Depression of the Phase Transition Temperature in Dry Phospholipids?", Biochimica et Biophysica Acta (BBA) 1280, pp. 187–196, 1996.

Crowe, John H. and Crowe, Lois M., "Preservation of Liposomes by Freeze–Drying" Liposome Technology, vol. 1, Chapter 14, pp. 229–252, 1993.

Crowe, John H. et al., "Preservation of Membranes in Anhydrobiotic Organisms: The Role of Trehalose", American Association for the Advancement of Science, vol. 223, pp. 701–703, Feb., 1984.

Crowe, John H. et al., "Preservation of Structural and Functional Activity in Lyophilized Sarcoplasmic Reticulum", Archives of Biochemistry and Biophysics, vol. 220, No. 2, pp. 477–484, Feb. 1983.

Crowe, Lois M. et al., "Effects of Carbohydrates on Membrane Stability at Low Water Activities", Department of Zoology, University of California, Davis, Biochemica et Biophysica Acta, 769, pp. 141–150, 1984.

Crowe, Lois M. et al., "Preservation of Freeze–Dried Liposomes by Trehalose", Department of Zoology, University of California, Davis, Archives of Biochemistry and Biophysics, vol. 242, No. 1, pp. 240–247, Oct. 1985.

Dale, George L. et al, "High–Efficiency Entrapment of Enzymes in Resealed Red Cell Ghosts by Dialysis", Academic Press, Inc., Methods in Enzymology, vol. 149, pp. 229–234, 1987.

Eleutherio, Elis C.A., "Role of the Trehalose Carrier in Dehydration Resistance of *Saccharomyces cerevisiae*", Biochimica et Biophysica Acta, 1156, pp. 263–266, 1993.

Foote, R.H. et al., "Fertility of Bull Spermatozoa Frozen in Whole Milk Extender with Trehalose, Taurine, or Blood Serum", Department of Animal Science Cornell University and Eastern Artificial Insemination Cooperative, Inc., Ithaca, New York, Journal of Dairy Science, vol. 76, No. 7, 1993.

Gerencser, George A., "Cryoprotection of Aplysia Gut Basolateral Membrances by Trehalose", Department of Physiology, College of Medicine, University of Florida, Comp. Biochem. Physiol. vol. 108A, No. 1, pp. 53–57, 1994.

Goodrich, Raymond P. et al., "Preservation of Metabolic Activity in Lyophilized Human Erythrocytes", Proc. Natl. Acad. Sci. vol. 89, pp. 967–971, Feb., 1992.

Hirata, T. et al., "Effects of Trehalose in Canine Lung Preservation", Department of Thoracic Surgery, Chest Disease Research Institute, Kyoto University, Kyoto, Japan, vol. 115, No. 1, pp. 102–107, Jan. 1994.

Hirata, T. et al., "Effects of Trehalose in Preservation of Canine Lung for Transplants", Department of Thoracic Surgery, Chest Disease Research Institute, Kyoto University, Kyoto, Japan, Thorac. Cardiovasc. Surgeon 41, pp. 59–63, 1993.

Hirata, T. et al., "Successful 12–Hour Lung Preservation with Trehalose", Transplantation Proceedings, vol. 25, No. 1, pp. 1597–1598, Feb. 1993.

Holme, S. et al., "Evaluation of Platelet Concentrates Stored for 5 days with Reduced Plasma Volume", American Red Cross, Mid–Atlantic Region and Eastern Virginia Medical School, Transfusion, vol. 34, No. 1, pp. 39–43, 1994.

Holme, S. et al., "Improved Maintenance of Platelet in vivo Viability During Storage When Using a Synthetic Medium with Inhibitors", American Red Cross, East Carolina University School of Medicine, vol. 119, No. 2, pp. 144–150, Feb. 1992.

Hottiger, Thomas et al., "The Role of Trehalose Synthesis for the Acquisition of Thermotolerance in Yeast II. Physiological Concentrations of Trehalose Increase the Thermal Stability of Protein In Vitro", Eur. J. Biochem. 219, pp. 187–193, 1994.

Hughes, K. and Crawford, N., "Reversible Electropermeabilisation of Human and Rat Blood Platelets: Evaluation of Morphological and Functional Integrity 'In Vitro' and 'In Vivo'", Department of Biochemistry and Cell Biology, Hunterian Institute, Royal College of Surgeon of England, Biochimica et Biophysica Acta, 981, pp. 277–287, 1989.

Ihler, Garret M. and Tsang, Hannah Chi–Wan, "Hypotonic Hemolysis Methods for Entrapment of Agents in Resealed Erythrocytes", Methods of Enzymology, vol. 149, pp. 221–229, 1987.

Jindal, Rahul and Gray, Derek, "Preservation and Storage of Pancreatic Islets", Division of Transplantation, Mt. Sinai School of Medicine, New York and University of Oxford, United Kingdom, vol. 57, pp. 317–321, No. 3, Feb. 1994.

Leslie, Samuel B. et al., "Trehalose and Sucrose Protect Both Membranes and proteins in Intact Bacteria during Drying", Section of Molecular and Cellular Biology, University of California, Davis, Applied and Environmental Microbiolgoy, pp. 3592–3597, Oct., 1995.

Lionetti, F.J. et al., "Improved Method for the Cryopreservation of Human Red Cells in Liquid Nitrogen with Hydroxythyl Starch", Center for Blood Research and Tufts University School of Medicine, Boston, MA, Cryobiology13, pp. 489–499, 1976.

Magnani, Mauro et al., "Targeting Antiretroviral Nucleoside Analogues in Phosphorylated Form to Macrophages: In Vitro and In Vivo Studies", Proc. Natl. Acad. Sci., vol. 89, pp. 6477–6481, Jul. 1992.

Moroff, G. et al., "Effect on Platelet Properties of Exposure to Temperatures Below 20° C. for Short Periods During Storage at 20 to 24° C.", American Red Cross, Jerome H. Holland Laboratory for the Biomedical Sciences, and Red Cross Blood Services, Transfusion, vol. 34, No. 4, pp. 317–321, 1994.

Okada, Craig Y. and Rechsteiner, Martin, "Introduction of Macromolecules into Cultured Mammallan Cells by Osmotic Lysis of Pinocytic Vesicles", Department of Biology, University of Utah, vol. 29, pp. 33–41, May 1982.

Puisieux, Francis et al., "Liposomes, New Systems and New Trends in their Applications", Published in France by Editions de Sante, Chapter 8, pp. 239–272, 1995.

Read, Marjorie S. et al., "Preservation of Hemostatic and Structural Properties of Rehydrated Lyophilized Platelets: Potential for Long–Term Storage of Dried Platelets for Transfusion", Proc. Natl. Acad. Sci, vol. 92, pp. 397–401, Jan. 1995.

Rechsteiner, Martin, "Osmotic Lysis of Pinosomes", Methods in Enzymology, vol. 149, pp. 42–48, 1987.

Roser, Bruce and Colaco, Camilo, "A Sweeter Way to Fresher Food", New Scientist, May 1993.

Roser, Bruce, "Trehalose, a New Approach to Premium Dried Foods", Trends in Food Science & Technology, Jul. 1991.

Rudolph, Alan S. and Crowe, John H., "A Calorimetric and Infrared Spectroscopic Study of the Stabilizing Solute Proline", Biophysical Society, vol. 50, pp. 423–430, Sep. 1986.

Shier, W. Thomas, "Studies on the Mechanisms of Mammalian Cell Killing by a Freeze–Thaw Cycle: Conditions that prevent Cell Killing Using Nucleated Freezing", Department of Medicinal Chemistry and Pharmacognosy, College of Pharmacy, University of Minnesota, Cryobiology 25, pp. 110–120 (1988).

Tablin, Fern et al., "Membrane Phase Transition of Intact Human Platelets: Correlation with Cold–Induced Activation", Departments of Anatomy, Physiology, and Cell Biology and Molecular and Cellular Biology, University of California, Davis, Journal of Cellular Physiology 168, pp. 305–313, 1996.

Terasaki, Mark et al., "Localization of endoplasmic Reticulum in Living and Glutaraldehyde–Fixed Cells with Fluorescent Dyes", Dana–Farber Cancer Institute and Department of Pathology Harvard Medical School, Cell, vol. 38, pp. 101–108, Aug. 1984.

Yokomise, H. et al., "Reliable Cryopreservation of Trachea for One Month in a New Trehalose Solution", Division of Thoracic Surgery, Chest Disease Research Institute, Kyoto University, Kyoto; Japan, vol. 110, No. 2, pp. 382–385, 1995.

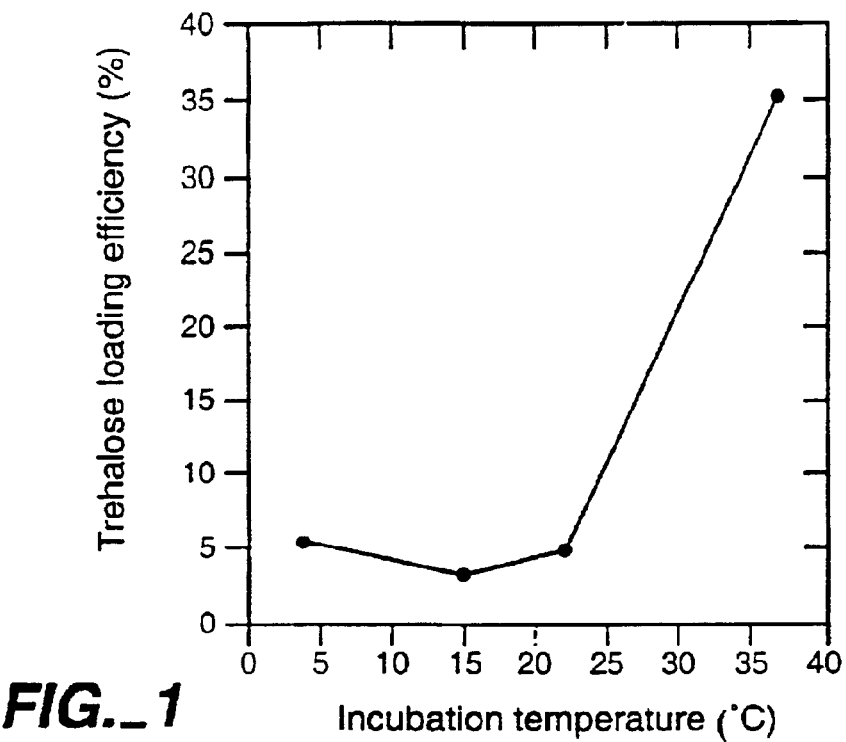
FIG._1
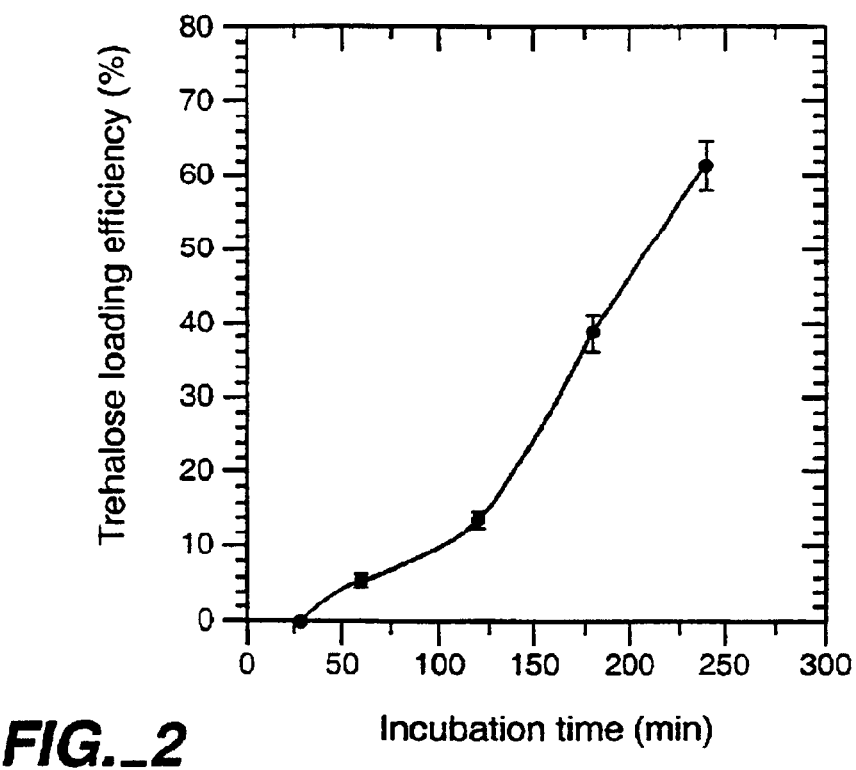
FIG._2

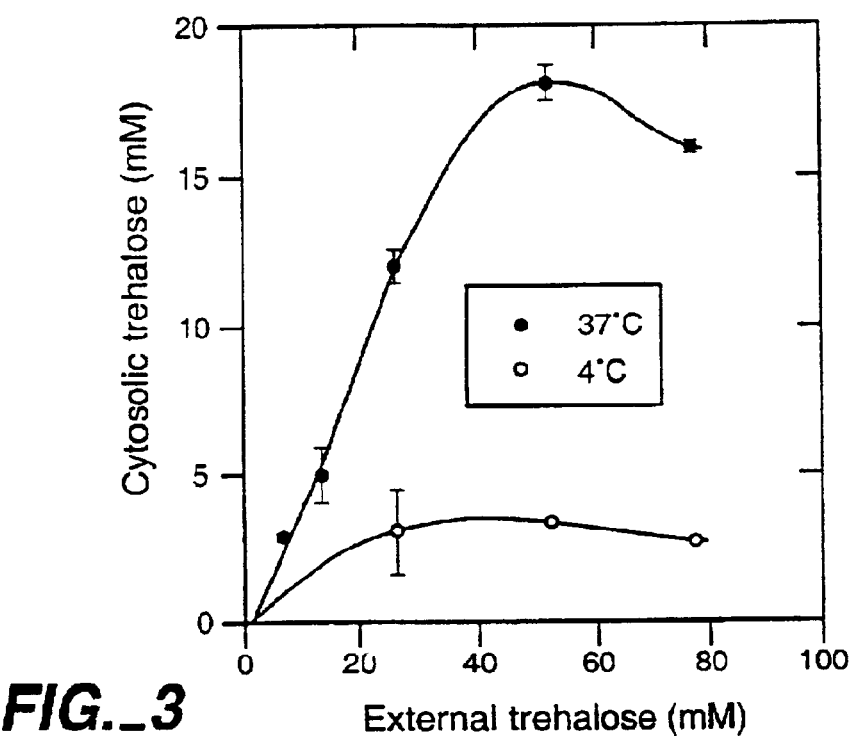
FIG._3
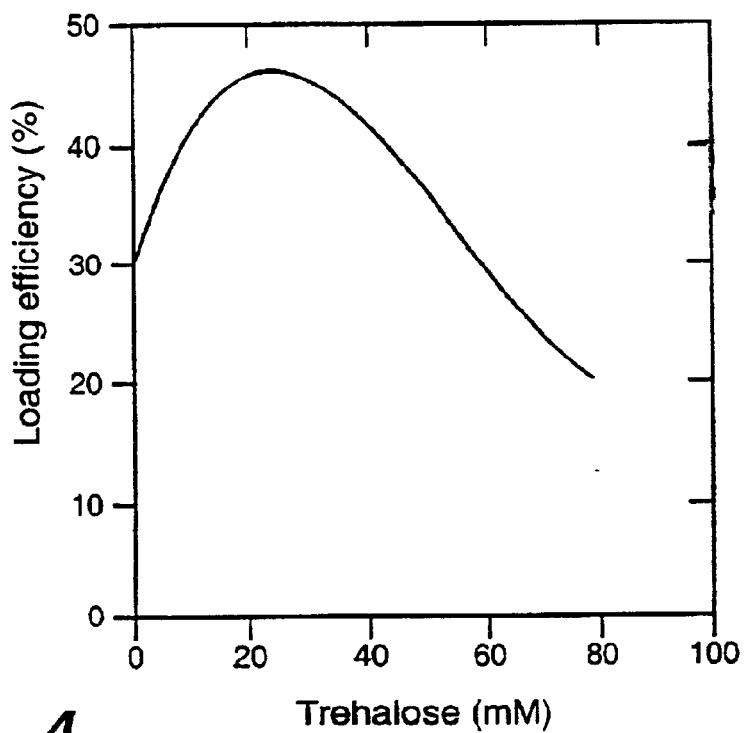
FIG._4

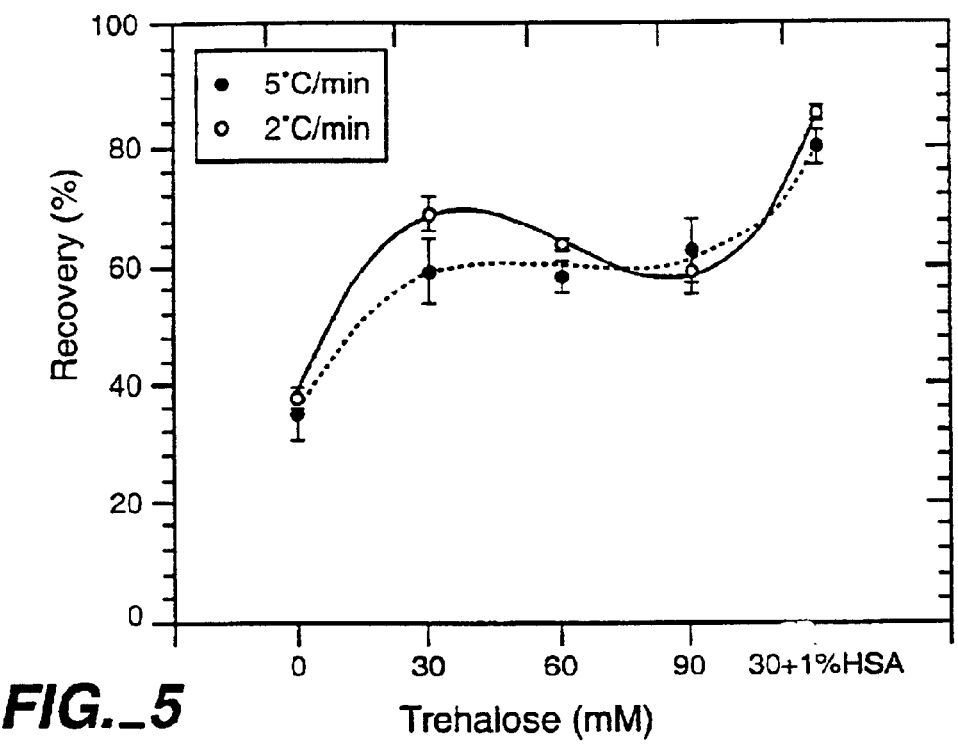
FIG._5
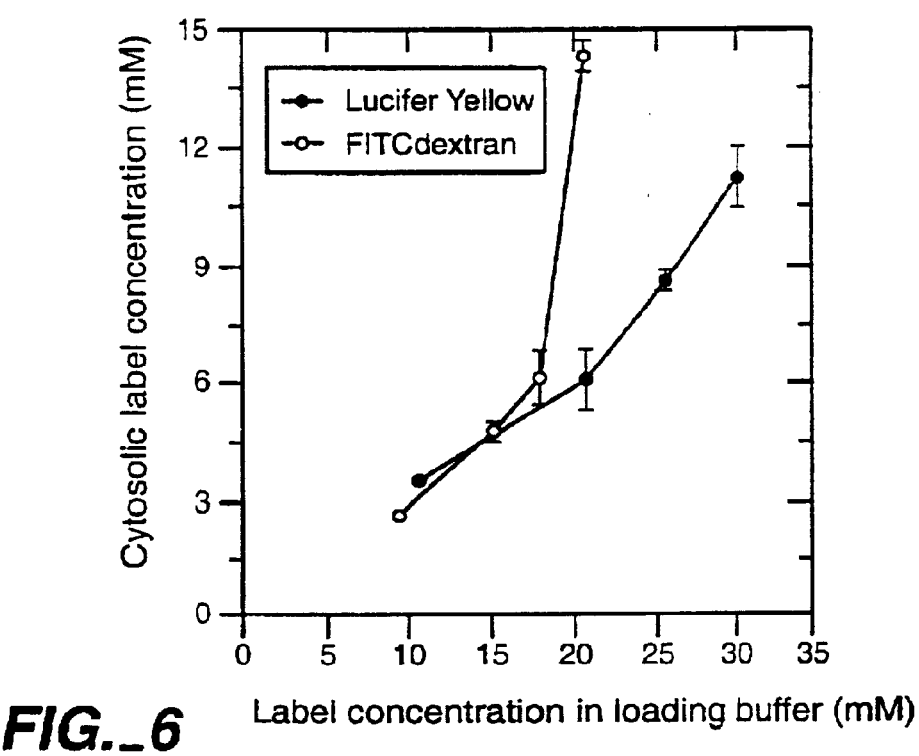
FIG._6

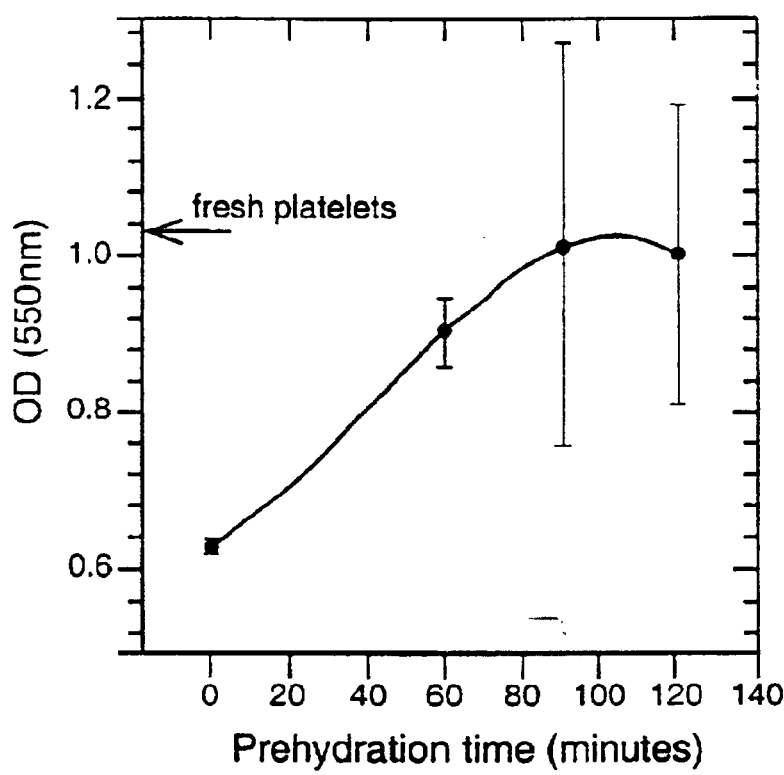
FIG._7
FIG._8A
*(PRIOR ART)*
FIG._8B

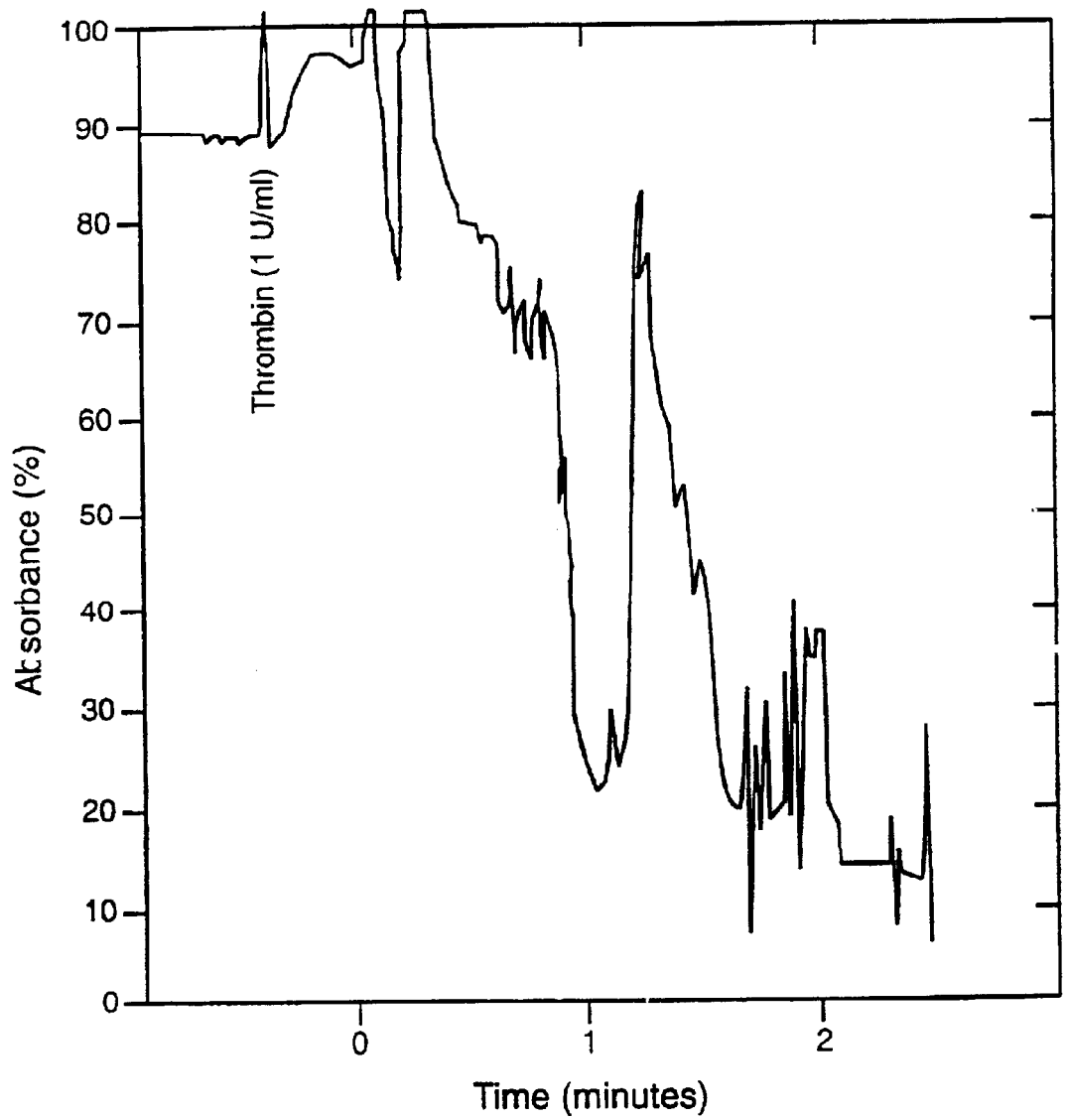
FIG._9

E. Control

D. 3.5 hours

C. 2 hours

B. 1 hour

A. 30 min

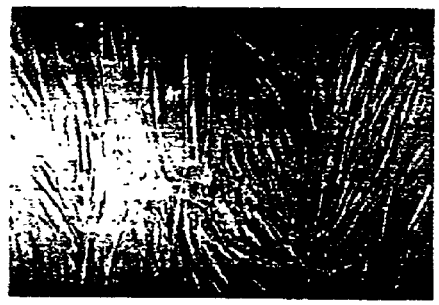 
Fig. 14A　　　　　　　　Fig. 14B
 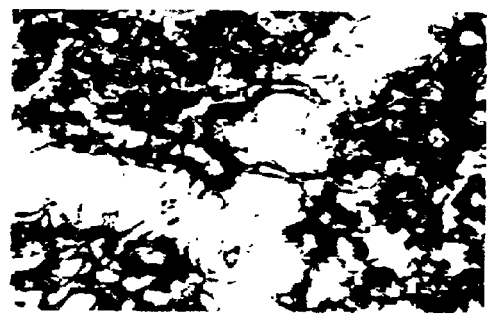
Fig. 15A　　　　　　　　Fig. 15B

 
Fig. 17A
Fig. 17B

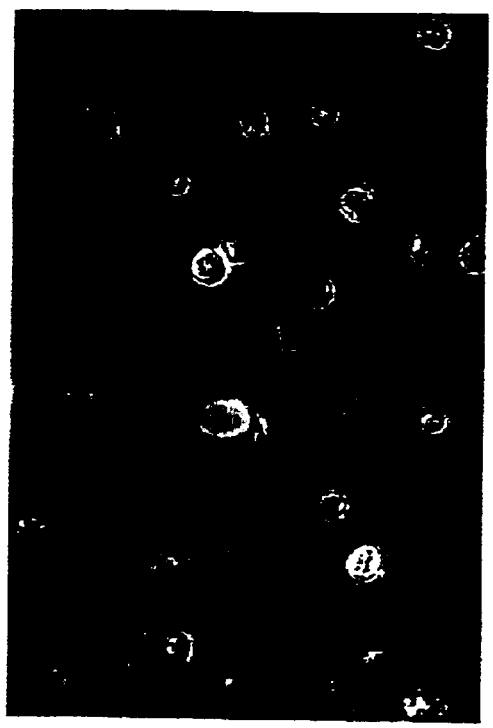
Fig. 21B
Fig. 21A

ERYTHROCYTIC CELLS AND METHOD FOR PRESERVING CELLS

RELATED PATENT APPLICATIONS

This is a continuation-in-part patent application of copending patent application Ser. No. 09/927,760, filed Aug. 9, 2001. Patent application Ser. No. 09/927,760 is a continuation-in-part patent application of copending patent application Ser. No. 09/828,627, filed Apr. 5, 2001. Patent application Ser. No. 09/828,627 is a continuation patent application of patent application Ser. No. 09/501,773, filed Feb. 10, 2000 now abandoned. Benefit of all earlier filing dates is claimed with respect to all common subject matter.

STATEMENT REGARDING FEDERAL SPONSORED RESEARCH AND DEVELOPMENT

Embodiments of this invention were made with Government support under Grant. No. N66001-00-C-8048, awarded by the Department of Defense Advanced Research Projects Agency (DARPA). Further embodiments of this invention were made with Government support under Grant Nos. HL57810 and HL61204, awarded by the National Institutes of Health. The Government has certain rights to embodiments of this invention.

FIELD OF THE INVENTION

Embodiments of the present invention generally broadly relate to living mammalian cells. More specifically, embodiments of the present invention generally provide for the preservation and survival of human cells, especially eukaryotic cells and erythrocytic cells.

Embodiments of the present invention also generally broadly relate to the therapeutic uses of blood platelets, eukaryotic cells, and erythrocytic cells; and more particularly to manipulations or modifications of platelets, eukaryotic cells, and erythrocytic cells, such as in preparing freeze-dried compositions that can be rehydrated at the time of application. When freeze-dried platelets are rehydrated, they have a normal response to thrombin and other agonists with respect to that of fresh platelets. When eukaryotic cells and erythrocytic cells are rehydrated, they are immediately restored to viability.

The inventive compositions and methods for embodiments of the present invention are useful in many applications, such as in medicine, pharmaceuticals, biotechnology, and agriculture, and including transfusion therapy, as hemostasis aids and for drug delivery.

BACKGROUND OF THE INVENTION

Blood transfusion centers are under considerable pressure to produce platelet concentrates for transfusion. The enormous quest for platelets necessitates storage of this blood component, since platelets are important contributors to hemostasis. Platelets are generally oval to spherical in shape and have a diameter of 2–4 μm. Today platelet rich plasma concentrates are stored in bloodbags at 22° C.; however, the shelf life under these conditions is limited to five days. The rapid loss of platelet function during storage and risk of bacterial contamination complicates distribution and availability of platelet concentrates. Platelets tend to become activated at low temperatures. When activated they are substantially useless for an application such as transfusion therapy. Therefore the development of preservation methods that will increase platelet lifespan is desirable.

Several techniques for preservation of platelets have been developed over the past few decades. Cryopreservation of platelets using various agents, such as glycerol (Valeri et al., Blood, 43, 131–136, 1974) or dimethyl sulfoxide, "DMSO" (Bock et al., Transfusion, 35, 921–924, 1995), as the cryoprotectant have been done with some success. The best results have been obtained with DMSO. However, a considerable fraction of these cells are partly lysed after thawing and have the shape of a balloon. These balloon cells are not responsive to various agonists, so that overall responsiveness of frozen thawed platelets to various agonists is reduced to less than 35% compared with fresh platelets. The shelf life of cryopreserved DMSO platelets at –80° C. is reported to be one year, but requires extensive washing and processing to remove cryoprotective agents, and even then the final product has a severe reduction in ability to form a clot.

Attempts to dry platelets by lyophilization have been described with paraformaldehyde fixed platelets (Read et al., Proc. Natl. Acad. Sci. USA, 92, 397401, 1995). U.S. Pat. No. 5,902,608, issued May 11, 1999, inventors Read et al. describe and claim a surgical aid comprising a substrate on which fixed, dried blood platelets are carried. These dried blood platelets are fixed by contacting the platelets to a fixative such as formaldehyde, paraformaldehyde, gutaraldehyde, or permanganate. Proper functioning of lyophilized platelets that have been fixed by such fixative agents in hemostasis is questionable.

Spargo et al., U.S. Pat. No. 5,736,313, issued Apr. 7, 1998, have described a method in which platelets are loaded overnight with an agent, preferably glucose, and subsequently lyophilized. The platelets are preincubated in a preincubation buffer and then are loaded with carbohydrate, preferably glucose, having a concentration in the range of about 100 mM to about 1.5 M. The incubation is taught to be conducted at about 10° C. to about 37° C., most preferably about 25° C.

U.S. Pat. No. 5,827,741, Beattie et al., issued Oct. 27, 1998, discloses cryoprotectants for human platelets, such as dimethylsulfoxide and trehalose. The platelets may be suspended, for example, in a solution containing a cryoprotectant at a temperature of about 22° C. and then cooled to below 15° C. This incorporates some cryoprotectant into the cells.

Trehalose is a disaccharide found at high concentrations in a wide variety of organisms that are capable of surviving almost complete dehydration (Crowe et al., Anhydrobiosis. Annul. Rev. Physiol., 54, 579–599, 1992). Trehalose has been shown to stabilize certain cells during freezing and drying (Leslie et al., Biochim. Biophys. Acta, 1192, 7–13, 1994; Beattie et al., Diabetes, 46, 519–523, 1997).

Other workers have sought to load platelets with trehalose through use of electroporation before drying under vacuum. However, electroporation is very damaging to the cell membranes and is believed to activate the platelets. Activated platelets have dubious clinical value.

Platelets have also been suggested for drug delivery applications in the treatment of various diseases, as is discussed by U.S. Pat. No. 5,759,542, issued Jun. 2, 1998, inventor Gurewich. This patent discloses the preparation of a complex formed from a fusion drug including an A-chain of a urokinase-type plasminogen activator that is bound to an outer membrane of a platelet.

Accordingly, a need exists for the effective and efficient preservation of platelets such that they maintain, or preserve, their biological properties, particularly their response to platelet agonists such as thrombin, and which can be practiced on a large, commercially feasible scale. Further, it would also be useful to expand the types of present vehicles that are useful for encapsulating drugs and used for drug delivery to targeted sites. Accordingly further, a need also exists for the effective and efficient preservation of eukaryotic cells and erythrocytic cells, such that these cells respectively maintain their biological properties and may readily become viable after storage.

SUMMARY OF THE INVENTION

In one aspect of the present invention, a dehydrated composition is provided comprising freeze-dried platelets that are effectively loaded with trehalose to preserve biological properties during freeze-drying and rehydration. These platelets are rehydratable so as to have a normal response to at least one agonist, such as thrombin. For example, substantially all freeze-dried platelets of the invention when rehydrated and mixed with thrombin (1 U/ml) form a clot within three minutes at 37° C. The dehydrated composition can include one or more other agents, such as antibiotics, antifungals, growth factors, or the like, depending upon the desired therapeutic application.

In another aspect of the present invention, a hemostasis aid is provided where the above-described freeze-dried platelets are carried on or by a biocompatible surface. A further component of the hemostasis aid may be a therapeutic agent, such as an antibiotic, an antifungal, or a growth factor. The biocompatible surface may be a bandage or a thrombic surface, such as freeze-dried collagen. Such a hemostasis aid can be rehydrated just before the time of application, such as by hydrating the surface on or by which the platelets are carried, or, in case of an emergency, the dry hemostasis treatment aid could be applied directly to the wound or burn and hydrated in situ.

Methods of making and using inventive embodiments are also described. One such method is a process of preparing a dehydrated composition comprising providing a source of platelets, effectively loading the platelets with trehalose to preserve biological properties, cooling the trehalose loaded platelets to below their freezing point, and lyophilizing the cooled platelets. The trehalose loading includes incubating the platelets at a temperature from greater than about 25° C. to less than about 40° C. with a trehalose solution having up to about 50 mm trehalose therein. The process of using such a dehydrated composition further may comprise rehydrating the platelets. The rehydration preferably includes a prehydration step wherein the freeze-dried platelets are exposed to warm, saturated air for a time sufficient to bring the water content of the freeze-dried platelets to between about 20 weight percent to about 35 weight percent.

In yet another aspect of the present invention, a drug delivery composition is provided comprising platelets having a homogeneously distributed concentration of a therapeutic agent therein. The drug delivery composition is particularly useful for targeting the encapsulated drug to platelet-mediated sites.

Practice of the present invention permits the manipulation or modification of platelets while maintaining, or preserving, biological properties, such as a response to thrombin. Further, use of the method to preserve platelets can be practiced on a large, commercially feasible scale, and avoids platelet activation. The inventive freeze-dried platelets, and hemostasis aids including the freeze-dried platelets, are substantially shelf stable at ambient temperatures when packaged in moisture barrier materials.

Embodiments of the present invention also provide a process for preserving and/or increasing the survival of dehydrated eukaryotic cells after storage comprising providing eukaryotic cells from a mammalian species (e.g., a human); loading the eukaryotic cells with a preservative (e.g., an oligosaccharide, such as trehalose); dehydrating the eukaryotic cells while maintaining a residual water content in the eukaryotic cells greater than about 0.15 (e.g., from about 0.20 to about 0.75) gram of water per gram of dry weight eukaryotic cells to increase eukaryotic cell survival, preferably to greater than about 80%, upon rehydrating after storage; storing the dehydrated eukaryotic cells having the residual water content greater than about 0.15 gram of water per gram of dry weight eukaryotic cells; and rehydrating the stored dehydrated eukaryotic cells with the stored dehydrated eukaryotic cells having an increase in survival following dehydration and storage. In a preferred embodiment, more than about 80% of the stored dehydrated cells survive the dehydration and storage.

Embodiments of the present invention further provide a process of preparing loaded eukaryotic cells comprising providing eukaryotic cells selected from a mammalian species; and loading (e.g., with an oligosaccharide solution and/or with or without a fixative) an oligosaccharide (e.g., trehalose) into the eukaryotic cells at a temperature greater than about 25° C. (e.g., greater than about 25° C. but less than about 50° C., such as from about 30° C. to less than about 50° C., or from about 30° C. to about 40° C.) to produce loaded eukaryotic cells. The loading comprises taking up external oligosaccharide via fluid phase endocytosis from an oligosaccharide solution at the temperature greater than about 25° C. The loading further comprises incubating the eukaryotic cells at the temperature greater than about 25° C. with the oligosaccharide solution. For these embodiments of the present invention, the eukaryotic cells are preferably human eukaryotic cells, such as, by way of example only, eukaryotic cells selected from the group of eukaryotic cells consisting of mesenchymal stem cells and epithelial 293H cells.

Embodiments of the present invention also further provide a solution for loading eukaryotic cells comprising eukaryotic cells selected from a mammalian species; and an oligosaccharide solution containing the eukaryotic cells and a temperature greater than about 25° C. for loading oligosaccharide from the oligosaccharide solution into the eukaryotic cells. External oligosaccharide is taken up via fluid phase endocytosis from the oligosaccharide solution at a temperature ranging from about 30° C. to less than about 42° C. An eukaryotic cell composition is also provided as broadly comprising eukaryotic cells loaded internally with an oligosaccharide, preferably trehalose, from an oligosaccharide solution at a temperature greater than about 25° C.

Embodiments of the present invention yet also further provide a generally dehydrated composition comprising freeze-dried eukaryotic cells selected from a mammalian species (e.g., a human) and being effectively loaded internally (e.g., incubating the eukaryotic cells at a temperature from about 30° C. to less than about 50° C. so as to uptake external trehalose via fluid phase endocytosis) with at least about 10 mM trehalose therein to preserve biological properties during freeze-drying and rehydration. The amount of trehalose loaded inside the freeze-dried eukaryotic cells is preferably from about 10 mM to about 50 mM. The freeze-dried eukaryotic cells comprise at least about 0.15 (e.g., from about 0.20 to about 0.75) gram of residual water per gram of dry weight eukaryotic cells to increase eukaryotic cell survival upon rehydrating.

Aspects of embodiments of the present invention also include a process for preparing a dehydrated composition.

The process comprises providing eukaryotic cells selected from a mammalian species (e.g., a human); loading internally the eukaryotic cells with from about 10 mM to about 50 mM of an oligosaccharide (e.g., trehalose) therein to preserve biological properties. The loading includes incubating the eukaryotic cells at a temperature from about 30° C. to less than about 50° C., preferably from about 30° C. to about 40° C., more preferably from about 34° C. to about 37° C., with an oligosaccharide solution having up to about 50 mM oligosaccharide therein; cooling the loaded eukaryotic cells to below their freezing point; and lyophilizing the cooled eukaryotic cells. Lyophilizing preferably is conducted so as to leave a residual water content of less than about 0.40 gram of water per gram of dry weight eukaryotic cells, preferably greater than about 0.15 gram of water per gram of dry weight eukaryotic cells, but more preferably less than about 0.40 gram of water per gram of dry weight of eukaryotic cells.

Further aspects of embodiments of the present invention include a process for increasing the loading efficiency of an oligosaccharide into eukaryotic cells. The process comprises providing eukaryotic cells having a first phase transition temperature range and a second phase transition temperature range (e.g., a temperature greater than about 25° C., such as from about 30° C. to less than about 50° C.) which is greater than the first phase transition temperature range; disposing the eukaryotic cells in an oligosaccharide solution for loading an oligosaccharide (e.g., trehalose) into the eukaryotic cells; and heating the oligosaccharide solution to the second phase transition temperature range to increase the loading efficiency of the oligosaccharide into the eukaryotic cells. The process additionally comprises taking up external oligosaccharide via fluid phase endocytosis from the oligosaccharide solution.

The present invention also comprises additional embodiments which include a process for increasing the cooperativity of a phase transition of an erythrocytic cell comprising providing an erythrocytic cell having an alcohol (e.g. a sterol) and a phase transition, and removing at least a portion of the alcohol from the erythrocytic cell to increase the cooperativity of the phase transition of the erythrocytic cell. The erythrocytic cell preferably comprises an erythrocytic membrane including the alcohol and the phase transition. Another embodiment of the present invention provides a process for producing a phase transition temperature range in an erythrocytic cell comprising providing an erythrocytic cell including an alcohol and at least two phase transition temperature ranges, and removing at least a portion of the alcohol from the erythrocytic cell to produce an erythrocytic cell having at least three phase transition temperature ranges. The erythrocytic cell for this feature or aspect of the invention preferably includes an erythrocytic membrane including at least a portion of the alcohol and at least a portion of the two phase transition temperature ranges. After the erythrocytic cell is produced, the produced erythrocytic cell preferably comprises the erythrocytic membrane including at least a portion of the three phase transition temperature ranges after removal of at least a portion of the alcohol.

A further embodiment of the present invention provides a process for loading an oligosaccharide into erythrocytic cells comprising providing erythrocytic cells having an alcohol (e.g. a sterol); removing at least a portion of the alcohol from the erythrocytic cells to produce erythrocytic cells having a phase transition temperature range selected from the group of temperature ranges consisting of a low phase transition temperature range, an intermediate phase transition temperature range, and a high phase transition temperature range; and disposing the erythrocytic cells in an oligosaccharide solution for loading an oligosaccharide (e.g., trehalose) into the erythrocytic cells. The oligosaccharide solution preferably includes a temperature in a range that approximates the range of temperatures for the phase transition temperature range. The process for loading the oligosaccharide into the erythrocytic cells may additionally comprise heating the oligosaccharide solution, such as to a temperature in the high phase transition temperature range, to increase the loading efficiency of the oligosaccharide into the erythrocytic cells. The process may further additionally comprise taking up external oligosaccharide via lipid phase endocytosis from the oligosaccharide solution. The erythrocytic cells do not necessarily include a fixative.

Another embodiment of the present invention provides a process for increasing the survival of dehydrated erythrocytic cells after storage. The process for increasing survival preferably comprises providing erythrocytic cells from a mammalian species (e.g., a human being) and having an alcohol (e.g. a sterol); removing, preferably at least part of, the alcohol from the erythrocytic cells; and loading the erythrocytic cells with a preservative (e.g., an oligosaccharide). The loaded erythrocytic cells are then dehydrated (e.g., by lyophilizing) while maintaining a residual water content in the erythrocytic cells equal to or less than about 0.30 gram of residual water per gram of dry weight erythrocytic cells to increase erythrocytic cell survival upon rehydrating after storage. The process for increasing survival also preferably comprises storing the dehydrated erythrocytic cells having the residual water content equal to or less than about 0.30 gram of residual water per gram of dry weight erythrocytic cells; and rehydrating the stored dehydrated erythrocytic cells with the stored dehydrated erythrocytic cells surviving dehydration and storage. The loading may be without a fixative and may comprise taking up external oligosaccharide via lipid phase endocytosis from the oligosaccharide solution. The loading may also, or alternatively, comprise incubating the erythrocytic cells with the oligosaccharide solution. The loaded erythrocytic cells may be cooled to a temperature below their freezing point prior to dehydrating the erythrocytic cells. The residual water content of the erythrocytic cells preferably ranges from about 0.00 gram of residual water per gram of dry weight erythrocytic cells to less than about 0.30 gram of residual water per gram of dry weight erythrocytic cells.

A further embodiment of the present invention provides a process of preparing a dehydrated composition comprising providing erythrocytic cells selected from a mammalian species and including an alcohol (e.g. a sterol); loading internally the erythrocytic cells with more than about 10 mM of an oligosaccharide therein to preserve biological properties; cooling the loaded erythrocytic cells to below their freezing point; and lyophilizing the cooled erythrocytic cells. The loading of the erythrocytic cells for this aspect of the invention may comprise incubating the erythrocytic cells with an oligosaccharide solution having the oligosaccharide therein and a temperature in a range of temperatures selected from the group consisting of a low phase transition temperature range, an intermediate phase transition temperature range, and a high phase transition temperature range. The lyophilizing is conducted so as to leave a residual water content of equal to or less than about 0.3 gram water per gram dry weight of erythrocytic cells. Preferably, greater than about 80% of the erythrocytic cells survive dehydration and storage. The process of preparing a dehydrated composition may additionally comprise prehydrating the erythrocytic cells, and subsequently hydrating the prehydrated erythrocytic cells.

An additional further embodiment of the present invention comprises a process of preparing loaded erythrocytic cells comprising removing at least a portion of an alcohol (e.g. a sterol) from erythrocytic cells to produce erythrocytic cells having at least three phase transition temperature ranges, and loading (e.g., with an oligosaccharide solution) an oligosaccharide into the erythrocytic cells at a temperature in a range of temperatures approximating one of the three phase transition temperature ranges to produce loaded erythrocytic cells. As previously indicated, the loading may comprise incubating the erythrocytic cells with the oligosaccharide solution at a temperature in a range of temperatures approximating one of the three phase transition temperature ranges.

Additional features of the present invention include a solution for loading erythrocytic cells, an erythrocytic cell composition, and a generally dehydrated composition. The solution for loading erythrocytic cells comprises reduced-alcohol (e.g. reduced-sterol) erythrocytic cells having three phase transition temperature ranges, and an oligosaccharide solution containing the reduced-alcohol erythrocytic cells for loading oligosaccharide from the oligosaccharide solution into the reduced-alcohol erythrocytic cells. External oligosaccharide is taken up via lipid phase endocytosis from the oligosaccharide solution at a temperature in a range of temperatures approximating one of the three phase transition temperature ranges. The erythrocytic cell composition comprises reduced-alcohol erythrocytic cells loaded internally with an oligosaccharide from an oligosaccharide solution. Preferably, the oligosaccharide is loaded from the oligosaccharide solution at a temperature in a range of temperatures selected from the group consisting of a low phase transition temperature range, an intermediate phase transition temperature range, and a high phase transition temperature range. The generally dehydrated composition comprises freeze-dried reduced-alcohol erythrocytic cells effectively loaded internally with at least about 10 mM of the oligosaccharide (e.g., trehalose) therein to preserve biological properties during freeze-drying and rehydration. The amount of the oligosaccharide loaded inside the freeze-dried reduced-alcohol erythrocytic cells may be from about 10 mM to about 200 mM. The freeze-dried reduced-alcohol erythrocytic cells may comprise less than about 0.30 gram of residual water per gram of dry weight erythrocytic cells to increase erythrocytic cell survival upon rehydrating.

The sterol may comprise a steroid alcohol, preferably a steroid alcohol having at least one side chain having 8 to 10 carbon atoms. Preferably further, the sterol may comprise from 25 to 27 carbon atoms. More preferably, the sterol comprises cholesterol, such as cholesterol having the formula:

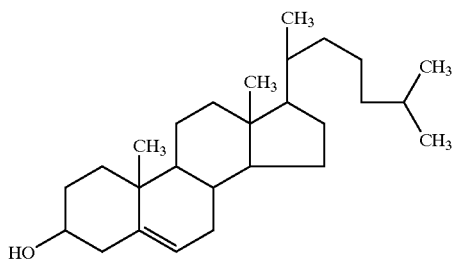

The erythrocytic cells preferably comprise erythrocytic membranes respectively including the low phase transition temperature range, the intermediate phase transition, and the high phase transition temperature range. The low phase transition temperature range is greater than about 2° C., such as a temperature greater than about 2° C. to a temperature equal to or less than about 20° C. The intermediate phase transition temperature range is preferably greater than about 20° C., such as a temperature greater than about 20° C. to a temperature equal to or less than about 30° C. The high phase transition temperature range is preferably greater than about 30° C., such as a temperature greater than about 30° C. to a temperature equal to or less than about 50° C., more preferably from about 30° C. to about 40° C., or from about 32° C. to about 38° C.

These provisions together with the various ancillary provisions and features which will become apparent to those skilled in the art as the following description proceeds, are attained by the processes, platelets, eukaryotic cells, and erythrocytic cells of the present invention, preferred embodiments thereof being shown with reference to the accompanying drawings, by way of example only, wherein:

BRIEF DESCRIPTION OF THE DRAWINGS

In the drawings:

FIG. 1 graphically illustrates the loading efficiency of trehalose plotted versus incubation temperature of human platelets;

FIG. 2 graphically illustrates the percentage of trehalose-loaded human platelets following incubation as a function of incubation time;

FIG. 3 graphically illustrates the internal trehalose concentration of human platelets versus external trehalose concentration as a function of temperature at a constant incubation or loading time;

FIG. 4 graphically illustrates the loading efficiency of trehalose into human platelets as a function of external trehalose concentration;

FIG. 5 graphically illustrates the recovery of platelet embodiments after lyophilization and direct rehydration with various concentrations of trehalose in the drying buffer, and in a combination of 30 mM trehalose and one percent HSA in the drying buffer;

FIG. 6 graphically illustrates the uptake of FITC dextran versus the external concentration compared with that of the marker, LYCH (with an incubation time of four hours);

FIG. 7 graphically illustrates the effect of prehydration on optical density of platelets;

FIG. 8 illustrates the response of 500 μl platelets solution (with a platelet concentration of $0.5 \times 10^8$ cells/ml) that was transferred to aggregation vials, thrombin added (lU/ml) to each sample, and the samples stirred for three minutes at 37° C., where panel (A) are the prior art platelets and panel (B) are the inventive platelets;

FIG. 9 graphically illustrates clot formation where the absorbance falls sharply upon addition of thrombin (1 U/ml) and the platelet concentration drops from $250 \times 10^6$ platelets/ml to below $2 \times 10^6$ platelets/ml after three minutes for the inventive platelets;

FIG. 14A is a micrograph at a 100× magnification of healthy mesenchymal stem cell culture prior to harvest by trypsinization;

FIG. 14B is a micrograph at a 320× magnification of the healthy mesenchymal stem cell culture of FIG. 14A prior to harvest by trypsinization;

FIG. 15A is a 100× magnified image of dry lyophilization "cake" of mesenchymal stem cells encased in strands of matrix containing trehalose and BSA;

FIG. 15B is a 100× magnified image of prehydrated lyophilization "cake" of mesenchymal stem cells encased in strands of matrix containing trehalose and BSA;

FIG. 17A is a micrograph of mesenchymal stem cells from a prehydrated sample at two days post rehydration and illustrating an attached cell and beginning to show characteristic stretched morphology;

FIG. 17B is a micrograph of mesenchymal stem cells from a prehydrated sample at five days post rehydration, with nuclei clearly visible in several of the cells;

FIG. 21A is a micrograph at 320× magnification of epithelial 293H cells 24 hours following rehydration, with refractile whole cells still visible;

FIG. 21B is an enlarged view of the dashed square cell field in FIG. 21A with a refractile cell marked by an arrow;

DETAILED DESCRIPTION OF PREFERRED EMBODIMENTS OF THE INVENTION

Figure 10:
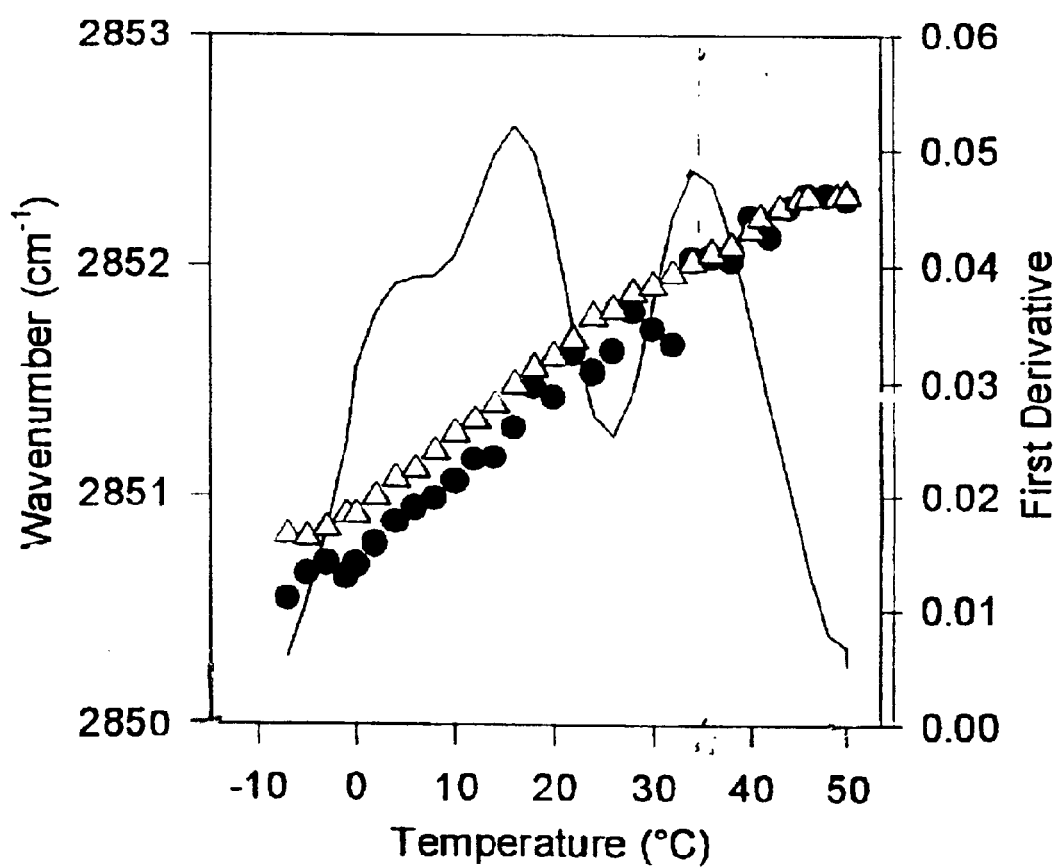
FIG. 10 is a graph illustrating temperatures for membrane phase transition in hydrated mesenchymal stem cells by Fourier transform infrared (FTIR) spectroscopy, with the solid line graph indicating the first derivative of the set of data shown in filled circles.

Compositions and embodiments of the invention include platelets that have been manipulated (e.g. by freeze-drying) or modified (e.g. loaded with drugs), and that are useful for therapeutic applications, particularly for platelet transfusion therapy, as surgical or hemostasis aids, such as wound dressings, bandages, and as sutures, and as drug-delivery vehicles. As has been known, human platelets have a phase transition between 12° C. and 20° C. We have found that platelets have a second phase transition between 30° C. and 37° C. Our discovery of this second phase transition temperature range suggests the possible use of platelets as vehicles for drug delivery because we can load platelets with various useful therapeutic agents without causing abnormalities that interfere with normal platelet responses due to changes, such as in the platelet outer membranes.

For example, platelets may be loaded with anti-thrombic drugs, such as tissue plasminogen activator (TPA) so that the platelets will collect at the site of a thrombus, as in an heart attack, and release the "clot busting" drug or drugs that are encapsulated and have been targeted by the platelets. Antibiotics can also be encapsulated by the platelets, since lipopolysaccharides produced by bacteria attract platelets. Antibiotic loaded platelets will bring the selected antibiotics to the site of inflammation. Other drugs that can be loaded include anti-mitotic agents and anti-angiogenic agents. Since platelets circulate in newly formed vessels associated with tumors, they could deliver anti-mitotic drugs in a localized fashion, and likely platelets circulating in the neovasculature of tumors can deposit anti-angiogenic drugs so as to block the blood supply to tumors. Thus, platelets loaded with a selected drug in accordance with this invention can be prepared and used for therapeutic applications. The drug-loaded platelets are particularly contemplated for blood-borne drug delivery, such as where the selected drug is targeted to a site of platelet-mediated forming thrombi or vascular injury. The so-loaded platelets have a normal response to at least one agonist, particularly to thrombin. Such platelets can be loaded additionally with trehalose, if preservation by freeze-drying is intended.

The key component for compositions and apparatus of embodiments of the invention, when preservation will be by freeze-drying, is a lyoprotectant, preferably an oligosaccharide, more preferably trehalose, because we have found that platelets that are effectively loaded with trehalose preserve biological properties during freeze-drying (and rehydration). This preservation of biological properties, such as the normal clotting response in combination with thrombin, is necessary so that the platelets following preservation can be successfully used in a variety of therapeutic applications.

Normal hemostasis is a sequence of interactions in which blood platelets contribute, beginning with adhesion of platelets to an injured vessel wall. The platelets form an aggregate that accelerates coagulation. A complex, termed the glycoprotein (GP) 1b-IX-V complex, is involved in platelet activation by providing a binding site on the platelet surface for the potent agonist, α-thrombin. α-thrombin is a serine protease that is released from damaged tissue. Thus, it is important that the manipulations and modifications in accordance with this invention do not activate the platelets. Further, it is normally preferred that the platelets be in a resting state. Otherwise, the platelets will activate.

Although for most contemplated therapeutic applications the clotting response to thrombin is key, the inventive freeze-dried platelets after rehydration will also respond to other agonists besides thrombin. These include collagen, ristocetin, and ADP (adenosine diphosphate), all of which are normal platelet agonists. These other agonists typically pertain to specific receptors on the platelet's surface.

Broadly, the preparation of preserved platelets in accordance with the invention comprises the steps of providing a source of platelets, loading the platelets with a protective oligosaccharide at a temperature above about 25° C. and less than about 40° C., cooling the loaded platelets to below −32° C., and lyophilizing the platelets.

In order to provide a source of platelets suitable for the inventive preservation process, the platelets are preferably isolated from whole blood. Thus, platelets used in this invention preferably have had other blood components (erythrocytes and leukocytes) removed prior to freeze-drying. The removal of other blood components may be by procedures well known to the art, which typically involve a centrifugation step.

The amount of the preferred trehalose loaded inside the inventive platelets is from about 10 mM to about 50 mM, and is achieved by incubating the platelets to preserve biological properties during freeze-drying with a trehalose solution that has up to about 50 mM trehalose therein. Higher concentrations of trehalose during incubation are not preferred, as will be more fully explained later. The effective loading of trehalose is also accomplished by means of using an elevated temperature of from greater than about 25° C. to less than about 40° C., more preferably from about 30° C. to less than about 40° C., most preferably about 37° C. This is due to the discovery of the second phase transition for platelets. As can be seen by FIG. 1, the trehalose loading efficiency begins a steep slope increase at incubation temperatures above about 25° C. up to about 40° C. The trehalose concentration in the exterior solution (that is, the loading buffer) and the temperature during incubation together lead to a trehalose uptake that seems to occur primarily through fluid phase endocytosis (that is, pinocytosis). Pinocytosed vesicles lyse over time, which results in a homogeneous distribution of trehalose in the platelets, does not activate the platelets, and can be applied for large scale production. FIG. 2 illustrates the trehalose loading efficiency as a function of incubation time.

As may be gathered from various of the figures, in preparing particularly preferred embodiments, platelets may be loaded with trehalose by incubation at 37° C. for about four hours. The trehalose concentration in the loading buffer is preferably 35 mM, which results in an intracellular trehalose concentration of around 20 mM, but in any event is most preferably not greater than about 50 mM trehalose. At trehalose concentrations below about 50 mM, platelets have a normal morphological appearance.

Human platelets have a phase transition between 12° C. and 20° C. We found relatively poor loading when the platelets were chilled through the phase transition. Thus, in practicing the method described by U.S. Pat. No. 5,827,741, of which some of us are coinventors, only a relatively modest amount of trehalose may be loaded into platelets.

In this application, we have further investigated the phase transition in platelets and have found a second phase transition between 30° C. and 37° C. We believe that the excellent loading we obtain at about 37° C. is in some way related to this second phase transition. Without being limited by theory, we also believe that pinocytosis is involved, but it may be that the second phase transition itself stimulates the pinocytosis at high temperatures. It may be that other oligosaccharides when loaded in this second phase transition in amounts analogous to trehalose could have similar effects.

In any case, it is fortuitous that the loading can be done at elevated temperatures in view of the fact that chilling platelets slowly—a requirement for using the first, or lower, phase transition between 20° C. and 12° C. to introduce trehalose—is well known to activate them (Tablin et al., *J. Cell. Physiol.*, 168, 305313, 1996). Our relatively high temperature loading, regardless of the mechanism, is thus unexpectedly advantageous both by providing increased loading as well as surprisingly, obviating the activation problem.

Turning to FIG. 6, one sees that we have loaded other, larger molecules into the platelets. In FIG. 6 an illustrative large molecule (FITC dextran) was loaded into the platelets. This illustrates that a wide variety of water-soluble, therapeutic agents can be loaded into the platelets by utilizing the second phase transition, as we have shown may be done with trehalose and with FITC dextran, while still maintaining characteristic platelet surface receptors and avoiding platelet activation.

We have achieved loading efficiencies by practicing the invention with values as high as 61% after four hours incubation. The plateau is not yet reached after four hours. The high loading efficiency of trehalose is a strong indication that the trehalose is homogeneously distributed rather than located in pinocytosed vesicles, and we expect similar results for loading other therapeutic agents. A loading efficiency of 61% in an external concentration of 25 mM corresponds to a cytosolic concentration of 15 mM. If trehalose were only located in endosomes of 0.1 micrometer, the vesiculation number would be more than 1000. It is unlikely that such a high number of vesicles would be present in platelets next to the other platelet organelles. We therefore believe that the pinocytosed vesicles lyse in the cytoplasm. This results in a homogeneous distribution of trehalose rather than punctuated loading in small vesicles. It is also possible that the trehalose is crossing the membrane due to the phase transition between 30° C. and 37° C.

We have found that the endocytotic uptake route is blocked at sugar concentrations above 0.1 M. Consequently, we prefer not to use sugar concentrations higher than about 50 mM in the loading buffer, because at some point above this value we have found swelling and morphological changes of the platelets. Thus, we have found that platelets become swollen after four hours incubation at 37° C. in 75 mM trehalose. Further, at concentrations higher than 50 mM the internal trehalose concentration begins to decrease. By contrast to the present invention, the platelet method taught by Spargo et al., U.S. Pat. No. 5,736,313, loads with carbohydrate in the range beginning at about 100 mM and going up to 1.5 M. As noted, we find a high concentration of loading buffer, at least with trehalose, to lead to swelling and morphological changes.

The effective loading of platelets with trehalose is preferably conducted by incubating for at least about two hours, preferably for at least about four hours. After this loading, then the platelets are cooled to below their freezing point and lyophilized.

Before freezing, the platelets should be placed into a resting state. If not in the resting state, platelets would likely activate. In order to place the platelets in a resting state, a variety of suitable agents, such as calcium channel blockers, may be used. For example, solutions of adenine, adenosine or iloprost are suitable for this purpose. Another suitable agent is PGE1 (prostaglandin E1). It is important that the platelets are not swollen and are completely in the resting state prior to drying. The more they are activated, the more they will be damaged during freeze-drying.

After the platelets have been effectively loaded with trehalose and are in a resting state, then the loading buffer is removed and the platelets are contacted with a drying buffer. The drying buffer should include trehalose, preferably in amounts up to about 100 mM. The trehalose in the drying buffer assists in spatially separating the platelet as well as stabilizing the platelet membranes on the exterior. The drying buffer preferably also includes a bulking agent (to further separate the platelets). Albumin may serve as a bulking agent, but other polymers may be used with the same effect. If albumin is used, it is preferably from the same species as the platelets. Suitable other polymers, for example, are water-soluble polymers such as HES (hydroxy ethyl starch) and dextran.

The trehalose loaded platelets in drying buffer are then cooled to a temperature below about −32° C. A cooling, that is, freezing, rate is preferably between −30° C. and −1° C./min. and more preferably between about −2° C./min to −5° C./min.

The lyophilization step is preferably conducted at a temperature below about −32° C., for example conducted at about −40° C., and drying may be continued until about 95 weight percent of water has been removed from the platelets. During the initial stages of lyophilization, the pressure is preferably at about $10 \times 10^{-6}$ torr. As the samples dry, the temperature can be raised to be warmer than −32° C. Based upon the bulk of the sample, the temperature and the pressure it can be emperically determined what the most efficient temperature values should be in order to maximize the evaporative water loss. Freeze-dried compositions of the invention preferably have less than about 5 weight percent water.

The freeze-dried platelets may be used by themselves, dissolved in a physiologically acceptable solution, or may be a component of a biologically compatible (biocompatible) structure or matrix, which provides a surface on or by which the freeze-dried platelets are carried. The freeze-dried platelets can be, for example, applied as a coating to or impregnated in a wide variety of known and useful materials suitable as biocompatible structures for therapeutic applications. The earlier mentioned U.S. Pat. No. 5,902,608, for example, discusses a number of materials useful for surgical aid, wound dressings, bandages, sutures, prosthetic devices, and the like. Sutures, for example, can be monofilament or braided, can be biodegradable or nonbiodegradable, and can be made of materials such as nylon, silk, polyester, cotton, catgut, homopolymers, and copolymers of glycolide and lactide, etc. Polymeric materials can also be cast as a thin film, sterilized, and packaged for use as a wound dressing. Bandages may be made of any suitable substrate material, such as woven or nonwoven cotton or other fabric suitable for application to or over a wound, may optionally include a backing material, and may optionally include one or more adhesive regions on the face surface thereof for securing the bandage over the wound.

The freeze-dried platelets, whether by themselves, as a component of a vial-compatible structure or matrix, and optionally including other dry or freeze-dried components, may be packaged so as to prevent rehydration until desired. The packaging may be any of the various suitable packagings for therapeutic purposes, such as made from foil, metallized plastic materials, and moisture barrier plastics (e.g. high-density polyethylene or plastic films that have been created with materials such as SiOx), cooling the trehalose loaded platelets to below their freezing point, and lyophilizing the cooled platelets. The trehalose loading includes incubating the platelets at a temperature from greater than about 25° C. to less than about 40° C. with a trehalose solution having up to about 50 mM trehalose therein. The process of using such a dehydrated composition comprises rehydrating the platelets. The rehydration preferably includes a prehydration step sufficient to bring the water content of the freeze-dried platelets to between about 20 weight percent and about 50 percent, preferably from about 20 weight percent to about 40 weight percent.

When reconstitution is desired, prehydration of the freeze-dried platelets in moisture saturated air followed by rehydration is preferred. Use of prehydration yields cells with a much more dense appearance and with no balloon cells being present. Prehydrated, previously lyophilized platelets of the invention resemble fresh platelets. This is illustrated, for example, by FIG. 7. As can be seen, the previously freeze-dried platelets can be restored to a condition that looks like fresh platelets.

Before the prehydration step, it is desirable to have diluted the platelets in the drying buffer to prevent aggregation during the prehydration and rehydration. At concentrations below about $3 \times 10^8$ cells/ml, the ultimate recovery is about 70% with no visible aggregates. Prehydration is preferably conducted in moisture saturated air, most preferably is conducted at about 37° C. for about one hour to about three hours. The preferred prehydration step brings the water content of the freeze-dried platelets to between about 20 weight percent to about 50 weight percent.

The prehydrated platelets may then be fully rehydrated. Rehydration may be with any aqueous based solutions, depending upon the intended application. In one preferred rehydration, we used plasma, which resulted in about 90% recovery.

Since it is frequently desirable to dilute the platelets to prevent aggregation when the freeze-dried platelets are once again hydrated, it may then be desired or necessary for particular clinical applications to concentrate the platelets. Concentration can be by any conventional means, such as by centrifugation. In general, a rehydrated platelet composition will preferably have $10^6$ to $10^{11}$ platelets per ml, more preferably $10^8$ to $10^{10}$ platelets per ml.

By contrast with the previous attempts at freeze drying platelets, we show here that with a very simple loading, freeze-drying and rehydration protocol one obtains platelets that are morphologically intact after rehydration, and have an identical response to thrombin as do fresh platelets. Moreover, the concentration of thrombin to give this response is a physiological concentration—1 U/ml.

For example, FIG. 8, panel (A), illustrates the clot formation for fresh platelets and in panel (B) for platelets that have been preserved and then rehydrated in accordance with this invention. The cell counts that were determined after three minutes exposure to thrombin were zero for both the fresh platelets and the previously freeze-dried platelets of the invention.

FIG. 9 graphically illustrates clotting as measured with an aggregometer. With this instrument one can measure the change in transmittance when a clot is formed. The initial platelet concentration was $250 \times 10^6$ platelets/ml, and then thrombin (1 U/ml) was added and the clot formation was monitored with the aggregometer. The absorbance fell sharply and the cell count dropped to below $2 \times 10^6$ platelets/ml after three minutes, which was comparable to the results when the test was run with fresh platelets as a control.

Although platelets for use in this invention preferably have had other blood components removed before freeze-drying, compositions and apparatuses of embodiments of the invention may also include a variety of additional therapeutic agents. For example, particularly for embodiments contemplated in hemostasis applications, antifungal and antibacterial agents are usefully included with the platelets, such as being admixed with the platelets. Embodiments can also include admixtures or compositions including freeze-dried collagen, which provides a thrombogenic surface for the platelets. Other components that can provide a freeze-dried extracellular matrix can be used, for example, components composed of proteoglycan. Yet other therapeutic agents that may be included in inventive embodiments are growth factors. When the embodiments include such other components, or admixtures, they are preferably in dry form, and most preferably are also freeze-dried. We also contemplate therapeutic uses of the composition where additional therapeutic agents may be incorporated into or admixed with the platelets in hydrated form. The platelets, as earlier mentioned, can also be prepared as to encapsulate drugs in drug delivery applications. If trehalose is also loaded into the platelet interiors, then such drug-encapsulated platelets may be freeze-dried as has been earlier described.

The platelets should be selected of the mammalian species for which treatment is intended (e.g. human, equine, canine, feline, or endangered species), most preferably human.

The injuries to be treated by applying hemostasis aids with the platelets include abrasions, incisions, burns, and may be wounds occurring during surgery of organs or of skin tissue. The platelets of the invention may be applied or delivered to the location of such injury or wound by any suitable means. For example, application of inventive embodiments to burns can encourage the development of scabs, the formation of chemotactic gradients, of matrices for inducing blood vessel growth, and eventually for skin cells to move across and fill in the burn.

For transfusion therapy, inventive compositions may be reconstituted (rehydrated) as pharmaceutical formulations and administered to human patients by intravenous injection. Such pharmaceutical formulations may include any aqueous carrier suitable for rehydrating the platelets (e.g., sterile, physiological saline solution, including buffers and other therapeutically active agents that may be included in the reconstituted formulation). For drug delivery, the inventive compositions will typically be administered into the blood stream, such as by i.v.

In additional embodiments of the present invention, it has been discovered that the general findings with respect to platelets are broadly applicable to cells, particularly eukaryotic cells. The term "eukaryotic cell" is used to mean any nucleated cell, i.e., a cell that possesses a nucleus surrounded by a nuclear membrane, as well as any cell that is derived by terminal differentiation from a nucleated cell, even though the derived cell is not nucleated. Examples of the latter are terminally differentiated human red blood cells. Mammalian, and particularly human, eukaryotes are preferred. Suitable mammalian species include by way of example only, not only human, but also equine, canine, feline, or endangered species.

Thus, compositions and embodiments of the present invention include eukaryotic cells (e.g., mesenchymal stem cells, epithelial 293H cells, etc) that have been manipulated (e.g. by freeze-drying) or modified (e.g. loaded with preservatives) and that are useful for well known therapeutic applications. We have discovered that eukaryotic cells have a first phase transition between about −10° C. and about 24° C. and a second phase transition at temperatures commencing with about 25° C. and terminating at temperatures of about 50° C. More specifically, we have discovered that eukaryotic cells have a second phase transition at a temperature greater than about 25° C., such as a temperature ranging from a temperature greater than about 25° C. to a temperature less than about 50° C., including a temperature ranging from about 30° C. to less than about 50° C., more particularly a temperature ranging from about 30° C. to about 40° C., most preferably a temperature ranging from about 32° C. to about 38° C., such as from about 34° C. to about 37° C. Our discovery of this second phase transition suggests improving the preservation of eukaryotic cells by optimizing loading eukaryotic cells with a preservative (.e.g., an oligosaccharide, such as trehalose), and by optimizing the storage and rehydration of eukaryotic cells. We have more specifically discovered that eukaryotic cells, which were loaded with trehalose at the second phase transition temperature range and freeze dried, are viable immediately following rehydration and appear healthy because the membranes are intact and the nuclei are clearly visible and are of normal morphology.

One of the salient components for compositions and apparatus of additional embodiments of the present invention, when cell preservation will be assisted by freeze-drying, is an oligosaccharide, preferably trehalose, because we have discovered that eukaryotic cells which are effectively loaded with trehalose preserve biological properties during freeze drying (and rehydration). This preservation of biological properties, such as the immediate restoration of viability following rehydration, is necessary so that the eukaryotic cells following preservation can be successfully used in a variety of well known therapeutic applications. Preferably, the preparation of preserved eukaryotic cells in accordance with embodiments of the present invention broadly comprises the steps of providing a source of eukaryotic cells, loading the eukaryotic cells with a protective preservative (e.g., an oligosaccharide) at a temperature above 25° C. and less than about 50° C., cooling the loaded eukaryotic cells to below −32° C., and lyophilizing the eukaryotic cells.

The source of the eukaryotic cells may be any suitable source such that the eukaryotic cells may be cultivated in accordance with well known procedures, such as incubating the eukaryotic cells with a suitable serum (e.g., fetal bovine serum). After the eukaryotic cells are cultured, they are subsequently harvested by any conventional procedure, such as by trypsinization, in order to be loaded with a protective preservative. The eukaryotic cells are preferably loaded by growing the eukaryotic cells in a liquid tissue culture medium. The preservative (e.g., an oligosaccharide, such as trehalose) is preferably dissolved in the liquid tissue culture medium, which includes any liquid solution capable of preserving living cells and tissue. Many types of mammalian tissue culture media are known in the literature and available from commercial suppliers, such as Sigma Chemical Company, St. Louis, Mo., USA: Aldrich Chemical Company, Inc., Milwaukee, Wis., USA; and Gibco BRL Life Technologies, Inc., Grand Island, N.Y., USA. Examples of media that are commercially available are Basal Medium Eagle, CRCM-30 Medium, CMRL Medium-1066, Dulbecco's Modified Eagle's Medium, Fischer's Medium, Glasgow Minimum Essential Medium, Ham's F-10 Medium, Ham's F-12 Medium, High Cell Density Medium, Iscove's Modified Dulbecco's Medium, Leibovitz's L-15 Medium, McCoy's 5A Medium (modified), Medium 199, Minimum Essential Medium Eagle, Alpha Minimum Essential Medium, Earle's Minimum Essential Medium, Medium NCTC 109, Medium NCTC 135, RPMMI-1640 Medium, William's Medium E, Waymouth's MB 752/1 Medium, and Waymouth's MB 705/1 Medium.

When the preservative to be loaded in the eukaryotic cells is trehalose, the actual amount of trehalose dissolved in the liquid tissue culture medium may vary, although considerations of the economical use of materials and labor, and considerations of the cryopreservation protocol, i.e., the choice of procedural steps used for cooling and thawing the eukaryotic cells together with the cooling and thawing rates, may affect the selection of concentration ranges that will provide the most efficient and effective preservation. In the case of trehalose for one embodiment of the present invention, the concentration of trehalose in the cryopreservation medium (i.e., the tissue culture medium plus added trehalose) ranges from about 10 mM and about 1.5 M, preferably between about 100 mM and about 500 mM, in the cryopreservation medium. In another embodiment of the present invention, the concentration of trehalose in the cryopreservation medium ranges from about 10 mM to less than about 100 mM, such as from about 10 mM to about 50 mM, in the cryopreservation medium. The concentration of the eukaryotic cells in the cryopreservation medium that will provide optimal results may vary, and the concentration selected for use in any given procedure will be governed primarily by consideration of economy and efficiency. Effective results will generally be achieved with suspensions containing from about $10^5$ to about $10^{10}$ eukaryotic cells per milliliter of cryopreservation medium, preferably from about $10^6$ to about $10^9$ eukaryotic cells/mL, and most preferably from about $10^7$ to about $10^8$ eukaryotic cells/mL.

The amount of the preferred trehalose loaded inside the eukaryotic cells may be any suitable amount, preferably from about 10 mM to less than about 100 mM, more preferably from about 10 mM to about 90 mM, most preferably from about 10 mM to about 50 mM, and is preferably achieved by incubating the eukaryotic cells to preserve biological properties during freeze-drying with a trehalose solution that has less than about 100 mM trehalose therein. As was found for platelets, higher concentrations of trehalose during incubation are not preferred. The effective loading of trehalose is also accomplished by means of using an elevated temperature of from greater than about 25° C. to less than about 50° C., more preferably from about 30° C. to less than about 40° C., most preferably about 35° C. This is due to the discovery of the second phase transition for eukaryotic cells. It is believed that the trehalose loading efficiency for eukaryotic cells increase at incubation temperatures above about 25° C. up to about 50° C. Thus, it is believed that the FIG. 1 graph for platelets would be applicable for eukaryotic cells when the steep upwardly sloping line in FIG. 1 is extended to an incubation temperature of about 50° C.

The trehalose concentration in the exterior solution (that is, the loading buffer or cryopreservation medium) and the temperature during incubation together lead to a trehalose uptake that occurs primarily through fluid phase endocytosis (i.e., pinocytosis). Pinocytosed vesicles lyse over time which results in a homogeneous distribution of trehalose in the eukaryotic cells. Without being limited by theory, while we believe that pinocytosis is involved, it may be that the second phase transition itself stimulates the pinocytosis at high temperatures. It is believed that other oligosaccharides when loaded in this second phase transition in amounts analogous to trehalose could have similar effects. It is also believed that the trehalose loading efficiency as a function of incubation time for eukaryotic cells would be comparable to that of platelets. Thus, FIG. 2 would be representative of the trehalose loading efficiency as a function of incubation time for eukaryotic cells.

Lipid phase transitions in the eukaryotic cells are preferably measured by changes in membrane $CH_2$ vibrational frequency, using a Fourier transform infrared microscope coupled to an optical bench and equipped with a temperature controller. Samples may be prepared by placing the eukaryotic cells between $CaF_2$ windows, and placing the windows and eukaryotic cells in the temperature controller on the microscope stage. All curve fitting may be done by multiple iterations of a least squares algorithm on a microcomputer.

In preparing particularly preferred embodiments of the invention, eukaryotic cells may be loaded with trehalose by incubation at about 37° C. from about four to about twenty-four hours. The trehalose concentration in the loading buffer or cryopreservation medium is preferably about 35 mM, which results in an intracellular trehalose concentration of around 20 mM, but in any event is most preferably not greater than about 50 mM trehalose. At trehalose concentrations below about 50 mM, eukaryotic cells have a normal morphological appearance.

After the eukaryotic cells have been effectively loaded with a preservative (e.g., an oligosaccharide, such as trehalose), then the loading buffer or cryopreservation medium is removed and the eukaryotic cells are contacted with a drying buffer (i.e., a freeze-drying buffer). Drying of eukaryotic cells after preservative loading may be carried out by suspending the eukaryotic cells in a suitable drying solution containing a suitable bulking agent (or drying buffer), such as in any suitable drying solution containing a salt, a starch, or an albumin. The drying buffer preferably also includes the preservative (e.g., trehalose), preferably in amounts up to about 200 mM, more preferably up to about 100 mM. Trehalose in the drying buffer assists in spatially separating the eukaryotic cells as well as stabilizing the eukaryotic membranes on the exterior. The drying buffer preferably also includes a bulking agent (to further separate the eukaryotic cells). As previously indicated, albumin may serve as a bulking agent, but other polymers may be used with the same effect. Suitable other polymers, for example, are water-soluble polymers such as HES and dextran.

The preservative (trehalose) loaded eukaryotic cells in the drying buffer are then cooled to a temperature below about −32° C. A cooling (i.e. freezing) rate is preferably between −30° C. and −1° C./min., and more preferably between about −2° C./min to −5° C./min. The lyophilization step is preferably conducted at a temperature below about −32° C., for example conducted at about −40° C.

In one embodiment of the present invention, drying may be continued until about 95 weight percent of water has been removed from the eukaryotic cells. During the initial stages of lyophilization, the pressure is preferably at about $10 \times 10^{-6}$ Torr. As the cell samples dry, the temperature may be raised to be warmer than −32° C. Based upon the bulk of the cell samples, the temperature, and the pressure, it may be empirically determined what the most efficient temperature values should be in order to maximize the evaporative water loss. For this embodiment of the invention, freeze-dried eukaryotic cell compositions may have less than about 5 weight percent water.

In another embodiment of the invention, drying of the eukaryotic cells is continued until the water content of the eukaryotic cells does not fall below about 0.15 grams of water per gram of dry weight eukaryotic cells, more preferably not below about 0.20 grams of water per gram of dry weight eukaryotic cells. Preferably, the water content of the dried (e.g., freeze-dried) eukaryotic cells is maintained from about 0.20 gram of residual water per gram of dry weight eukaryotic cells to about 0.75 gram of residual water per gram of dry weight eukaryotic cells. For this embodiment of the invention, dehydration does not mean removal of 100% contained water. It has been discovered that by retention of greater than 0.15 gm water per gm dry weight eukaryotic cells, the survival percentage of the eukaryotic cells after removal from the lyophilizer and rehydration is more than about 80%.

Figure 22A:
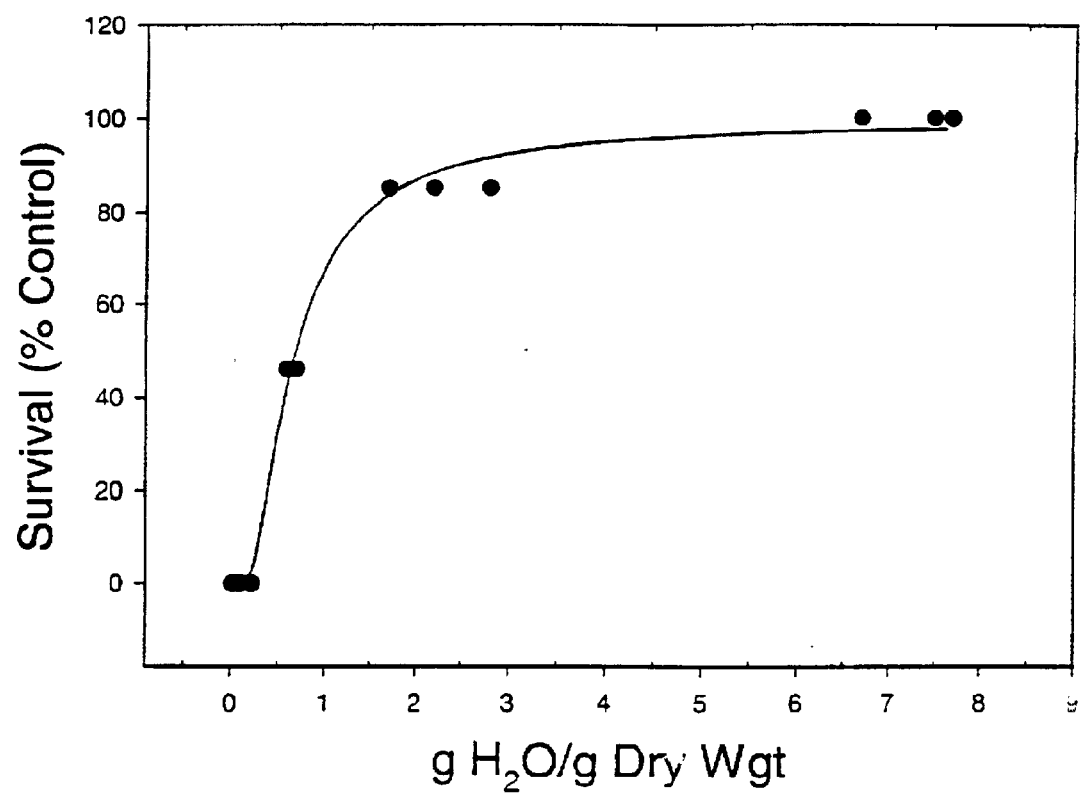
FIG. 22A is a graph of cell survival (% control) of trehalose loaded epithelial 293H cells as a function of residual water content measured by trypan blue exclusion.
Figure 22B:
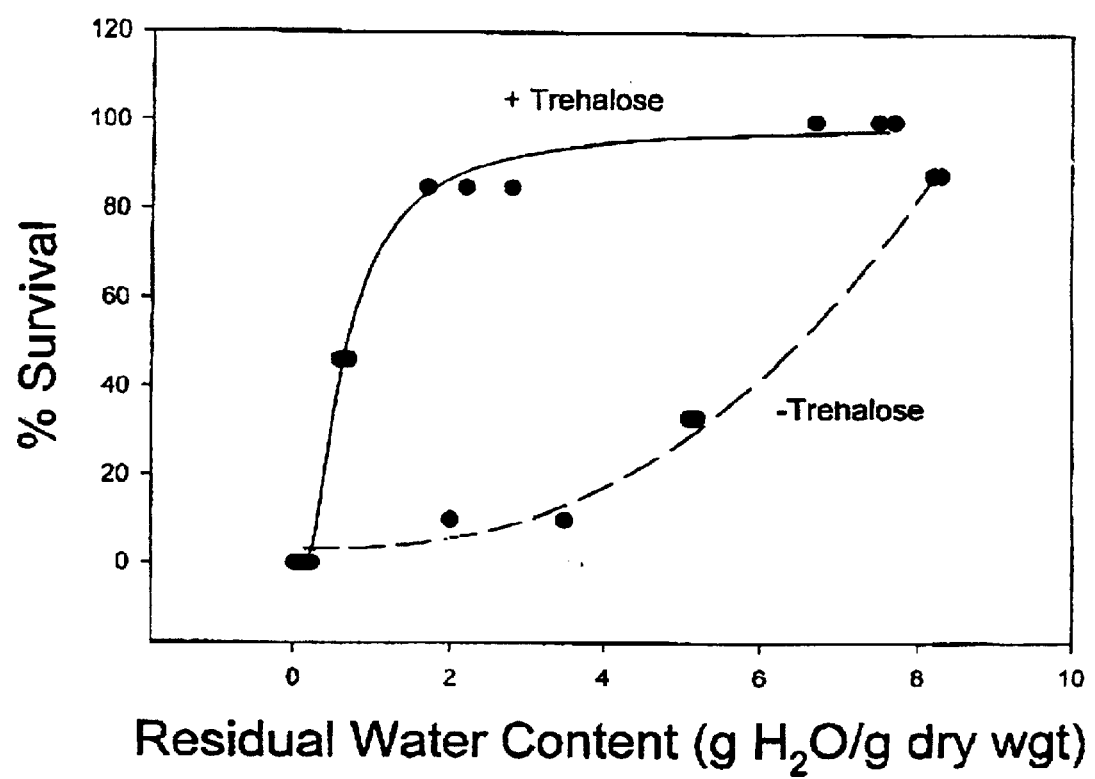
FIG. 22B is another graph of cell survival (% control) of trehalose loaded epithelial 293H cells as a function of residual water content measured by trypan blue exclusion.
Figure 23:
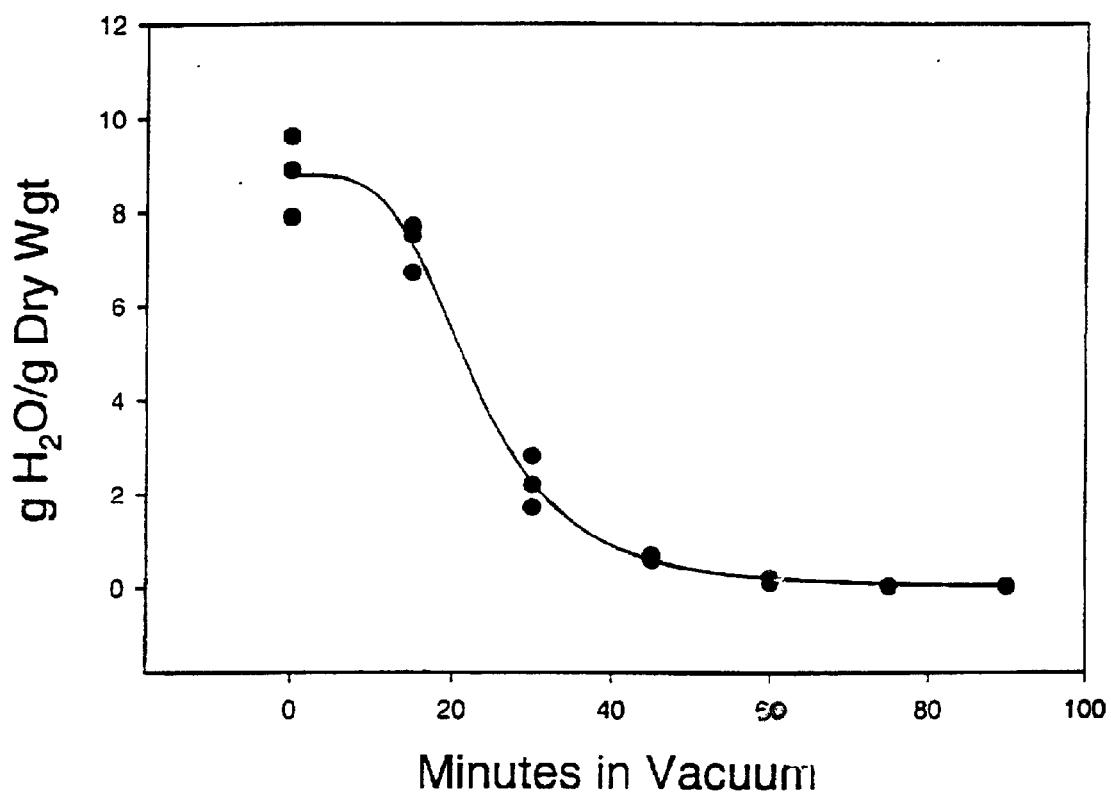
FIG. 23 is a graph of the residual water content of epithelial 293H cells versus time (minutes) during freeze-drying in a vacuum.

Referring now to FIG. 22A there is seen a graph of cell survival (% control) for trehalose loaded epithelial 293H cells as a function of residual water content measured by trypan blue exclusion. FIG. 22A clearly shows that for residual water contents greater than about 0.15 gram of residual water per gram of dry weight eukaryotic cells, cell survival is high (e.g., greater than about 80%), but descends toward zero (0) if less than about 0.15 grams of water per gram of dry weight eukaryotic cells is retained. FIG. 22B is another graph of cell survival (% control) of trehalose loaded epithelial 293H cells as a function of residual water content measured by trypan blue exclusion. FIG. 23 is a graph of the water content of epithelial 293H cells vs. time (minutes) of vacuum drying. The results illustrated in FIG.

23 were obtained by loading the epithelial 293H cells with trehalose, then cooling and freezing, and subsequently transferring the cells to a side arm lyophilizer, which permitted selective removal of cell samples one at a time during the freeze-drying process. The cell samples were removed at the indicated time intervals, weighed, and then oven dried to constant weight. The water content at each time point shown in FIG. 23 was calculated from the wet (or water) weight-dry weight difference. The freeze-dried eukaryotic cell compositions for this embodiment of the invention have more than about 0.15 gram of residual water per gram of dry weight eukaryotic cells.

As was seen for the freeze-dried platelets, the freeze-dried eukaryotic cells, whether by themselves, as a component of a vial-compatible structure or matrix, may be packaged so as to prevent rehydration until desired. As previously indicated for platelets, the packaging may be any of the various suitable packaging for therapeutic purposes, such as made from foil metallized plastic materials, and moisture barrier plastics (e.g. high-density polyethylene or plastic films that have been created with materials such as SiOx), cooling the preservative (trehalose) loaded eukaryotic cells to below their freezing point, and lyophilizing the cooled eukaryotic cells. The trehalose loading preferably includes incubating the eukaryotic cells at a temperature from greater than about 25° C. to less than about 50° C. with a trehalose solution having up to about 50 mM trehalose therein. The process of using such a dehydrated cell composition comprises rehydrating the eukaryotic cells, which may be with any suitable aqueous solution, such as water. As previously indicated for platelets, the rehydration preferably includes a prehydration step sufficient to bring the water content of the freeze-dried eukaryotic cells to between 35 weight percent to about 50 weight percent.

When reconstitution is desired, prehydration of the freeze-dried eukaryotic cells in moisture saturated air followed by rehydration is preferred. Use of prehydration yields eukaryotic cells with much more dense appearance and with no balloon eukaryotic cells being present. Prehydrated previously lyophilized eukaryotic cells resemble fresh eukaryotic cells after rehydration. This is illustrated, for example, by FIGS. 16C, 17A and 17B. As can be seen in these figures, previously freeze-dried eukaryotic cells can be restored to a viable condition having an appearance of fresh eukaryotic cells.

Prehydration is preferably conducted in moisture saturated air, most preferably prehydration is conducted at about 37° C. for about one hour to about three hours. The preferred prehydration step brings the water content of the freeze-dried eukaryotic cells to between about 20 weight percent to about 50 weight percent. The prehydrated eukaryotic cells may then be fully rehydrated. Rehydration may be with any aqueous based solutions (e.g., water), depending upon the intended application.

In additional embodiments of the present invention, it has been further discovered that many of the general findings with respect to platelets and eukaryotic cells are broadly applicable to erythrocytic cells. The term "erythrocytic cell" is used to mean any red blood cell. Mammalian, particularly human, erythrocytes are preferred. Suitable mammalian species for providing erythrocytic cells include by way of example only, not only human, but also equine, canine, feline, or endangered species.

The erythrocytic cells preferably contain an alcohol, more preferably an alcohol in a concentration ranging from about 10 wt. % to about 50 wt. %. In a preferred embodiment of the invention, the alcohol comprises a sterol, preferably a steroid alcohol containing the common steroid nucleus, plus an 8 to 10-carbon-atom side-chain and a hydroxyl group. It is known that sterols are widely distributed in plants and animals, both in the free form and esterified to fatty acids. Preferably, the steroid alcohol contained in the erythrocytic cells comprises cholesterol (cholesterin: 5-cholesten-3-β-ol), $C_{27}H_{45}OH$, in a concentration ranging from about 10 wt. % to about 50 wt. %.

Cholesterol is an important mammalian (i.e., animal) sterol. Cholesterol is also the most common animal sterol, a monohydric secondary alcohol of the cyclopentenophenanthrene (4-ring fused) system, containing one double bond. It occurs in part as the free sterol and in part esterified with higher fatty acids as a lipid in human blood serum. The primary precursor in biosynthesis appears to be acetic acid or sodium acetate. It is known that cholesterol in the mammalian system is the precursor of bile acids, steroid hormones, and provitamin D3.

In a preferred embodiment of the invention, the erythrocytic cells comprise from about 10 wt. % to about 50 wt. % cholesterol having the following formula:

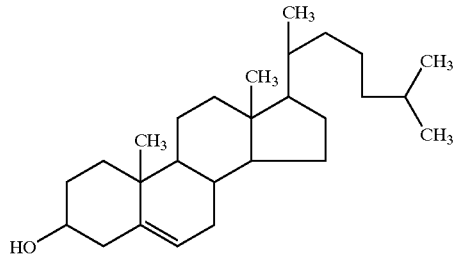

Thus, further compositions and further embodiments of the present invention include erythrocytic cells that have been manipulated (e.g., by freeze-drying) or modified (e.g., loaded with preservatives) and that are useful for well known therapeutic applications. We have discovered that alcohol-containing erythrocyte cells include alcohol-containing erythrocyte membranes, and have two phase transition temperature ranges, more specifically two weakly membranes, and have two phase transition temperature ranges, more specifically two weakly cooperative phase transition temperature ranges respectively having a temperature range ranging from about 7° C. to about 21° C. (e.g., about 14.4° C.±1.3° C.) and from about 25° C. to about 44° C. (e.g., about 34.2° C.±1.4° C.). We have also discovered that removing at least part of the alcohol (e.g., a steroid alcohol, such as cholesterol) from the erythrocyte cells including the erythrocyte membranes results in an increase in the cooperativity of the two phase transition temperature ranges, as well as a formation of a third or intermediate phase temperature range. More specifically, we have discovered that after removal of at least about 10% by wt. of cholesterol, more preferably at least about 30% by wt. of cholesterol, alcohol reduced (i.e., sterol reduced) erythrocytic cells are produced preferably having from about 20% by weight to about 40% by weight alcohol, more preferably from about 20% by weight to about 30% by weight alcohol (e.g., cholesterol).

The alcohol or sterol reduced erythrocytic cells have a first or low phase transition temperature range greater than about 2° C., an intermediate phase temperature range greater than about 20° C., and a high phase transition temperature range greater than about 30° C. Preferably, the low phase transition temperature range ranges from a temperature greater than about 2° C. to a temperature less than or equal to about 20° C. (e.g., from about 12° C. to about 18° C., such as about 15.3° C.±about 0.8° C.), the intermediate phase transition temperature range ranges from a temperature greater than about 20° C. to a temperature less than or equal to about 30° C. (e.g., from about 23° C. to about 29° C., such as about 26.0° C.±about 0.8° C.), and the high phase transition temperature range ranges from a temperature greater than about 30° C. to a temperature less than or equal to about 50° C. (e.g., from about 30° C. to about 40° C., or from about 32° C. to about 38° C., such as about 35.4° C.±about 1.5° C.).

Our discovery of at least three phase transition temperature ranges, including increasing the cooperativity of the phase transitions, for the alcohol-reduced erythrocytic cells and erythrocytic membranes suggests improving the preservation of erythrocytic cells by optimizing loading erythrocytic cells with a preservative (e.g., an oligosaccharide, such as trehalose), and by optimizing the storage and rehydration of erythrocytic cells. Fundamental knowledge about membrane phase (i.e., phospholipid) transition temperatures is of practical importance for determining the in vitro storage conditions of erythrocytes in blood banks. We anticipate that preferably a temperature within the high phase transition temperature range (e.g., a temperature about 34° C.) can be used to load erythrocytes with the oligosaccharide, such as trehalose, or any other lyoprotectant, and that intracellular preservative (e.g., a oligosaccharide including trehalose) allows the erythrocytes to survive freeze-drying. Freeze-dried erythrocytic cells will find broad applications in the field of medicine, pharmaceuticals, and biotechnology.

As was previously indicated for eukaryotic cells, one of the salient components for compositions and apparatus of additional embodiments of the present invention, when cell preservation will be assisted by freeze-drying, is the oligosaccharide, preferably trehalose, because we have discovered that alcohol-reduced erythrocytic cells which are effectively loaded with trehalose preserve biological properties during freeze drying (and rehydration). This preservation of biological properties, such as the immediate restoration of viability following rehydration, is necessary so that the erythrocytic cells following preservation can be successfully used in a variety of well known therapeutic applications. Preferably, the preparation of preserved erythrocytic cells in accordance with embodiments of the present invention broadly comprises the steps of providing a source of erythrocytic cells having an alcohol (e.g., a steroid alcohol such as cholesterol), removing at least a portion of the alcohol from the erythrocytic cells, loading the erythrocytic cells with a protective preservative (e.g., an oligosaccharide), cooling the loaded erythrocytic cells to below −32° C., and lyophilizing the cooled erythrocytic cells. In a preferred embodiment of the invention, the alcohol-reduced erythrocytic cells including erythrocytic membranes, comprise the three phase transition temperature ranges, and are loaded with the protective preservative at a temperature within one of the three phase transition temperature ranges. In erythrocytes from some species, it may not be necessary to remove any alcohol.

As was previously mentioned for eukaryotic cells, the source of the erythrocytic cells may be any suitable source. Regardless of the source of the erythrocytic cells, obtained erythrocytic cells typically comprise an alcohol, more preferably sterol, or a steroid alcohol such as cholesterol, at least a portion of which is to be removed to produce alcohol-reduced, more specifically, steroid/steroid alcohol-reduced or cholesterol-reduced erythrocytic cells having at least the three phase transition temperature ranges. The alcohol (e.g., cholesterol) may be removed from the erythrocytic cells/membranes by any suitable means or by any suitable manner. In a preferred embodiment of the invention, the alcohol is removed by incubating the erythrocytic cells, preferably incubating in an alcohol-removing medium containing an alcohol-removing agent. More preferably, especially when the alcohol comprises cholesterol, the erythrocytic cells are incubated at a temperature ranging from about 25° C. to about 50° C., more preferably from about 34° C. to about 40° C., for a suitable time period (e.g., from 10 minutes to about three hours) in the presence of the cholesterol-removing medium containing a cholesterol-removing agent.

In a preferred embodiment of the invention, the cholesterol-removing medium comprises a buffer containing from about 1 mM to about 10 mM, preferably from about 1 mM to about 5 mM, of methyl-β-cyclodextrin (MβCD). The spirit and scope of the present invention includes not only MβCD as the cholesterol-removing agent, but also any other cholesterol-removing agent for assisting in the removal of cholesterol from the erythrocytes including the erythrocytic membranes. In a preferred embodiment of the invention, after at least a portion of the cholesterol has been removed, the cholesterol-reduced erythrocytic cells/membranes preferably comprise from about 10 wt. % to about 50 wt. % cholesterol, more preferably from about 10 wt. % to about 30 wt. % cholesterol, most preferably from about 20 wt. % to about 30 wt. %.

The alcohol-reduced erythrocytic cells are preferably loaded by incubating the alcohol-reduced erythrocytic cells in a buffer. The preservative (e.g., an oligosaccharide, such as trehalose) is preferably dissolved in the buffer, which includes any liquid solution capable of preserving living cells and tissue. Many types of buffers are known in the literature and available from any of the previously mentioned commercial suppliers for short term incubation of erythrocytes.

As was seen for nucleated cells, when the preservative to be loaded in the alcohol-reduced erythrocytic cells is trehalose, the actual amount of trehalose dissolved in the buffer may vary, although considerations of the economical use of materials and labor, and considerations of the cryopreservation protocol, i.e., the choice of procedural steps used for cooling and thawing the alcohol-reduced erythrocytic cells together with the cooling and thawing rates, may affect the selection of concentration ranges that will provide the most efficient and effective preservation. In the case of trehalose for one embodiment of the present invention, the concentration of trehalose in the cryopreservation medium (i.e., the buffer plus added trehalose) ranges from about 10 mM and about 1.5 M, preferably between about 100 mM and about 500 mM, in the cryopreservation medium. In another embodiment of the present invention, the concentration of trehalose in the cryopreservation medium ranges from about 10 mM to less than about 100 mM, such as from about 10 mM to about 50 mM, in the cryopreservation medium. The concentration of the alcohol-reduced erythrocytic cells in the cryopreservation medium that will provide optimal results may vary, and the concentration selected for use in any given procedure will be governed primarily by consideration of economy and efficiency. Effective results will generally be achieved with suspensions containing from about $10^5$ to about $10^{10}$ alcohol-reduced erythrocytic cells per milliliter of cryopreservation medium, preferably from about $10^6$ to about $10^9$ alcohol-reduced erythrocytic cells/mL, and most preferably from about $10^7$ to about $10^8$ alcohol-reduced erythrocytic cells/mL.

The amount of the preferred trehalose loaded inside the alcohol-reduced erythrocytic cells may be any suitable amount, preferably from about 10 mM to less than about 200 mM, more preferably from about 10 mM to about 150 mM, most preferably from about 10 mM to about 100 mM, and is preferably achieved by incubating the alcohol-reduced erythrocytic cells to preserve biological properties during freeze-drying with a trehalose solution that has less than about 200 mM trehalose therein. As was found for platelets and eukaryotic cells, higher concentrations of trehalose during incubation are not preferred. The effective loading of trehalose is also accomplished by means of using a temperature that falls within one of the phase transition temperature ranges, preferably a temperature greater than about 30° C., more preferably temperature ranging from about 30° C. to less than about 50° C., most preferably from about 32° C. to less than about 38° C., most preferably about 34° C. This is due to the discovery of the intermediate and high phase transition temperature ranges for alcohol-reduced erythrocytic cells/membranes. It is believed that the trehalose loading efficiency for alcohol-reduced erythrocytic cells increase at incubation temperatures equal to or above about 30° C. up to about 50° C. Thus, it is believed that the FIG. 1 graph for platelets would be applicable for erythrocytic cells when the steep upwardly sloping line in FIG. 1 is extended to an incubation temperature of about 50° C.

The trehalose concentration in the exterior solution (that is, the loading buffer or cryopreservation medium) and the temperature during incubation together lead to a trehalose uptake that occurs primarily through defects that occur during the lipid phase transitions. Without being limited by theory, while we believe that pinocytosis is involved, it may be that the intermediate and/or high phase transition temperatures stimulate the pinocytosis. It is believed that other oligosaccharides when loaded in this intermediate and/or high phase transition temperatures in amounts analogous to trehalose could have similar effects. Pinocytosed vesicles lyse over time which results in a homogeneous distribution of trehalose in the erythrocytic cells. It is also believed that the trehalose loading efficiency as a function of incubation time for erythrocytic cells would be comparable to that of platelets and eukaryotic cells. Thus, FIG. 2 would be representative of the trehalose loading efficiency as a function of incubation time for erythrocytic cells.

As was performed for lipid phase transitions in eukaryotic cells, lipid phase transitions in the alcohol-reduced erythrocytic cells are preferably measured by changes in membrane CH2 vibrational frequency, using the Fourier transform infrared microscope coupled to an FTIR optical bench equipped with the temperature controller.

In preparing particularly preferred embodiments of the invention, alcohol-reduced erythrocytic cells/membranes may be loaded with trehalose by incubation at about 37° C. for about twenty-four hours. The trehalose concentration in the loading buffer or cryopreservation medium is preferably about 35 mM, which results in an intracellular trehalose concentration of around 20 mM, but in any event is most preferably not greater than about 50 mM trehalose. At trehalose concentrations below about 50 mM, alcohol-reduced erythrocytic cells have a normal morphological appearance.

After the alcohol-reduced erythrocytic cells have been effectively loaded with a preservative or protectant (e.g., an oligosaccharide, such as trehalose), then the loading buffer or cryopreservation medium is removed and the alcohol-reduced erythrocytic cells are contacted with a drying buffer (i.e., a freeze-drying buffer). Drying of alcohol-reduced erythrocytic cells after preservative loading may be carried out by suspending the alcohol-reduced erythrocytic cells in a suitable drying solution containing a suitable water replacing molecule, such as trehalose and a bulking agent such as a salt, a starch, or an albumin. The drying buffer preferably also includes the preservative (e.g., trehalose), preferably in amounts up to about 200 mM, more preferably up to about 100 mM. Trehalose in the drying buffer assists in spatially separating the alcohol-reduced erythrocytic cells as well as stabilizing the alcohol-reduced erythrocytic membranes on the exterior. The drying buffer preferably also includes a bulking agent (to further separate the alcohol-reduced erythrocytic cells). As previously indicated for eukaryotic cells, albumin may serve as a bulking agent, but other polymers may be used with the same effect. Suitable other polymers, for example, are water-soluble polymers such as HES and dextran.

The preservative (trehalose) loaded alcohol-reduced erythrocytic cells in the drying buffer are then cooled to a temperature below about $-32°$ C. A cooling (i.e. freezing) rate is preferably between $-30°$ C. and $-1°$ C./min., and more preferably between about $-2°$ C./min to $-5°$ C./min. The lyophilization step is preferably conducted at a temperature below about $-32°$ C., for example conducted at about $-40°$ C.

In one embodiment of the present invention, drying may be continued until about 95 weight percent of water has been removed from the alcohol-reduced erythrocytic cells. During the initial stages of lyophilization, the pressure is preferably at about $10 \times 10^{-6}$ Torr. As the cell samples dry, the temperature may be raised to be warmer than $-32°$ C. Based upon the bulk of the cell samples, the temperature, and the pressure, it may be empirically determined what the most efficient temperature values should be in order to maximize the evaporative water loss. For this embodiment of the invention, freeze-dried alcohol-reduced erythrocytic cell compositions may have less than about 5 weight percent water.

In another embodiment of the invention, drying of the alcohol-reduced erythrocytic cells is continued until the water content of the alcohol-reduced erythrocytic cells is equal to or less than about 0.30 grams of water per gram of dry weight alcohol-reduced erythrocytic cells, more preferably equal to or less than about 0.20 grams of water per gram of dry weight alcohol-reduced erythrocytic cells. Preferably, the water content of the dried (e.g., freeze-dried) alcohol-reduced erythrocytic cells is maintained from about 0.00 gram, preferably from about 0.05 gram, of residual water per gram of dry weight alcohol-reduced erythrocytic cells to about 0.20 gram of residual water per gram of dry weight alcohol-reduced erythrocytic cells. For this embodiment of the invention, dehydration does not necessarily mean removal of 100% contained water. It has been discovered that by retention of at least about 0.3 gm of water per gm dry weight alcohol-reduced erythrocytic cells optimizes survival percentage of the alcohol-reduced erythrocytic cells after removal from the lyophilizer and rehydration is substantially increased.

As was seen for the freeze-dried platelets and freeze-dried eukaryotic cells, the freeze-dried alcohol-reduced erythrocytic cells, whether by themselves, as a component of a vial-compatible structure or matrix, may be packaged so as to prevent rehydration until desired. As previously indicated for platelets and eukaryotic cells, the packaging may be any of the various suitable packaging for therapeutic purposes, such as made from foil metallized plastic materials, and moisture barrier plastics (e.g. high-density polyethylene or plastic films that have been created with materials such as SiOx), cooling the preservative (trehalose) loaded alcohol-reduced erythrocytic cells to below their freezing point, and lyophilizing the cooled alcohol-reduced erythrocytic cells. As was further previously indicated for platelets and eukaryotic cells, the trehalose loading preferably includes incubating the alcohol-reduced erythrocytic cells at a temperature from greater than about 25° C. to less than about 50° C. with a trehalose solution having up to about 50 mM trehalose therein. The process of using such a dehydrated cell composition comprises rehydrating the alcohol-reduced erythrocytic cells, which may be with any suitable aqueous solution, such as water. As previously mentioned for platelets and eukaryotic cells, the rehydration preferably includes a prehydration step sufficient to bring the water content of the freeze-dried alcohol-reduced erythrocytic cells to between about 20 weight percent to about 50 weight percent, preferably between about 20 weight percent and about 40 weight percent.

When reconstitution is desired, prehydration of the freeze-dried alcohol-reduced erythrocytic cells in moisture saturated air followed by rehydration is preferred. Use of prehydration yields alcohol-reduced erythrocytic cells with much more dense appearance and with no balloon alcohol-reduced erythrocytic cells being present. Prehydrated previously lyophilized alcohol-reduced erythrocytic cells resemble fresh erythrocytic cells after rehydration.

Prehydration is preferably conducted in moisture saturated air, most preferably prehydration is conducted at about 37° C. for about one hour to about three hours. The preferred prehydration step brings the water content of the freeze-dried alcohol-reduced erythrocytic cells to between about 20 weight percent to about 40 weight percent. The prehydrated alcohol-reduced erythrocytic cells may then be fully rehydrated. Rehydration may be with any aqueous based solutions (e.g., water), depending upon the intended application.

Embodiments of the present invention will be illustrated by the following set forth examples which are being given to set forth the presently known best mode and by way of illustration only and not by way of any limitation. All parameters such as concentrations, mixing proportions, temperatures, rates, compounds, etc., submitted in these examples are not to be construed to unduly limit the scope of the invention. Abbreviations used in the examples, and elsewhere, are as follows.

DMSO=dimethylsulfoxide
ADP=adenosine diphosphate
PGE1=prostaglandin E1
HES=hydroxy ethyl starch
FTIR=Fourier transform infrared spectroscopy
EGTA=ethylene glycol-bis(2-aminoethyl ether) N,N,N', N', tetra-acetic acid
TES=N-tris (hydroxymethyl) methyl-2-aminoethanesulfonic acid
HEPES=N-(2-hydroxyl ethyl) piperarine-N'-(2-ethanesulfonic acid)
PBS=phosphate buffered saline
HSA=human serum albumin
BSA=borine serum albumin
ACD=citric acid, citrate, and dextrose
MβCD=methyl-β-cyclodextrin

EXPERIMENTAL

EXAMPLE 1

Washing of Platelets. Platelet concentrations were obtained from the Sacramento blood center or from volunteers in our laboratory. Platelet rich plasma was centrifuged for 8 minutes at 320 x g to remove erythrocytes and leukocytes. The supernatant was pelleted and washed two times (480 x g for 22 minutes, 480 x g for 15 minutes) in buffer A (100 mM NaCl, 10 mM KCl, 10 mM EGTA, 10 mM imidazole, pH 6.8). Platelet counts were obtained on a Coulter counter T890 (Coulter, Inc., Miami, Fla).

Loading of Lucifer Yellow CH into Platelets. A fluorescent dye, lucifer yellow CH (LYCH), was used as a marker for penetration of the membrane by a solute. Washed platelets in a concentration of $1-2\times10^9$ platelets/ml were incubated at various temperatures in the presence of 1–20 mg/ml LYCH. Incubation temperatures and incubation times were chosen as indicated. After incubation the platelets suspensions were spun down for 20 x at 14,000 RPM (table centrifuge), resuspended in buffer A, spun down for 20 s in buffer A and resuspended. Platelet counts were obtained on a Coulter counter and the samples were pelleted (centrifugation for 45 s at 14,000 RPM, table centrifuge). The pellet was lysed in 0.1% Triton buffer (10 mM TES, 50 mM KCl, pH 6.8). The fluorescence of the lysate was measured on a Perkin-Elmer LSS spectrofluorimeter with excitation at 428 nm (SW 10 nm) and emission at 530 nm (SW 10 nm). Uptake was calculated for each sample as nanograms of LYCH per cell using a standard curve of LYCH in lysate buffer. Standard curves of LYCH, were found to be linear up to 2000 nm ml$^{-1}$.

Visualization of cell-associated Lucifer Yellow. LYCH loaded platelets were viewed on a fluorescence microscope (Zeiss) employing a fluorescein filter set for fluorescence microscopy. Platelets were studied either directly after incubation or after fixation with 1% paraformaldehyde in buffer. Fixed cells were settled on poly-L-lysine coated cover slides and mounted in glycerol.

Loading of Platelets with Trehalose. Washed platelets in a concentration of 1–2 $10^9$ platelets/ml were incubated at various temperatures in the presence of 1–20 mg/ml trehalose. Incubation temperatures were chosen from 4° C. to 37° C. Incubation times were varied from 0.5 to 4 hours. After incubation the platelet solutions were washed in buffer A two times (by centrifugation at 14,000 RPM for 20 s in a table centrifuge). Platelet counts were obtained on a coulter counter. Platelets were pelleted (45 S at 14,000 RPM) and sugars were extracted from the pellet using 80% methanol. The samples were heated for 30 minutes at 80° C. The methanol was evaporated with nitrogen, and the samples were kept dry and redissolved in $H_2O$ prior to analysis. The amount of trehalose in the platelets was quantified using the anthrone reaction (Umbreit et al., *Mamometric and Biochemical Techniques*, 5$^{th}$ Edition, 1972). Samples were redissolved in 3 ml $H_2O$ and 6 ml anthrone reagents (2 g anthrone dissolved in 10 M sulfuric acid). After vortex mixing, the samples were placed in a boiling water bath for 3 minutes. Then the samples were cooled on ice and the absorbance was measured at 620 nm on a Perkin Elmer spectrophotometer. The amount of platelet associated trehalose was determined using a standard curve of trehalose. Standard curves of trehalose were found to be linear from 6 to 300 μg trehalose per test tube.

Quantification of Trehalose and LYCH Concentration. Uptake was calculated for each sample as micrograms of trehalose or LYCH per platelet. The internal trehalose concentration was calculated assuming a platelet radius of 1.2 μm and by assuming that 50% of the platelet volume is taken up by the cytosol (rest is membranes). The loading efficiency was determined from the cytosolic trehalose or LYCH concentration and the concentration in the loading buffer.

FIG. 1 shows the effect of temperature on the loading efficiency of trehalose into human platelets after a 4 hour incubation period with 50 mM external trehalose. The effect of the temperature on the trehalose uptake showed a similar trend as the LYCH uptake. The trehalose uptake is relatively low at temperatures of 22° C. and below (below 5%), but at 37° C. the loading efficiency of trehalose is 35% after 4 hours.

When the time course of trehalose uptake is studied at 37° C., a biphasic curve can be seen (FIG. 2). The trehalose uptake is initially slow ($2.8 \times 10^{-11}$ mol/m$^2$s from 0 to 2 hours), but after 2 hours a rapid linear uptake of $3.3 \times 10^{-10}$ mol/m$^2$s can be observed. The loading efficiency increases up to 61% after an incubation period of 4 hours. This high loading efficiency is a strong indication that the trehalose is homogeneously distributed in the platelets rather than located in pinocytosed vesicles.

The uptake of trehalose as a function of the external trehalose concentration is shown in FIG. 3. The uptake of trehalose is linear in the range from 0 to 30 mM external trehalose. The highest internal trehalose concentration is obtained with 50 mM external trehalose. At higher concentrations than 50 mM the internal trehalose concentration decreases again. Even when the loading buffer at these high trehalose concentrations is corrected for isotonicity by adjusting the salt concentration, the loading efficiency remains low. Platelets become swollen after 4 hours incubation in 75 mM trehalose.

The stability of the platelets during a 4 hours incubation period was studied using microscopy and flow cytometric analysis. No morphological changes were observed after 4 hours incubation of platelets at 37° C. in the presence of 25 mM external trehalose. Flow cytometric analysis of the platelets showed that the platelet population is very stable during 4 hours incubation. No signs of microvesicle formation could be observed after 4 hours incubation, as can be judged by the stable relative proportion of microvesicle gated cells (less than 3%). The formation of microvesicles is usually considered as the first sign of platelet activation (Owners et al., Trans. *Med. Rev.*, 8, 27–44, 1994). Characteristic antigens of platelet activation include: glycoprotein 53 (gp53, a lysosomal membrane marker), PECAM-1 (platelet endothelial cell adhesion molecule-1, an alpha granule constituent), and P-selection (an alpha granule membrane protein).

EXAMPLE 2

Washing Platelets. Platelets were obtained from volunteers in our laboratory. Platelet rich plasma was centrifuged for 8 minutes at 320 x g to remove erythrocytes and leukocytes. The supernatant was pelleted and washed two times (480 x g for 22 minutes, 480 x g for 15 minutes) in buffer A (100 mM NaCl, 10 mM KCl, 10 mM EGTA, 10 mM imidazole, 10 μg/ml PGE1, pH 6.8). Platelet counts were obtained on a Coulter counter T890 (Coulter, Inc., Miami, Fla).

Loading Platelets with Trehalose. Platelets were loaded with trehalose as described in Example 1. Washed platelets in a concentration of 1–2×10$^9$ platelets/ml were incubated at 37° C. in buffer A with 35 mM trehalose added. Incubation times were typically 4 hours. The samples were gently stirred for 1 minute every hour. After incubation the platelet solutions were pelleted (25 sec in a microfuge) and resuspended in drying buffer (9.5 mM HEPES, 142.5 mM NaCl, 4.8 mM KCl, 1 mM MgCl$_2$, 30 mM Trehalose, 1% Human Serum Albumin, 10 μg/ml PGE1). In the aggregation studies no PGE1 was added in the drying buffer. Trehalose was obtained from Pfahnstiehl. Human serum albumin was obtained from Sigma.

Freezing and Drying. Typically 0.5 ml platelet suspensions were transferred in 2 ml Nunc cryogenic vials and frozen in a Cryomed controlled freezing device. Vials were frozen from 22° C. to −40° C. with freezing rates between −30 and −1° C./min and more often between −5 and −2° C./min. The frozen solutions were transferred to a −80° C. freezer and kept there for at least half an hour. Subsequently the frozen platelet suspensions were transferred in vacuum flasks that were attached to a Virtis lyophilizes. Immediately after the flasks were hooked up to the lyophilizer, they were placed in liquid nitrogen to keep the samples frozen until the vacuum returned to $20 \times 10^{-6}$ Torr, after which the samples were allowed to warm to the sublimation temperature. The condenser temperature was −45° C. Under these conditions, sample temperature during primary drying is about −40° C., as measured with a thermocouple in the sample. It is important to maintain the sample below $T_g$ for the excipient during primary drying (−32° C. for trehalose).

Rehydration. Vials with originally 0.5 ml platelet suspension were rehydrated in 1 ml PBS buffer/water (1/1). PBS buffer was composed of 9.4 mM Na$_2$HPO$_4$, 0.6 mM KH$_2$PO$_4$, 100 mM NaCl, pH 7.2). In a few experiments PGE1 was added to the rehydration buffer in a condition of 10 μg/ml or rehydration was performed in plasma/water (1/1).

Prehydration. Platelet lyophilisates were prehydrated in a closed box with moisture saturated air at 37° C. Prehydration times were between 0 and 3 hours.

Recovery. The numerical recovery of lyophilized and (p)rehydrated platelets was determined by comparing the cell count with a Coulter count T890 (Coulter, Inc., Miami, Fla.) before drying and after rehydration. The morphology of the rehydrated platelets was studied using a light microscope. For this purpose platelets were fixed in 2% paraformaldehyde or gutaraldehyde and allowed to settle on poly-L-lysine coated coverslides for at least 45 minutes. After this the coverslides were mounted and inspected under the microscope. The optical density of freeze-dried and rehydrated platelets was determined by measuring the absorbance of a platelet suspension of $1.0 \times 10^8$ cells/ml at 550 nm on a spectrophotometer.

Aggregation studies. Dried platelets were rehydrated (after 2 hour prehydration) with 2 aliquots of platelet free plasma (plasma was centrifuged for 5 minutes at 3800 x g) diluted with water in 1/1 ratio. Half ml aliquots of this platelet suspension were transferred to aggregation cuvettes with a magnetic stirrer. The response of the platelets to thrombin was tested by adding thrombin (1 U/ml) to the platelet suspension at 37° C. under stirring conditions. After 3 minutes thrombin treated platelet suspensions were inspected for clots and cell counts were done on a Coulter Counter T890.

Direct rehydration tends toward cell lysis and prehydration leads to aggregation when the cell concentration is 10$^9$ cells/ml in the drying buffer. We found also that recovery of prehydrated and rehydrated platelets depends on the cell concentration in the drying buffer. The recovery drops to very low values if the cell concentration is higher than $3 \times 10^8$ cells/ml. At concentrations below $3 \times 10^8$ cells/ml, the recovery is around 70%, and no aggregates were visible. Prehydration resulted in denser cells and the absence of balloon cells.

Longer prehydration times than 90 minutes did not further improve the cellular density, but slightly activated the platelets. The water content of the pellet increases with increasing prehydration time, and preferably is between about 35% and 50% at the moment of rehydration. At higher water contents than 50% water droplets become visible in the lyophilisate (which means that the platelets are in a very hypertonic solution).

As described by Example 1, platelets were loaded with trehalose by incubation at 37° C. for 4 hours in buffer A with 35 mM trehalose, which yielded platelets with intracellular trehalose concentration of 15–25 mM. After incubation, the platelets were transferred to drying buffer with 30 mM trehalose and 1% HSA as the main excipients.

The directly rehydrated platelets had a high numerical recovery of 85%, but a considerable fraction (25–50%) of the cells was partly lysed and had the shape of a balloon. Directly rehydrated platelets were overall less dense when compared with fresh platelets.

The numerical recovery of platelets that were prehydrated in moisture saturated air was only 25% when the platelet concentration was $1\times10^9$ cells/ml in the drying buffer. This low recovery was due to aggregates that were formed during the prehydration period. But the cells that were not aggregated were more dense than the directly rehydrated platelets and resembled that of fresh platelets.

Since it appears desirable to dilute the platelets to prevent aggregation during the prehydration step, it may be necessary for clinical applications to concentrate the platelets following rehydration. We therefore also tested the stability of the rehydrated platelets with respect to centrifugation and found that the directly rehydrated platelets had 50% recovery after centrifugation, while the prehydrated ones had 75% recovery following centrifugation. Thus, we conclude that the inventive platelets can be concentrated without ill effect.

EXAMPLE 3

We view trehalose as the main lyoprotectant in the drying buffer. However, other components in the drying buffer, such as albumin, can improve the recovery. In the absence of external trehalose in drying buffer, the numerical recovery is only 35%. With 30 mM trehalose in the drying buffer the recovery is around 65%. A combination of 30 mM trehalose and 1% albumin gave a numerical recovery of 85%.

EXAMPLE 4

Typically 0.5 ml platelet suspensions were transferred in 2 ml Nunc cryogenic vials and frozen in a Cryomed controlled freezing device. Vials were frozen from 22° C. to −40° C. with freezing rates between −30° C./min and −1° C./min and more often between −5° C. and −2° C./min. The frozen solutions were transferred to a −80° C. freezer and kept there for at least half an hour. Subsequently the frozen platelet suspensions were transferred in vacuum flasks that were attached to a Virtus lyophilizer. Immediately after the flasks were hooked up to the lyophilizer, they were placed in liquid nitrogen to keep the samples frozen until the vacuum returned to $20\times10^{-6}$ Torr, after which the samples were allowed to warm to the sublimation temperature. The condensor temperature was −45° C. Under these conditions, sample temperature during primary drying is about −40° C., as measured with a thermocouple in the sample. It is important to maintain the sample below $T_g$, for the excipient during primary drying (−32° C. for trehalose). Only minor differences in recovery were found as a function of the freezing rate. The optimal freezing rate was found to be between 2° C. and 5° C./minute.

EXAMPLE 5

Response of freeze-dried platelets to thrombin (1 U/ml) was compared with that of fresh platelets. The platelet concentration was $0.5\times10^8$ cells/ml in both samples. 500 μl platelets solution was transferred into aggregation vials. Thrombin was added to the samples and the samples were stirred for 3 minutes at 37° C. The cell counts that were determined after 3 minutes were 0 for both the fresh and the freeze-dried platelets. The response to thrombin was determined by a cleavage in glycoprotein lb-(GPlb). This was detected by using monoclonal antibodies and flow cytometry. Thus, the pattern seen after addition of thrombin was a reduced amount of GP lb on the platelet surface.

The response of lyophilized, prehydrated, and rehydrated platelets (Examples 1 and 2) to thrombin (1 U/ml) was found to be identical compared with that of fresh platelets. In both fresh and rehydrated platelets a clot was formed within 3 minutes at 37° C. These clots are illustrated by FIG. 8, panels (A) and (B). When cell counts were done with the Coulter counter, we found no cells present, indicating that all platelets participated in forming the clot illustrated in panel (B).

EXAMPLE 6

Reactions with other agonists were studied. Platelet suspensions of the inventive platelets were prepared with $50\times10^6$ platelets/ml. Different agonists were then added and subsequently counted with a Coulter counter to determine the percentage of platelets involved in the visually observable clot formation. The cell count was between 0 and $2\times10^6$ platelets/ml: after 5 minutes with 20 μg/ml collagen; after 5 minutes with 20 μM ADP; after 5 minutes with 1.5 mg/ml ristocetin This means that the percentage of platelets that are involved in clot formation is between 95–100% for all the agonists tested. The agonist concentrations that were used are all physiological. In all cases the percentage of clotted platelets was the same as fresh control platelets.

EXAMPLE 7

The procedures performed in this example were for mesennchymal stem cells, and illustrate cell culture, lipid phase transitions, cell loading, freeze-drying, rehydration and membrane phase transition.

Cell Culture. Mesenchymal stem cells (MSCs) supplied by Osiris Therapeutics were grown with Dulbecco's Modified Eagle's Medium (D-MEM) supplemented with 10% v/v fetal bovine serum (FBS) in T-185 Culture Flasks (Nalge-Nunc). Serum-supplemented cells were incubated at 37° C. and 5% $CO_2$.

Fourier Transform Infrared Spectroscopy. MSCs harvested by trypsinization were resuspended in 2 mL fresh medium, and the cells were allowed to settle for 30 min. The cell pellet was applied as a thin film between two $CaF_2$ windows and scanned by Fourier transform infrared (FTIR) spectroscopy on a Perkin Elmer Spectrum 2000. Data were collected from 3600 to 900 $cm^{-1}$ every 2° C. between −7 and 50° C. using a ramp rate of 2° C./min. Temperature was controlled by a Peltier device and monitored with a thermocouple attached directly to the sample windows.

Lucifer Yellow CH-Loading. MSCs were harvested by trypsinization, washed once and resuspended in fresh medium at a concentration of $5.7\times10^6$ cells/mL. Lucifer yellow CH (LYCH) was added to a concentration of 10.6 mM, and cells were tumbled in a flask at 37° C. for 3.5 hours. Aliquots of cells were removed at several time points and washed twice with DPBS. The pellet was split between two treatments. The fluorescence intensity of the cells was measured with a Perkin Elmer LS 50B luminescence spectrometer, using an excitation wavelength of 428 nm and an emission wavelength of 530 nm. In addition, cells from each time point were fixed in 1% paraformaldehyde, mounted on poly-L-lysine coated coverslips, and photographed with a Zeiss inverted fluorescent microscope, model ICM 405.

Freeze-Drying Flask Preparation. Freeze-drying flasks were prepared using Nalge-Nunc T-25 flasks modified for this purpose. These flasks have 0.22 $\mu$m filters to allow vapor transport without compromising sterility, and includes a thermocouple port to allow direct temperature measurement of the sample. Prior to freeze drying, the flasks were immersed in 70% ethanol to sterilize them after they were completely assembled. The flasks were then allowed to dry in a laminar flow hood.

Freeze-Drying. MSCs were initially loaded with trehalose by incubating them in medium supplemented with 90 mM trehalose for 24 hours. The cells were then harvested, washed and resuspended in freeze-drying buffer (130 mM NaCl, 10 mM HEPES (pH 7.2), 5 mM KCl, 150 mM trehalose, and 5.7% BSA (w/v)) to a final concentration of $0.5 \times 10^6$ cells/mL. This cell suspension was added in 2.5 mL aliquots to freeze-drying flasks and transferred to the Lyostar lyophilizer. The samples were frozen first at 5° C./min to 0° C., then at 2° C./min to −60° C. Once freeze-drying began, cells were maintained under vacuum at −30° C. for 180 minutes, then at −25° C. for 180 minutes. Finally, the cells were slowly ramped to room temperature over a 12-hour period under vacuum. With this protocol, the cells are freeze-dried in suspension, rather than as an attached culture.

Rehydration. Freeze-dried cells were rehydrated with a 1:3 mixture of $H_2O$ (equal to the original volume dried) and growth medium containing fetal bovine serum. This rehydration solution was either added directly to the lyophilizate or following a 45-min "prehydration" at 37° C. and 100% relative humidity. Micrographs were taken on a Zeiss inverted microscope using phase contrast or fluorescence modes using Kodak Ektachrome ASA 400 film.

Membrane Phase Transition. The membrane phase transition of hydrated MSCs was determined using FTIR spectroscopy, and FIG. 10 shows data sets for two independent experiments. The data points indicate the symmetric $CH_2$ stretching band position for each temperature, and the solid line shows the first derivative for one data set. Thus, FIG. 10 is more specifically a graph illustrating temperatures for membrane phase transition in hydrated mesenchymal stem cells by Fourier transform infrared (FTIR) spectroscopy, with the solid line graph indicating the first derivative of the set of data shown in filled circles. The peaks in the first derivative indicate the steepest regions in the band position vs. temperature plots that correspond to membrane phase transition temperatures. Two main transitions are evident at approximately 15 and 35° C., a pattern which has been observed in other cell types as well. This information enables characterization of the physical nature of the MSC membrane. The relationship between the phase transition in the hydrated and dry states (+/− trehalose) provides important information regarding the necessity and length of the prehydration protocol.

EXAMPLE 8

The procedures performed in this example were also for mesenchymal stem cells, and illustrate cell loading, cell growth, and freeze-drying.

Figure 11:
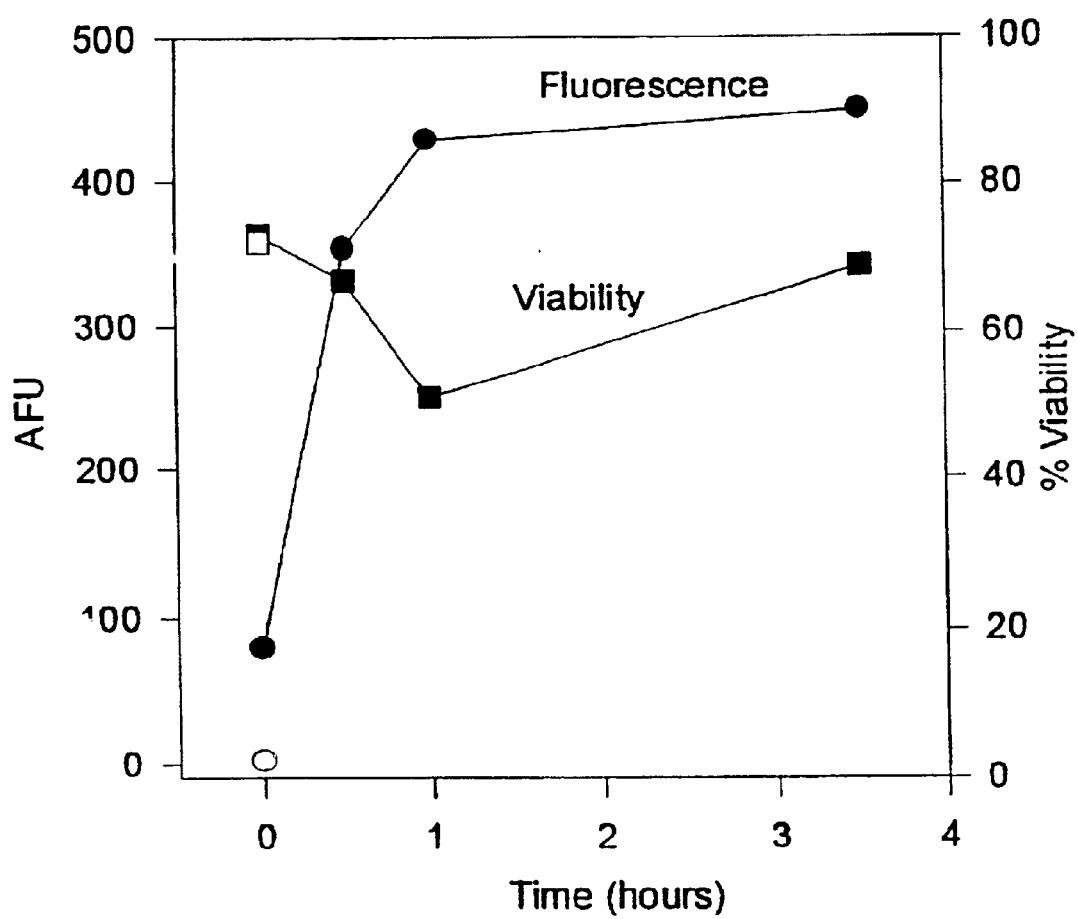
FIG. 11 is a graph representing LYCH loading of mesenchymal stem cells as monitored by fluorescence spectroscopy (filled circles points) and viability as monitored by trypan blue exclusion (filled squares points)

Lucifer Yellow-Loading. Mesenchymal stem cells were tested for their ability to take up solutes from the extracellular environment. The dye Lucifer yellow CH (LYCH) was used as a marker for this type of uptake as it is easily monitored, both by fluorescence spectroscopy and fluorescence microscopy. FIG. 11 is a graph representing LYCH loading of mesenchymal stem cells as monitored fluorescence spectroscopy (filled circles points) and viability as monitored trypan blue exclusion (filled squares points). The open symbols in FIG. 11 show fluorescence and viability data for control cells (no LYCH). FIG. 11 shows the progressive uptake of LYCH over a period of 3.5 hours as well as the viability (~70%), which was monitored in parallel by trypan blue exclusion. It is believed that ~70% viability was due to a period of approximately 2.5 hours that the cells were at room temperature after being trypsinized but before the loading experiment began. It is believed that by proceeding immediately from trypsinization to the next step (i.e., the loading step) in the protocol, the viability improves.

Figure 12I:
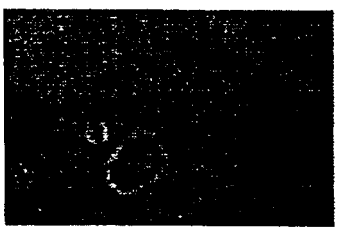
FIGS. 12I–12J are micrographs of a control sample (cells incubated in the absence of LYCH) of human mesenchymal stem cells taken at 630× on a Zeiss inverted microscope and having no LYCH-loading of the cells, with FIG. 12I showing phase contrast images and all cells intact and FIG. 12J showing no fluorescent images for the same cells of FIG. 12I because the fluorescence is specific to LYCH and does not correspond to auto-fluorescence from the human mesenchymal stem cells.
Figure 12J:
Figure 12G:
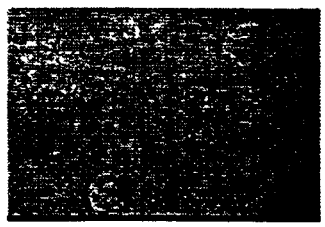
FIGS. 12G–12H are micrographs of human mesenchymal stem cells taken at 630× on a Zeiss inverted microscope 3.5 hours following LYCH-loading, with FIG. 12G showing phase contrast images and all cells intact and FIG. 12H showing fluorescent images for the same cells of FIG. 12G and the LYCH uptake after 3.5 hours.
Figure 12H:
Figure 12E:
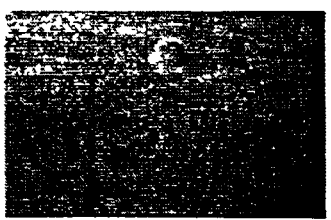
FIGS. 12E–12F are micrographs of human mesenchymal stem cells taken at 630× on a Zeiss inverted microscope 2 hours following LYCH-loading, with FIG. 12E showing phase contrast images and all cells intact and FIG. 12F showing fluorescent images for the same cells of FIG. 12E and the LYCH uptake after 2 hours.
Figure 12F:
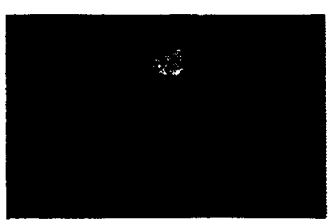
Figure 12C:
FIGS. 12C–12D are micrographs of human mesenchymal stem cells taken at 630× on a Zeiss inverted microscope 1 hour following LYCH-loading; with FIG. 12C showing phase contrast images and all cells intact and FIG. 12D showing fluorescent images for the same cells of FIG. 12C and the LYCH uptake after 1 hour.
Figure 12D:
Figure 12A:
FIGS. 12A–12B are micrographs of human mesenchymal stem cells taken at 630× on a Zeiss inverted microscope 30 minutes following LYCH-loading, with FIG. 12A showing phase contrast images and all cells intact and FIG. 12B showing fluorescent images for the same cells of FIG. 12A and the LYCH uptake after 30 minutes.
Figure 12B:

Micrographs taken in phase contrast and fluorescence modes of LYCH-loaded cells are shown in FIGS. 12A–12J. FIGS. 12A–12B are micrographs of the human mesenchymal stem cells taken at 630× on a Zeiss inverted microscope 30 minutes following LYCH-loading, with FIG. 12A showing phase contrast images and all cells intact and FIG. 12B showing fluorescent images for the same cells of FIG. 12A and the LYCH uptake after 30 minutes. FIGS. 12C–12D are micrographs of the human mesenchymal stem cells taken at 630× on a Zeiss inverted microscope 1 hour following LYCH-loading, with FIG. 12C showing phase contrast images and all cells intact and FIG. 12D showing fluorescent images for the same cells of FIG. 12C and the LYCH uptake after 1 hour. FIGS. 12E–12F are micrographs of the human mesenchymal stem cells taken at 630× on a Zeiss inverted microscope 2 hours following LYCH-loading, with FIG. 12E showing phase contrast images and all cells intact and FIG. 12F showing fluorescent images for the same cells of FIG. 12E and the LYCH uptake after 2 hours. FIGS. 12G–12H are micrographs of the human mesenchymal stem cells taken at 630× on a Zeiss inverted microscope 3.5 hours following LYCH-loading, with FIG. 12G showing phase contrast images and all cells intact and FIG. 12H showing fluorescent images for the same cells of FIG. 12G and the LYCH uptake after 3.5 hours. FIGS. 12I–12J are micrographs of a control sample (cells incubated in the absence of LYCH) of the human mesenchymal stem cells taken at 630× on a Zeiss inverted microscope and having no LYCH-loading of the cells, with FIG. 12I showing phase contrast images and all cells intact and FIG. 12J showing no fluorescent images for the same cells of FIG. 12I because the fluorescence is specific to LYCH and does not correspond to auto-fluorescence from the human mesenchymal stem cells.

Phase contrast images showed that all cells were intact. The fluorescence micrographs showed the progression of LYCH uptake over time. At earlier time points, the cytoplasm was only dimly stained, and bright punctate staining near the plasma membrane indicated dye uptake into vesicles. This suggests that the loading likely occurred via an endocytotic mechanism. At later time points, the cytoplasm was more brightly and uniformly stained, indicating that leakage from the vesicles raised the concentration of dye throughout the cells.

Figure 13:
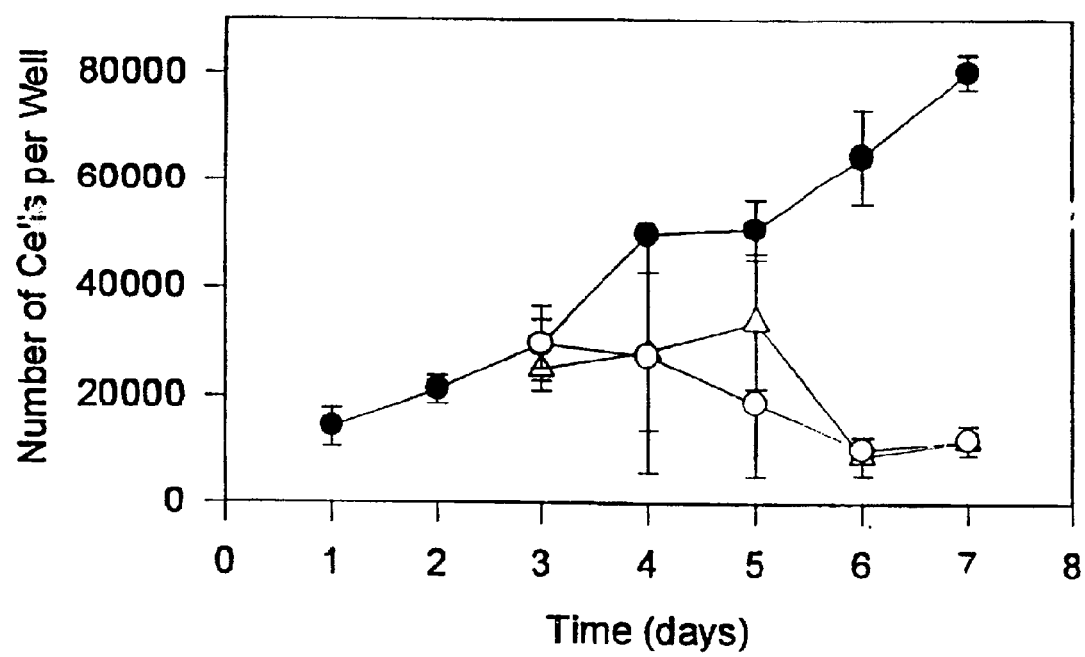
FIG. 13 is a graph illustrating growth curves for mesenchymal stem cells in the presence or absence of 90 mM trehalose with the open triangle data representing cells grown in standard medium for 24 hours, after which 90 mM trehalose was added.

Growth Curves. MSCs were plated into 12-welled plates at approximately the same seeding density used for T-185 flasks in standard Osiris protocols (5900 cells/cm$^2$ with fluid volume of 0.189 mL/cm$^2$). Three wells for each condition at each time point were trypsinized and counted. Data for cells grown in the presence of trehalose were lost for the first two time points. FIG. 13 is a graph illustrating growth curves for the mesenchymal stem cells in the presence or absence of 90 mM trehalose with the open triangle data representing cells grown in standard medium for 24 hours, after which 90 mM trehalose was added. It is clear from FIG. 13 that trehalose did not interfere with growth of the cells up to the third day. Subsequently, the cell count started to drop significantly in the presence of trehalose, and thus, incubation of MSCs for more than two days in trehalose should be avoided.

Freeze-Drying Mesenchymal Stem Cells. Human MSCs were prepared for freeze-drying by a 24-hour incubation at 37° C. in their standard growth medium plus 90 mM trehalose. The cells are likely to take up trehalose in a manner similar to that shown above for LYCH, as has been seen with platelets and epithelial 293H cells. Following the trehalose-incubation, MSCs were harvested, transferred to a freeze-drying buffer, and placed into two T-25 flasks modified for freeze-drying. The cell samples were freeze-dried on a Lyostar lyophilizer and rehydrated as detailed above. The freeze-dried cake was homogeneous and robust with no indications of collapse. The cells survived for several days following rehydration, as their plasma membranes were intact and their nuclei were clearly seen. In addition, some cells attached to the substrate and appeared to be initiating the stretched and spreading morphology. Overall health appeared better in the cell sample which had received the prehydration treatment prior to full rehydration.

Figure 16A:
FIG. 16A is a micrograph of mesenchymal stem cells magnified 100× following freeze-drying and rehydration.
Figure 16B:
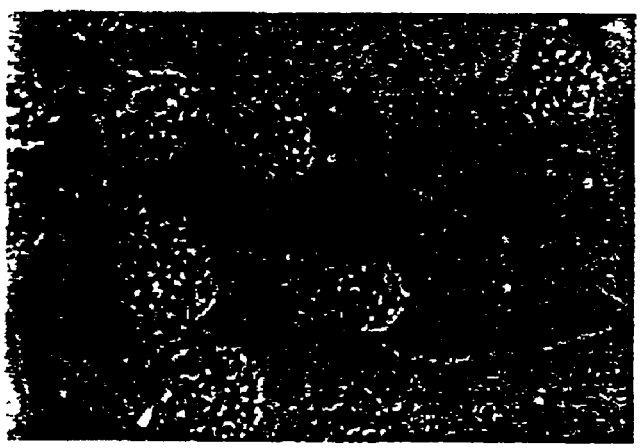
FIG. 16B is a micrograph of mesenchymal stem cells magnified 400× following freeze-drying and rehydration.
Figure 16C:
FIG. 16C is a micrograph of mesenchymal stem cells magnified 400× following freeze-drying, initial prehydration, and rehydration.

FIG. 14A is a micrograph at a 100× magnification of the healthy mesenchymal stem cell culture prior to harvest by trypsinization. FIG. 14B is a micrograph at a 320× magnification of the healthy mesenchymal stem cell culture of FIG. 14A prior to harvest by trypsinization. FIG. 15A is a 100× magnified image of the dry lyophilization "cake" of mesenchymal stem cells encased in strands of matrix containing trehalose and BSA. FIG. 15B is a 100× magnified image of the prehydrated lyophilization "cake" of mesenchymal stem cells encased in strands of matrix containing trehalose and BSA. FIG. 16A is a micrograph of the mesenchymal stem cells magnified 100× following freeze-drying and rehydration. FIG. 16B is a micrograph of the mesenchymal stem cells magnified 400× following freeze-drying and rehydration. FIG. 16C is a micrograph of the mesenchymal stem cells magnified 400×following freeze-drying, initial prehydration, and rehydration. FIG. 17A is a micrograph of the mesenchymal stem cells from the prehydrated sample at two days post rehydration, illustrating the attached cell and the beginning appearance of characteristic stretched morphology. FIG. 17B is a micrograph of the mesenchymal stem cells from the prehydrated sample at five days post rehydration, with nuclei clearly visible in several of the cells.

EXAMPLE 9

The procedures performed in this example were for epithelial 293H cells, and illustrate cell loading, freeze-drying, prehydration, FTIR analysis, and rehydration.

Trehalose Loading. Epithelial 293H cells chosen to be loaded with trehalose were taken from a stock culture, trypsinized, washed, and seeded into a new T-75 flask containing normal growth medium with the addition of 90 mM trehalose. The osmolarity of the medium was not adjusted, yielding a final culture medium osmolarity with trehalose of approximately 390 mOsm. Cells were allowed to grow in this state under normal incubation conditions for 72 hours. They were then harvested using standard protocols and resuspended in freeze-drying buffer immediately prior to the freeze-drying procedure. The freeze-drying buffer contained 130 mM NaCl, 10 mM HEPES (Na), 5 mM KCl, 150 mM trehalose, and 14.2 g BSA (5.7%) w/v. The buffer was at pH 7.2 and was maintained at 37° C.

Freeze-drying. Freeze-drying protocols were developed to optimize drying using the T-25 Lyoflasks. Cells were initially frozen at 5° C./min to 0° C. then at 2° C./min to −60° C. Once freeze-drying begins, cells were maintained under vacuum at −30° C. for 180 minutes, then at −25° C. for 180 minutes. Last, the cells are slowly ramped to room temperature over a 12 hour period under vacuum.

Figure 18B:
FIG. 18B is an enlarged view of the dashed square cell field in FIG. 18A with the arrows identifying exceptionally preserved cells.
Figure 18A:
FIG. 18A is a micrograph at 100× magnification of epithelial 293H cells freeze-dried in trehalose, with the cells remaining whole and round, closely resembling their native hydrated state.
Figure 19A:
FIG. 19A is a micrograph at 400× magnification of epithelial 293H cells freeze-dried in trehalose, and showing two 293H cells imbedded within a freeze-drying matrix composed of trehalose, albumin, and salts, with the cells appearing whole, round, and completely engulfed within the matrix.
Figure 19B:
FIG. 19B is an enlarged view of the dashed square cell field in FIG. 19A with two cells respectively identified by an arrow.

FIG. 18A is a micrograph at 100× magnification of the epithelial 293H cells freeze-dried in trehalose, with the cells remaining whole and round, closely resembling their native hydrated state. FIG. 18B is an enlarged view of the dashed square cell field in FIG. 18A with the arrows identifying exceptionally preserved cells. FIG. 19A is a micrograph at 400×magnification of the epithelial 293H cells freeze-dried in trehalose, and showing two epithelial 293H cells imbedded within a freeze-drying matrix composed of trehalose, albumin, and salts, with the cells appearing whole, round, and completely engulfed within the matrix. FIG. 19B is an enlarged view of the dashed square cell field in FIG. 19A with two epithelial cells respectively identified by an arrow.

Rehydration. Freeze-dried cells were either rehydrated directly with a rehydration buffer of 1:3 $H_2O$ to growth medium mixture, or were first prehydrated at 100% relative humidity for 45 min and then were fully rehydrated with the same rehydration buffer. Images were taken on a Zeiss inverted microscope using bright field or phase contrast at 100×, 320×, and 400× on Kodak Ektachrome ASA 400 film.

Figure 20A:
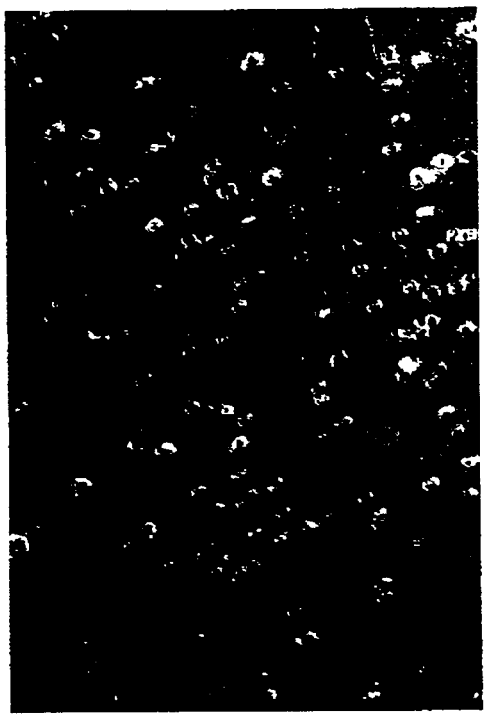
FIG. 20A is a micrograph at 100× magnification of epithelial 293H cells after prehydration (45 min @ 100% RH) and rehydration (1:3 ratio of $H_2O$:Growth Medium), and showing a high number of intact, refractile cells.
Figure 20B:
FIG. 20B is an enlarged view of the dashed square cell field in FIG. 20A.

FIG. 20A is a micrograph at 100× magnification of the epithelial 293H cells after prehydration (45 min @ 100% relative humidity) and rehydration (1:3 ratio of $H_2O$:growth medium), and showing a high number of intact, refractile cells. FIG. 20B is an enlarged view of the dashed square cell field in FIG. 20A. FIG. 21A is a micrograph at 320× magnification of the epithelial 293H cells 24 hours following rehydration, with refractile whole cells still visible. FIG. 21B is an enlarged view of the dashed square cell field in FIG. 21A with a refractile cell marked by an arrow.

FTIR Analysis. The protocol used for analysis of membrane phase transitions by Fourier transform infrared spectroscopy (Perkin-Elmer Spectrum 2000) was as follows: Cells, either hydrated or dry, with or without trehalose, were placed between $CaF_2$ windows. These samples were scanned between 3600 and 900 $cm^{-1}$ over a range of temperatures with a ramping rate of 2° C./min. Raw spectra were then analyzed for changes in wavenumber of the symmetric $CH_2$ stretching vibration of membrane lipids (around 2850). Band position was graphed as a function of temperature, and first derivative analysis indicates the membrane phase transition temperatures. Dried samples were prepared by freeze-drying and were loaded onto the windows in a dry box.

Use of the Lyoflasks for Freeze-Drying Epithelial 293H Cells. Following the freeze-drying procedure, the lyophilized epithelial 293H cells appeared to be optimally freeze-dried. The lyophilizate formed a dry cake that is indicative of proper drying, without having melted or collapsed. In the dry state, the cells appeared to be highly well-preserved in the trehalose/buffer matrix. Cells remained intact and round, similar to the shape and size seen in trypsinized epithelial 293H cells (see FIGS. 18A, 18B, 19A and 19B). By maintaining the cells' native structure, it appeared that the dried state encased within trehalose was sufficient.

Following rehydration, under both direct and prehydrated conditions, cells were mostly whole and intact following the addition of the rehydration buffer. Cells that were first prehydrated appeared more refractile than in the directly hydrated samples (see FIG. 20A and 20B). In both cases very few cells appeared lysed due to the reintroduction of water. Furthermore, cellular debris was almost completely absent from either condition. Overall, in the prehydrated sample, approximately 10% of the cells imaged appeared highly refractile initially (see FIGS. 20A and 20B).

Twenty-four (24) hours following rehydration, the rehydrated epithelial 293H cells in culture were again observed. Those cells in the prehydrated condition appeared to be more refractile and attached more strongly to the growth surface than those in the non-prehydrated sample (see FIGS. 21A and 21B). In the prehydrated condition, approximately 6 to 7% of the cells remained phase bright. It was apparent, however, that cellular debris became abundant and that many cells had lysed.

EXAMPLE 10

The physical membrane properties of human erythrocytes were studies in situ using Fourier transform infrared spectroscopy (FTIR). Erythrocyte membranes were found to have weakly cooperative phase transitions at 14° C. and at 34° C. Cholesterol depletion by methyl-β-cyclodextrin (MβCD) resulted in a large increase in the cooperativity of these transitions, and led to the appearance of another phospholipid transition at 25° C. Multiple, sharp membrane phase transitions were observed after five days cold storage (4° C.), which indicated phase separation of the membrane lipids. Using fluorescence microscopy, it was determined that the lipid probe 1,1'-dioctadecyl-3,3,3',3'-tetramethyl-indocarbocyanine perchlorate (dil-$C_{18}$) remained homogeneously distributed in the erythrocyte membrane during cold storage, suggesting that lipid domains were below the resolution limit of the microscope. Using thin layer chromatography, changes in the membrane lipid composition were detected during cold storage. By contrast, assessment of the amide-II band with FTIR showed that the overall protein secondary structure of hemoglobin was stable during cold stage.

Fundamental knowledge about membrane phase transition temperatures is of practical importance for determining the in vitro storage conditions of erythrocytes in blood banks. We anticipate that especially the phase transition temperature at around 34° C. may be used to load erythrocytes with trehalose, or any other lyoprotectant and that intracellular trehalose allows the erythrocytes to survive freeze-drying. Freeze-dried erythrocytic cells will find broad applications in the field of medicine, pharmaceuticals and biotechnology.

Experimental Procedures

Isolation of Erythrocytes, Cholesterol Depletion, Preparation of Ghosts, and Storage Conditions. Venous blood was collected from healthy adults, with informed consent, according to institutional protocols. Blood was anticoagulated with ACD (citric acid, citrate, dextrose). Whole blood was centrifuged at 320 x g for 8 minutes. The cellular pellet (red blood cells) was washed three times in PBS buffer (100 mM NaCl, 9.4 mM $Na_2HPO_4$, 0.6 mM $KH_2PO_4$, pH 7.4) prior to further analysis. Cells were incubated at 37° C. for one hour in the presence of 1 mM methyl-β-cyclodextrin (MβCD) in order to remove cholesterol from the plasma membranes.

FTIR Spectroscopy and Sample Preparation. Infrared spectra were recorded on a Perkin-Elmer 2000 Fourier transform IR-spectrometer. Red cell pellets were spread between two $CaF_2$ infrared windows in a temperature-controlled cell. Intact cells were cooled to –5° C., kept at this temperature for 15 minutes, and then rewarmed to determine the phase transitions. Forty to 50 spectra were recorded over a temperature range from –5° C. to +45° C., at a heating rate of 5° C./min. Data processing consisted of taking the second derivative of the IR-absorfance spectra using a 9 point smoothing factor. Inverted second derivative spectra were normalized on the lipid band around 2850 $cm^{-1}$. Band positions were determined by averaging the intercepts at 80% of the absorbance maximum. The wavenumber ($cm^{-1}$) of the $CH_2$ symmetric stretching vibration was plotted as a function of temperature. The first derivative of the wavenumber versus temperature plots was calculated to show inflections more clearly and are a measure of the cooperativity of the transitions. Phase transition temperatures and cooperativity values were determined from the maxima in the first derivative plots.

Figure 24:
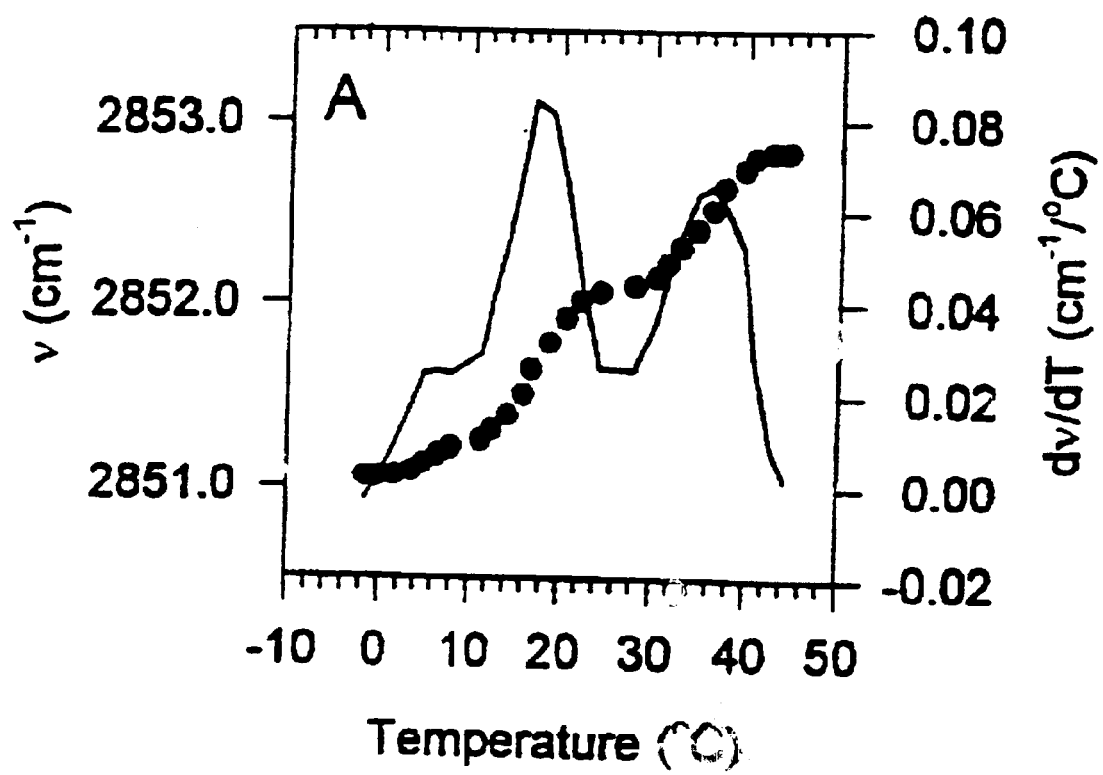
FIG. 24 is a graph of wavenumber versus temperature plot of the $CH_2$ symmetric stretching mode of erythrocytes from a first blood donor, along with first derivatives of the wavenumber versus temperature plots.
Figure 25:
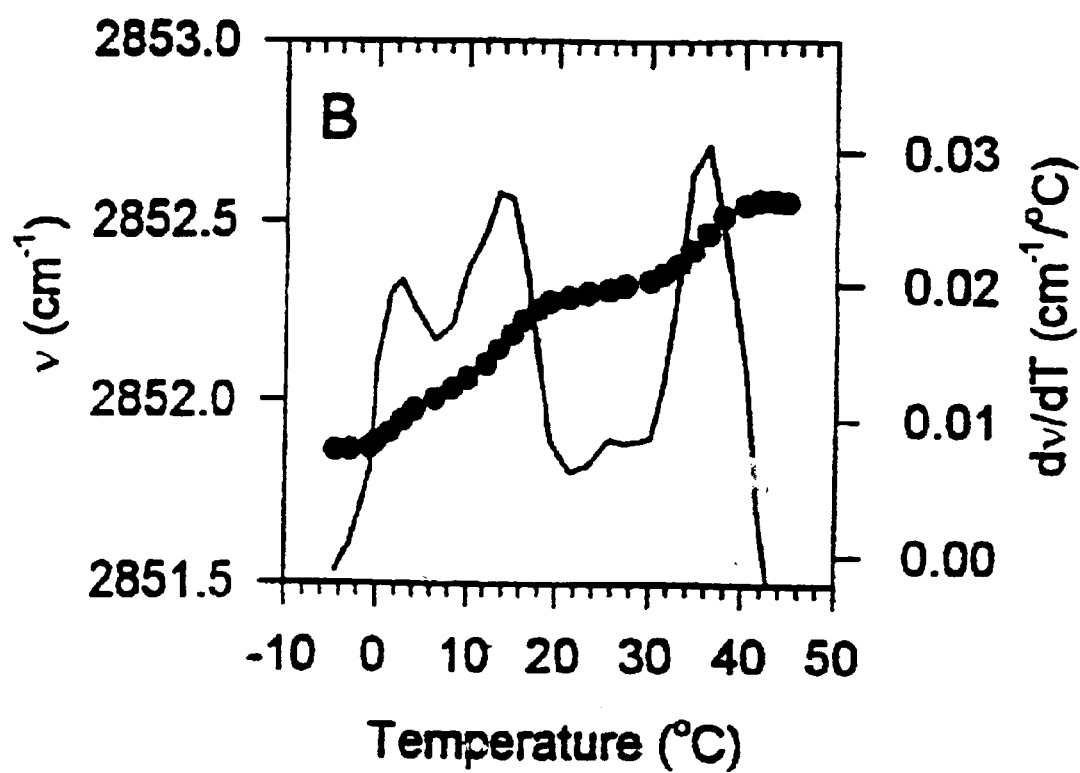
FIG. 25 is a graph of wavenumber versus temperature plot of the $CH_2$ symmetric stretching mode of erythrocytes from a second blood donor, along with first derivatives of the wavenumber versus temperature plots.
Figure 26:
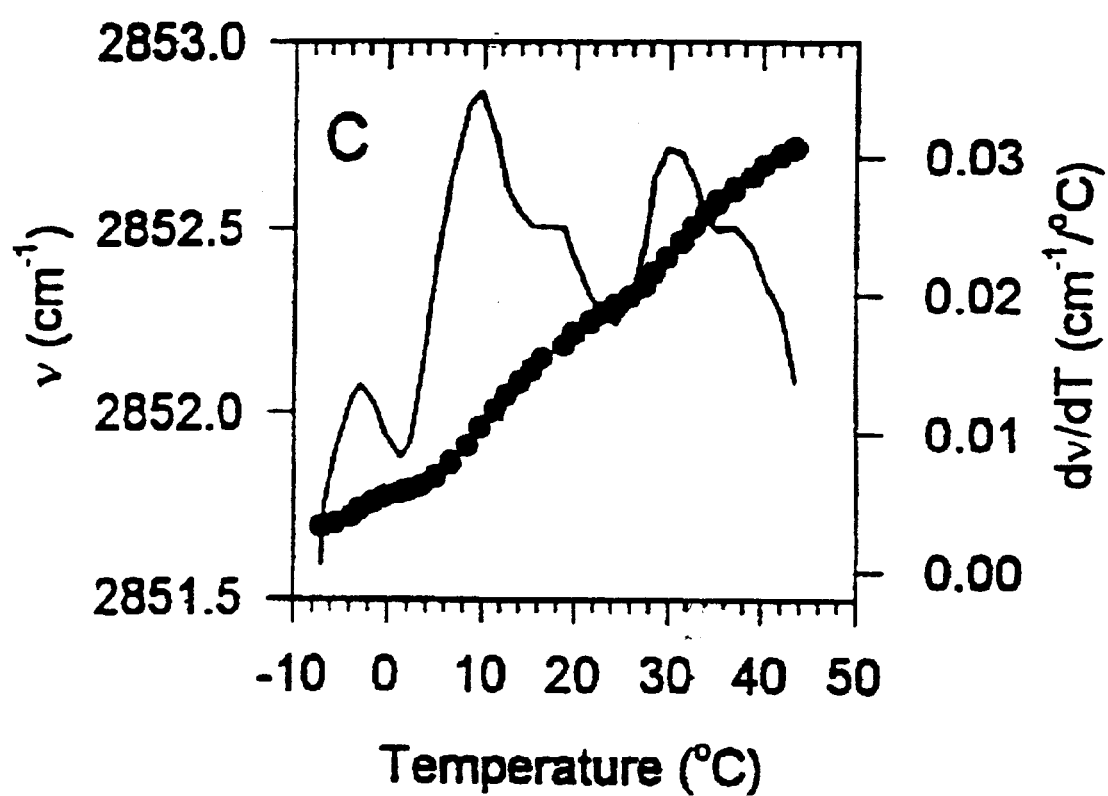
FIG. 26 is a graph of wavenumber versus temperature plot of the $CH_2$ symmetric stretching mode of erythrocytes from a third blood donor, along with first derivatives of the wavenumber versus temperature plots.

FTIR Analysis of Intact Erythrocytes. In situ FTIR analysis of erythrocytes revealed the presence of two clear inflection points in the wavenumber versus temperature plot of the lipid methylene stretching mode at around 2850 $cm^{-1}$ (see FIGS. 24–26). The first derivative of the wavenumber versus temperature plot was calculated to determine the phase transition temperatures. Two transition temperatures were detected in all cases, centered on approximately 14 and 34° C. The thermotropic response depicted in FIG. 24 was strikingly different from that shown in FIGS. 25 and 26. The total wavenumber excursion in FIG. 24 was almost 1.5 $cm^{-1}$ (from –5 to 45° C.) as compared to 0.8 $cm^{-1}$ in FIGS. 25 and 26. The cooperativity of the transitions (maxima in the first derivative plot) in FIG. 24 were also strikingly higher compared with the other donors. We discovered that the donor for this experiment used LIPITOR (Pfizer Pharmaceuticals, Ct), and we speculate that this blood cholesterol lowering compound may have affected the erythrocyte membrane properties. Table 1 below presents the average transition temperatures and concomitant cooperativity values. The two transitions in the intact cells at 14 and 34° C. had cooperativity values of 0.036 and 0.031 $cm^{-1}/°$ C., respectively, suggesting that the two transitions are equally cooperative.

Figure 27:
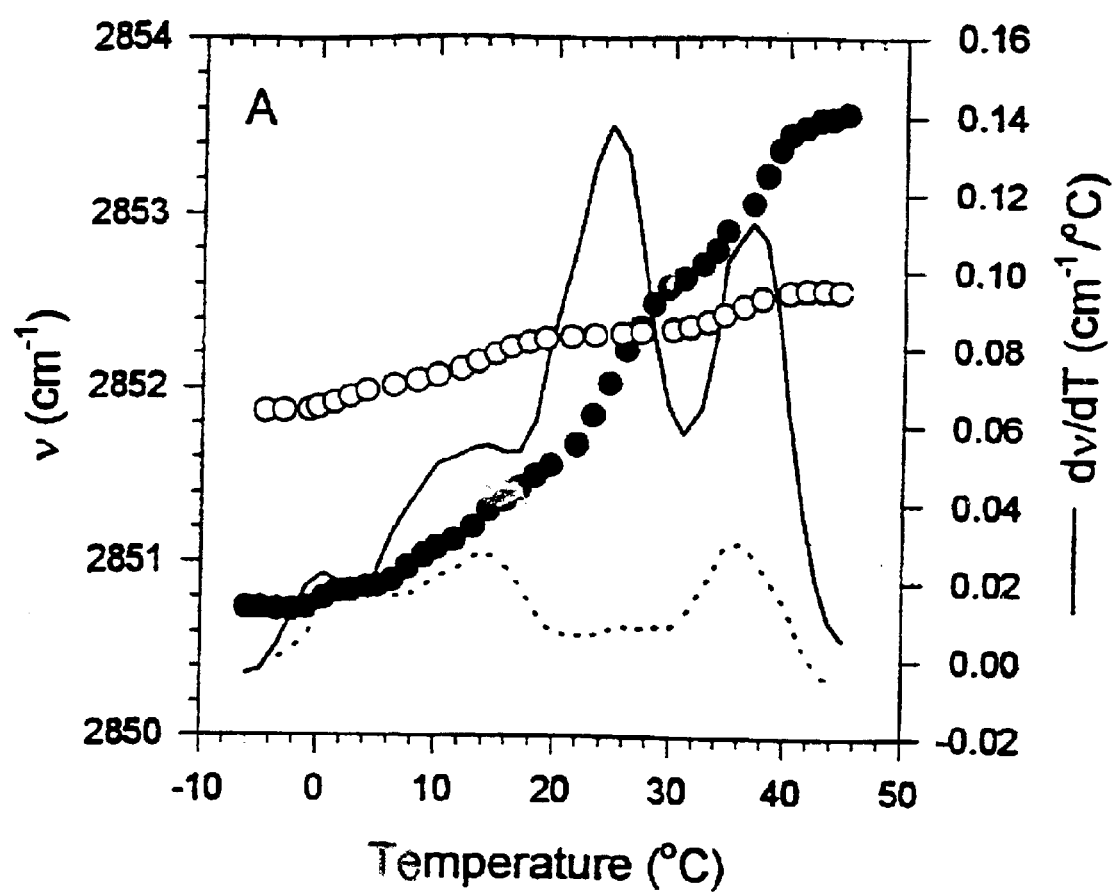
FIG. 27 is a graph of wavenumber versus temperature plots of control (open circles) and MβCD treated erythrocytes (filled circles), along with first derivatives of the wavenumber versus temperature plots (solid lines correspond to MβCD treated cells, and dotted lines correspond to control cells)

Cholesterol Depletion. MβCD was used to remove cholesterol selectively from the erythrocyte membranes. Cholesterol removal had a drastic effect on the thermotropic response of the membrane as is shown in FIG. 27. The wavenumber excursion from –5 to 45° C. increased from 0.7 to 2.9 $cm^{-1}$ upon cholesterol removal. At high temperatures, when the membranes are in a disordered phase, the wavenumber of the lipid band increased after cholesterol depletion of the cells and at lower temperatures, when the membranes are in a more ordered phase, cholesterol depletion resulted in a lower wavenumber compared to control cells. This indicates that cholesterol fluidizes the membrane at low temperatures and rigidities the membrane at high (physiological) temperatures.

The following Table I illustrates the midpoint of phase transitions of MβCD-treated and control erythrocytes as derived from FTIR wavenumber (band around 2850 $cm^{-1}$) versus temperature plots:

TABLE I

| Lipids | Low Transition | Middle Transition | High Transition |
|---|---|---|---|
| | Transition Temperature (° C.) | | |
| Control Erythrocytes | 14.4 ± 1.3 | | 34.2 ± 1.4 |
| MβCD Treated Erythrocytes | 15.3 ± 0.8 | 26.0 ± 0.8 | 35.4 ± 1.5 |

The following Table II illustrates the cooperativity of phase transitions of MβCD-treated and control erythrocytes as derived from FTIR wavenumber (band around 2850 cm$^{-1}$) versus temperature plots:

TABLE II

| Lipids | Low Transition | Middle Transition | High Transition |
|---|---|---|---|
| | Cooperativity (cm$^{-1}$/° C.) | | |
| Control Erythrocytes | 0.036 ± 0.013 | | 0.031 ± 0.010 |
| MβCD Treated Erythrocytes | 0.051 ± 0.004 | 0.095 ± 0.015 | 0.091 ± 0.020 |

Three phase transitions at about 15° C., 26° C. and 35° C. were visible after cholesterol removal from the plasma membranes, and, as expected, the cooperativity of the transitions was greater compared to the control erythrocytic cells. The cooperativity of the transition at about 15° C. was found to be only slightly higher than the corresponding transition in the intact erythrocytes. The cooperativity of the transition at about 35° C., which was also observed in the non-treated control erythrocytic cells, showed a large increase from about 0.031 to about 0.091 cm$^{-1}$/° C. after cholesterol removal. The transition at about 26° C. was not visible in intact erythrocytes, possibly due to broadening by the abundant cholesterol in the membrane. The cooperativity of this transition was about 0.095 cm$^{-1}$/° C.

EXAMPLE 11

Biological membranes may be thought to be in the lamellar liquid-crystalline phase at physiological temperatures. The lipids may be organized in a two dimensional array with acyl chains relatively disordered. At low temperatures, a lamellar gel phase may be formed, in which case lipid acyl chains would be highly ordered and more tightly packed together. A lipid bilayer consisting of one phospholipid species may be characterized by its gel to liquid-crystalline phase transition temperature, $T_m$. In a cell membrane, the situation is more complex, because the mixture of lipids, sterols and proteins and the preferential interactions between these components causes a complex thermal phase behavior.

In human erythrocytes there is an asymmetric distribution of phospholipids between both sides of the bilayer membrane. The outer layer contains predominantly phosphatidyl choline and sphingomyelin, whereas the inner layer consists mainly of phosphatidyl ethanolamine and phosphatidyl serine. The lipid composition directly affects membrane fluidity. Other membrane components, such as cholesterol and proteins, also have affects on the membrane. Cholesterol fluidizes the lipid bilayer in the gel state and reduces the motional order in the fluid state. Moreover, cholesterol preferentially interacts with specific lipids in the membrane, particularly with sphingolipids.

FTIR has been proven to be a very useful method for studying physical properties of membranes both in model systems from isolated lipids as well as in situ in whole cells. The wavenumber of the CH$_2$ stretching mode around 2850 cm$^{-1}$ is an indicator of the acyl chain conformational order and may be used to determine phase transitions in cells and tissues. This band mainly arises from endogenous lipids. It has been discovered from FTIR studies on human platelets that these cell fragments have a major phase transition around 15° C. and a second transition at around 30° C. Platelets should be stored at 22° C. or warmer, well above their main membrane phase transition temperature. In contrast, human erythrocytes may be stored for up to 20 days at 5° C. in anticoagulant-preservative solutions.

FTIR may also be used to assess the overall protein secondary structure of intact cells or organisms in situ. The application of FTIR to proteins may be based on the assessment of the amide-I band, located between 1600–1700 cm$^{-1}$, and the amide-II band, located between 1600–1500 cm$^{-1}$.

FTIR may further also be used to assess the membrane fluidity and the overall protein secondary structure of erythrocytes in situ, thereby omitting the use of interfering probe molecules. As previously indicated methyl-β-cyclodextrin may be used to remove cholesterol selectively from cells and examine the concomitant effect on membrane fluidity. Changes in membrane fluidity and overall protein secondary structure were studied during storage at 4° C. In addition, changes in the membrane lipid composition of the cells were measured using thin layer chromatography, and the formation lipid macro-domains was investigated using fluorescent dye diI-C$_{18}$.

Figure 28:
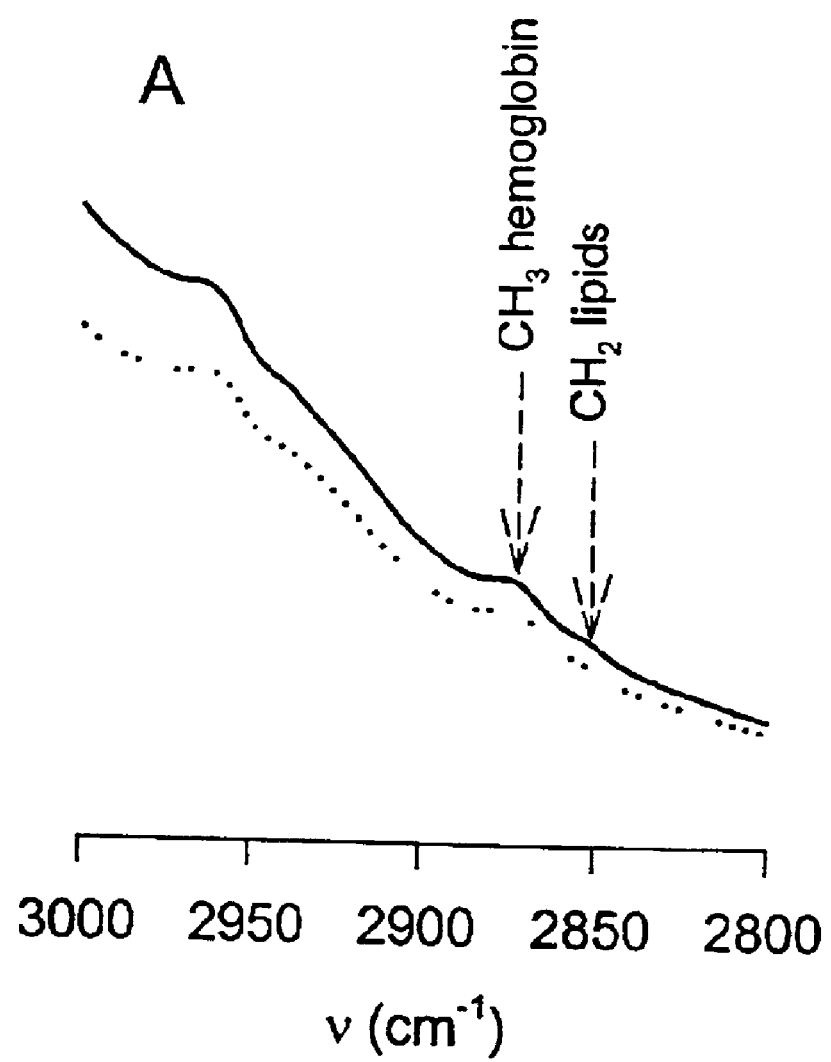
FIG. 28 is a graph of FTIR analysis of the $CH_2$ stretching region of erythrocytes at 4° C. (solid lines) and 37° C. (dotted lines), and an absorbance spectra in the 3000–2800 $cm^{-1}$ spectral region.
Figure 29:
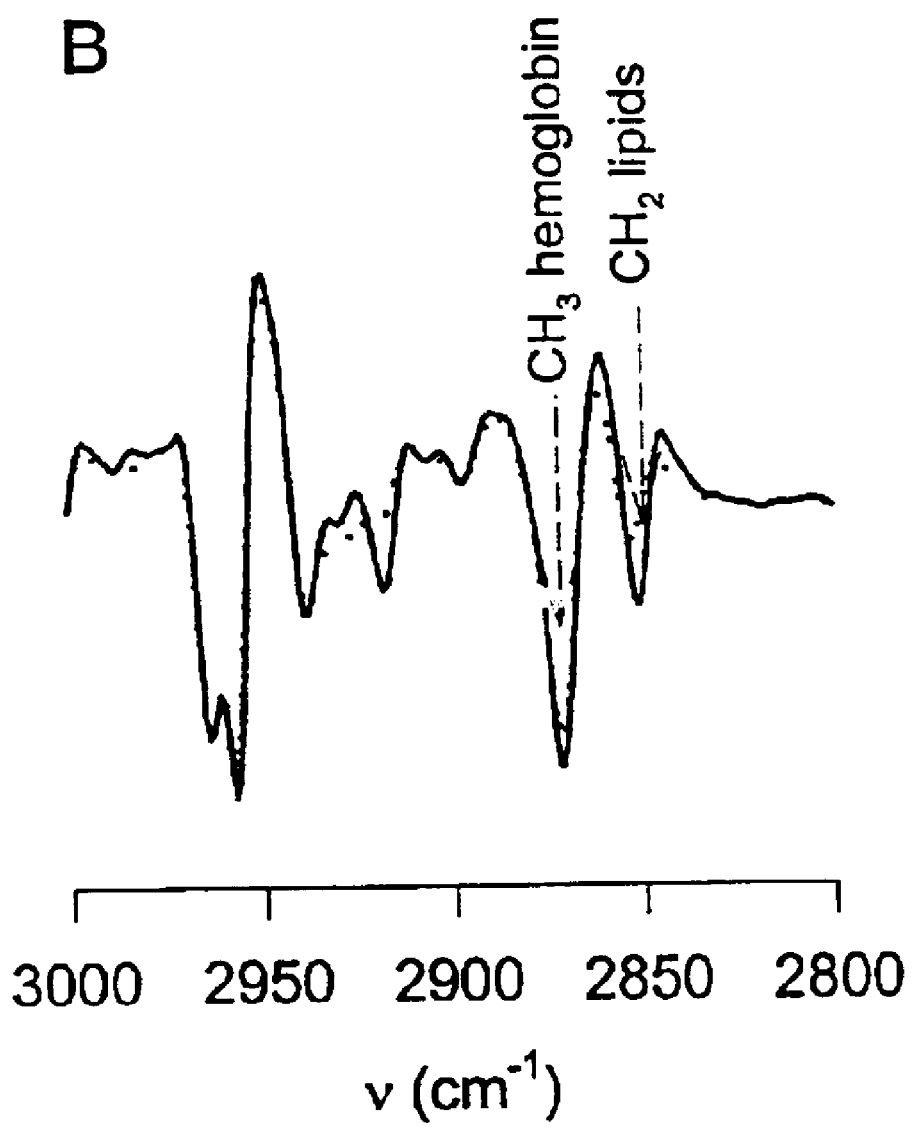
FIG. 29 is a graph of FTIR analysis of the $CH_2$ stretching region of erythrocytes at 4° C. (solid lines) and 37° C. (dotted lines), with the protein band at 2880 $cm^{-1}$ and the lipid band at 2855 $cm^{-1}$ being resolved after taking the second derivative of the absorbance spectra.
Figure 30:
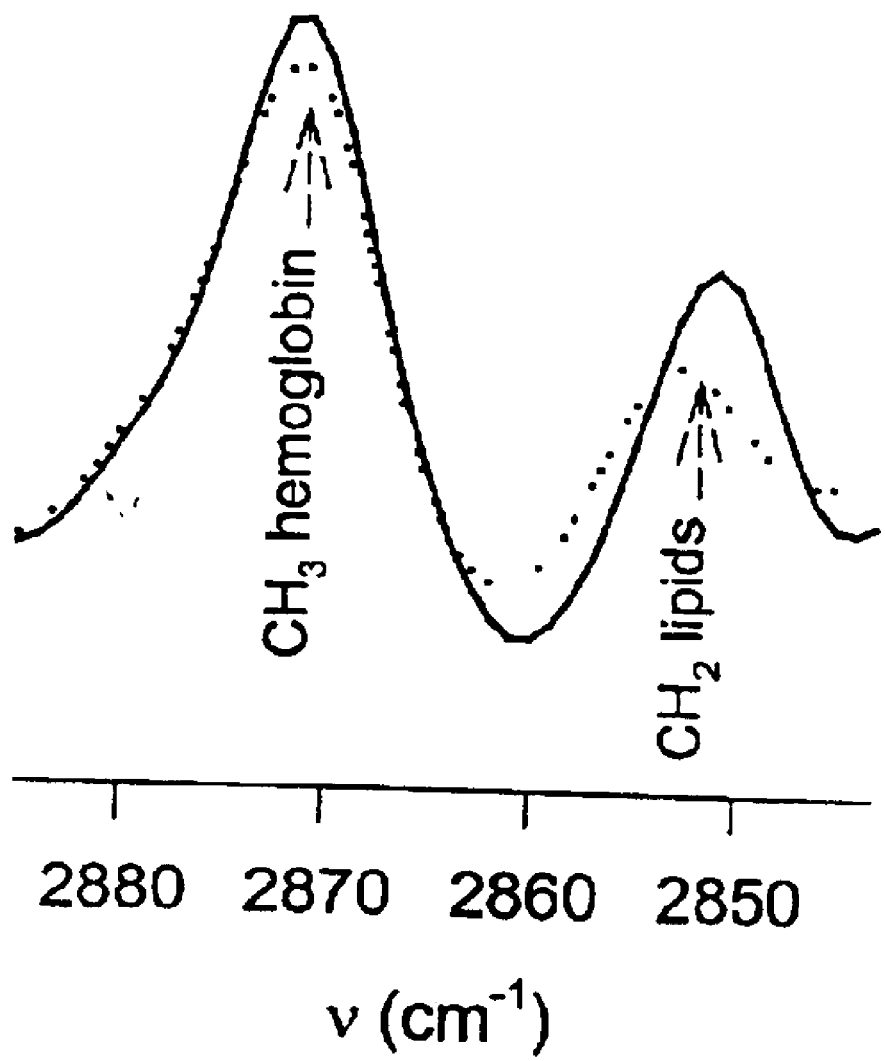
FIG. 30 is a graph of FTIR analysis of the $CH_2$ stretching region of erythrocytes at 4° C. (solid lines) and 37° C. (dotted lines), with an inverted second derivative spectra in the 2890–2835 $cm^{-1}$ region showing that only the lipid band shifts with temperature.

FTIR Analysis of Intact Erythrocytes. Red cells were washed three times in PBS buffer prior to in situ IR analyses to reduce interference of plasma components. FIG. 28 depicts an enlargement of the IR 3000–2800 cm$^{-1}$ region of erythrocytes at two different temperatures. The different bands in this region are more clearly visible after taking the second derivative of the absorbance spectra, as best shown in FIG. 29. The pronounced bands at 2870 and 2950 cm$^{-1}$ can be assigned to CH$_3$ stretching vibrations of endogenous erythrocyte proteins, substantially hemoglobin. The band at around 2850 cm$^{-1}$, which is visible only as a small shoulder next to the protein band (see FIG. 28) in the absorbance spectra, is clearly resolved from the protein CH$_3$ band in the second derivative spectra, as shown in FIG. 29. This band has been assigned to the symmetric methylene stretching vibration of the membrane lipids. The wavenumber of the CH$_3$ band did not shift significantly with increasing temperature, whereas the lipid band clearly shifted to a higher wavenumber with increasing temperature, indicating an increase in membrane fluidity (see FIG. 30).

Figure 31:
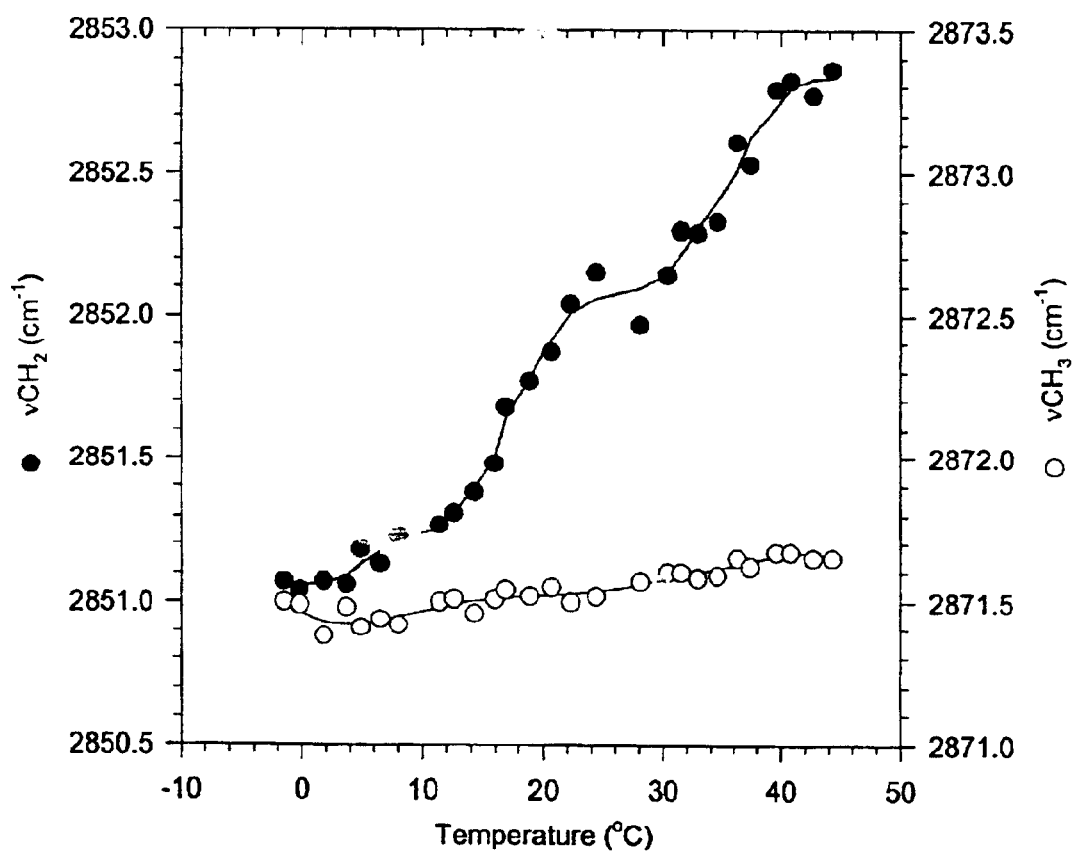
FIG. 31 is a graph illustrating the thermotropic response of the symmetric $CH_2$ vibration (filled circles) arising from endogenous lipids, and the symmetric $CH_3$ stretch vibration (open circles) arising from endogenous proteins in intact erythrocytes.
Figure 32:
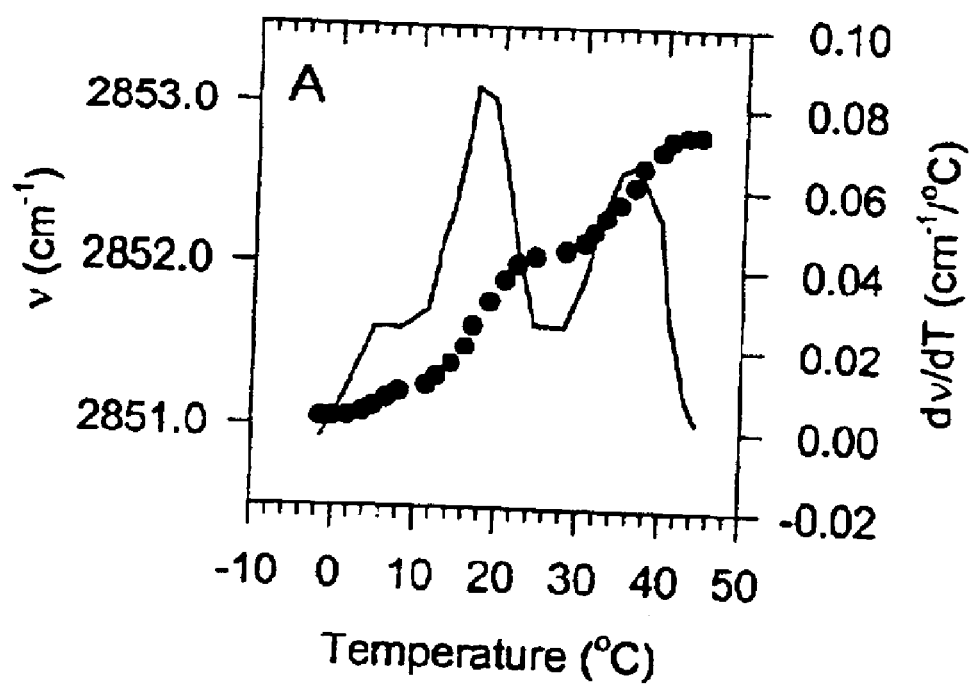
FIG. 32 is a graph of wavenumber versus temperature plot of the $CH_2$ symmetric stretching mode of erythrocytes from a first blood donor, along with first derivatives of the wavenumber versus temperature plots.
Figure 33:
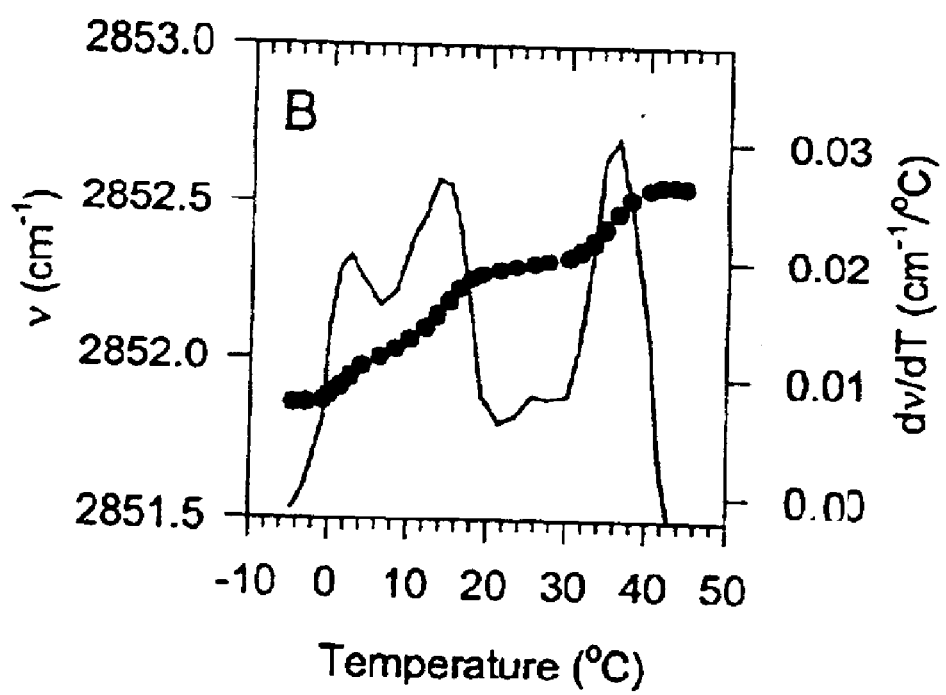
FIG. 33 is a graph of wavenumber versus temperature plot of the $CH_2$ symmetric stretching mode of erythrocytes from a second blood donor, along with first derivatives of the wavenumber versus temperature plots.
Figure 34:
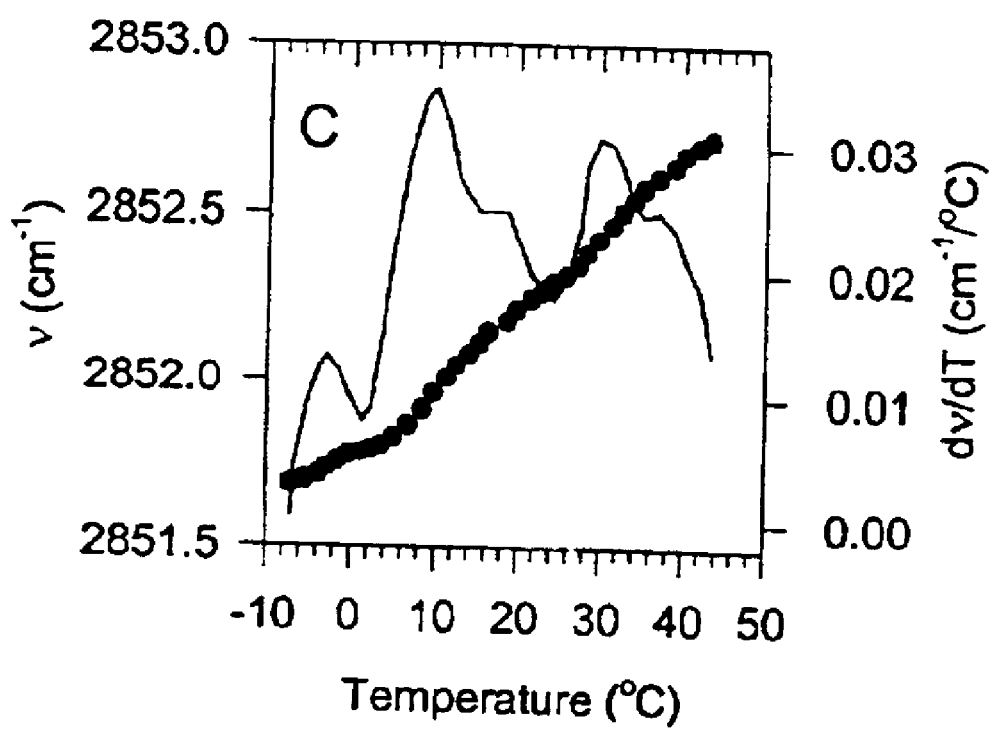
FIG. 34 is a graph of wavenumber versus temperature plot of the $CH_2$ symmetric stretching mode of erythrocytes from a third blood donor, along with first derivatives of the wavenumber versus temperature plots.

Membrane Phase Transitions in Erythrocytes. Two clear inflection points were observed in the wavenumber versus temperature plot of the lipid methylene stretching mode, as best shown in FIG. 31 which illustrates the thermotropic response of the symmetric CH$_2$ stretch vibration (filled circles) arising from endogenous lipids, and the symmetric CH$_3$ stretch vibration (open circles) arising from endogenous proteins in intact erythrocytes. The data were smoothed using a Savitzky-Golay routine, and the first derivative of the wavenumber versus temperature plot was calculated to determine the phase transition temperatures, as best shown in FIG. 32 which is a graph of wavenumber versus temperature plots of the CH$_2$ symmetric stretching mode of erythrocytes from one blood donor, along with the first derivatives of the wavenumber versus temperature plots which were employed to determine the phase transition temperatures and concomitant co-operativity values. The thermotropic responses of erythrocytes from two other donors are shown in FIGS. 33 and 34, to illustrate the variation between three different donors. FIGS. 33 and 34 illustrate respectively wavenumber versus temperature plots of the $CH_2$ symmetric stretching mode of erythrocytes from two additional blood donors, along with first derivatives of the wavenumber versus temperature plots which were used to determine the phase transition temperatures and concomitant co-operativity values. Two transition temperatures were detected in erythrocytes from these three blood donors, centered on approximately 14 and 34° C. The thermotropic response depicted in FIG. 32 was different from those shown in FIGS. 33 and 34. The total wavenumber excursion in FIG. 32 was almost 1.5 $cm^{-1}$ (from −5 to 45° C.) as compared to 0.8 $cm^{-1}$ in FIGS. 33 and 34. The cooperativity of the transitions (maxima in the first derivative plot) in FIG. 32 were also higher compared with the two donors shown in FIGS. 33 and 34. It was discovered that the donor for the experiment in FIG. 32 used LIPITOR (Pfizer Pharmaceuticals, CT), and it is believed that this blood cholesterol lowering compound may have affected the erythrocyte membrane properties. The thermotropic responses depicted in FIGS. 33 and 34 are more typical for erythrocytes.

The following Table III broadly presents the average transition temperatures and concomitant cooperativity values of five different donors.

TABLE III

| Lipids | Low Transition | Middle Transition | High Transition |
|---|---|---|---|
| Transition Temperature (° C.) | | | |
| Control Erythrocytes | 14.4 ± 1.3 | | 34.2 ± 1.4 |
| MβCD Treated Erythrocytes | 15.3 ± 0.8 | 26.0 ± 0.8 | 35.4 ± 1.5 |
| Cooperativity ($cm^{-1}$/° C.) | | | |
| Control Erythrocytes | 0.036 ± 0.013 | | 0.031 ± 0.010 |
| MβCD Treated Erythrocytes | 0.051 ± 0.004 | 0.095 ± 0.015 | 0.091 ± 0.020 |

The foregoing Table III more specifically illustrates cooperativity and midpoint of phase transitions of MβCD-treated and control erythrocytes as derived from FTIR wavenumber (band around 2850 $cm^{-1}$) versus temperature plots, with their associated standard error, for five blood donors. The two transitions (i.e., the low and high transitions) in the intact cells at 14 and 34° C., had cooperativity values of 0.036 and 0.031 $cm^{-1}$/° C., respectively, suggesting that the two transitions are equally cooperative.

Figure 35:
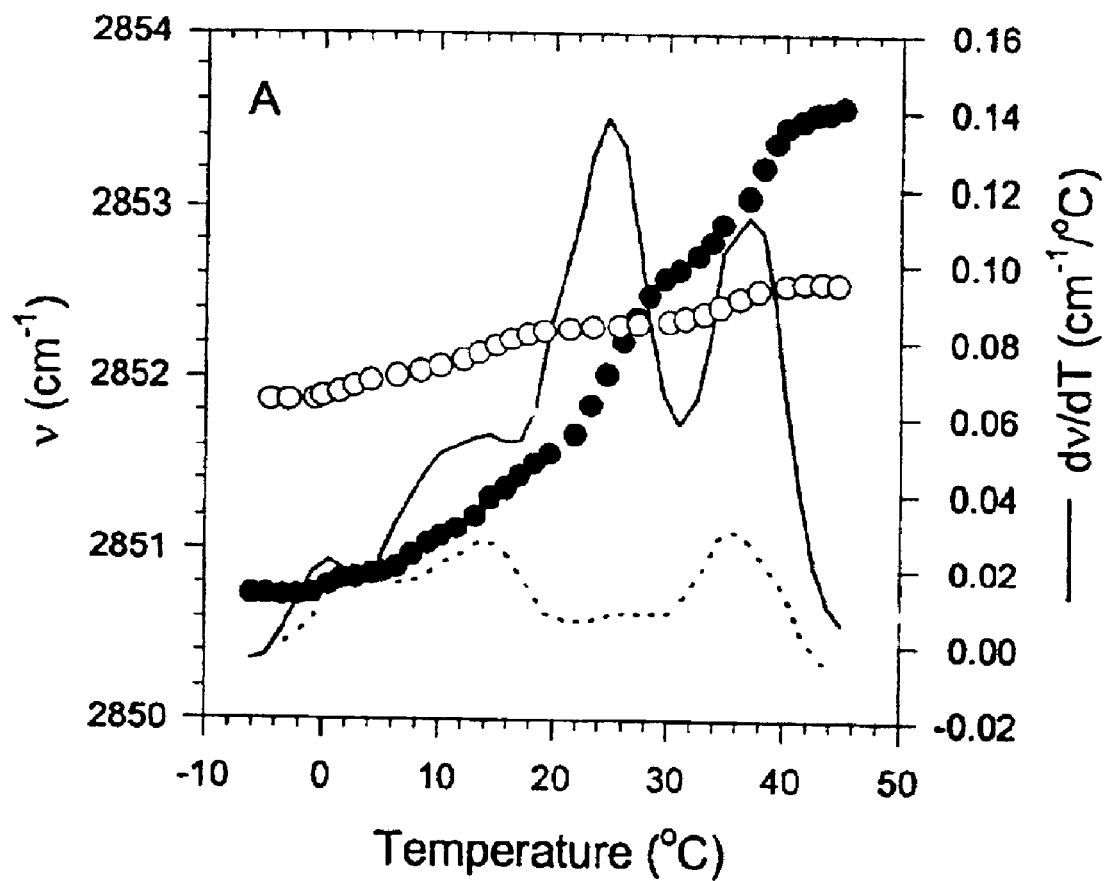
FIG. 35 is a graph of wavenumber versus temperature plots of control (open circles) and MβCD treated erythrocytes (filled circles), along with first derivatives of the wavenumber versus temperature plots (solid lines correspond to MβCD treated cells, and dotted lines correspond to control cells)

Cholesterol Depletion. MβCD was used to remove cholesterol from the erythocyte membranes. Cholesterol removal had a drastic effect on the thermotropic response of the membrane, as best shown in FIG. 35. The wavenumber excursion from −5 to 45° C. increased from 0.7 to 2.9 $cm^{-1}$ upon cholesterol removal. At high temperatures, when the membranes are in a disordered state, the wavenumber of the lipid band increased after cholesterol depletion of the cells and at lower temperatures, when the membranes are in a more ordered state, cholesterol depletion resulted in a lower wavenumber compared to control cells. This indicates that cholesterol fluidizes the membrane at low temperatures and rigidities the membrane at high (physiological) temperatures.

The three transitions at 15, 26, and 35° C. were visible after cholesterol removal from the plasma membranes, and, as expected, the cooperativity of the transitions was greater compared to the control cells. The cooperativity of the transitions was greater compared to the control cells. The cooperativity of the transition at 15° C. was found to be slightly higher than the corresponding transition in the intact erythrocytes. The cooperativity of the transition at 35° C., which was also observed in the non-treated control cells, showed a large increase from 0.031 to 0.091 $cm^{-1}$/° C. after cholesterol removal. The transition at 26° C. was not visible in intact erythrocytes, possibly due to broadening by the abundant cholesterol in the membrane. The cooperativity of this transition was 0.095 $cm^{-1}$/° C.

Figure 36:
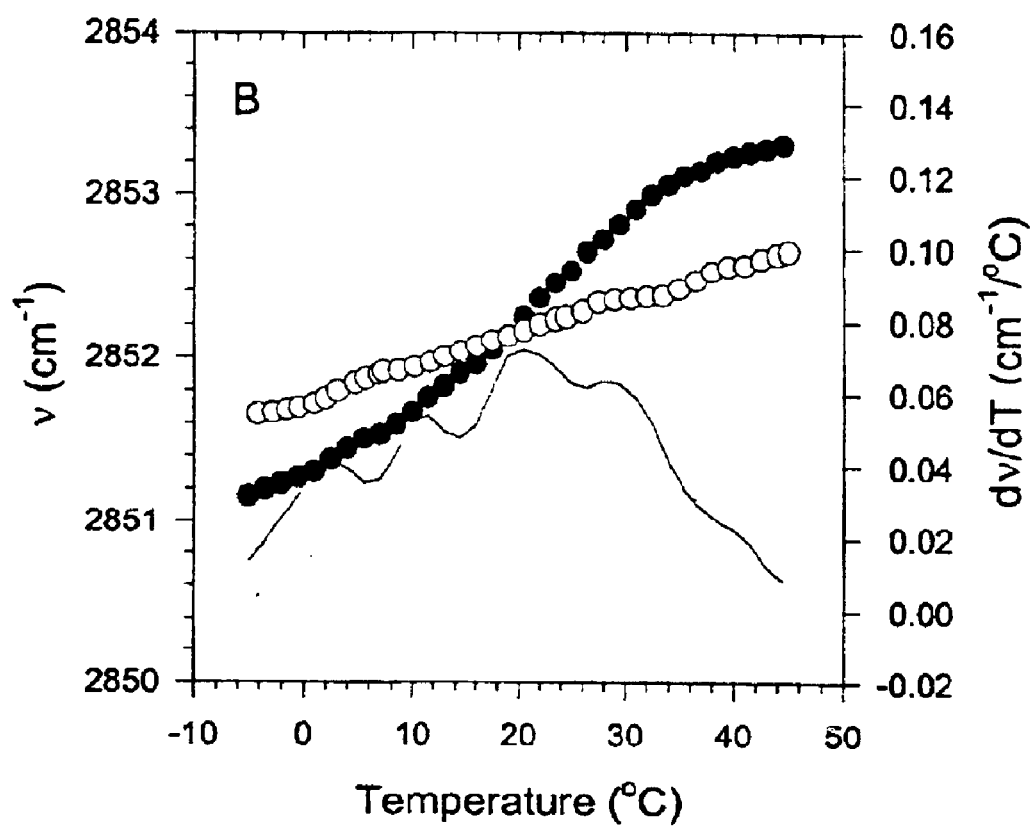
FIG. 36 is a graph of wavenumber versus temperature plots of control ghosts (open circles) and MβCD treated ghosts (filled circles), along with first derivatives of the wavenumber versus temperature plots (solid lines correspond to MβCD treated cells, and dotted lines correspond to control cells)

Ghosts. The thermotropic response of erythrocyte ghosts were studied to corroborate the results with the intact erythrocytes. As best shown in FIG. 36, the wavenumber of the $CH_2$ stretching band in ghosts gradually increased from 2851.7 to 2852.6 $cm^{-1}$ when the temperature was increased from −5 to 45° C. Four minor transitions at approximately 3, 15, 24 and 36° C. were visible after first derivative analysis. The cooperativity of these transitions was lower compared with those in the intact erythrocytes. Again, cholesterol removal enhanced the cooperativity of the transitions, which were observed at slightly different temperatures, at 4, 12, 20 and 30° C., compared with the non-MβCD treated ghosts. The differences in thermotropic response of ghosts compared with the intact erythrocytes suggest a rearrangement of the membrane lipids (and proteins) upon hemolysis.

Figure 37:
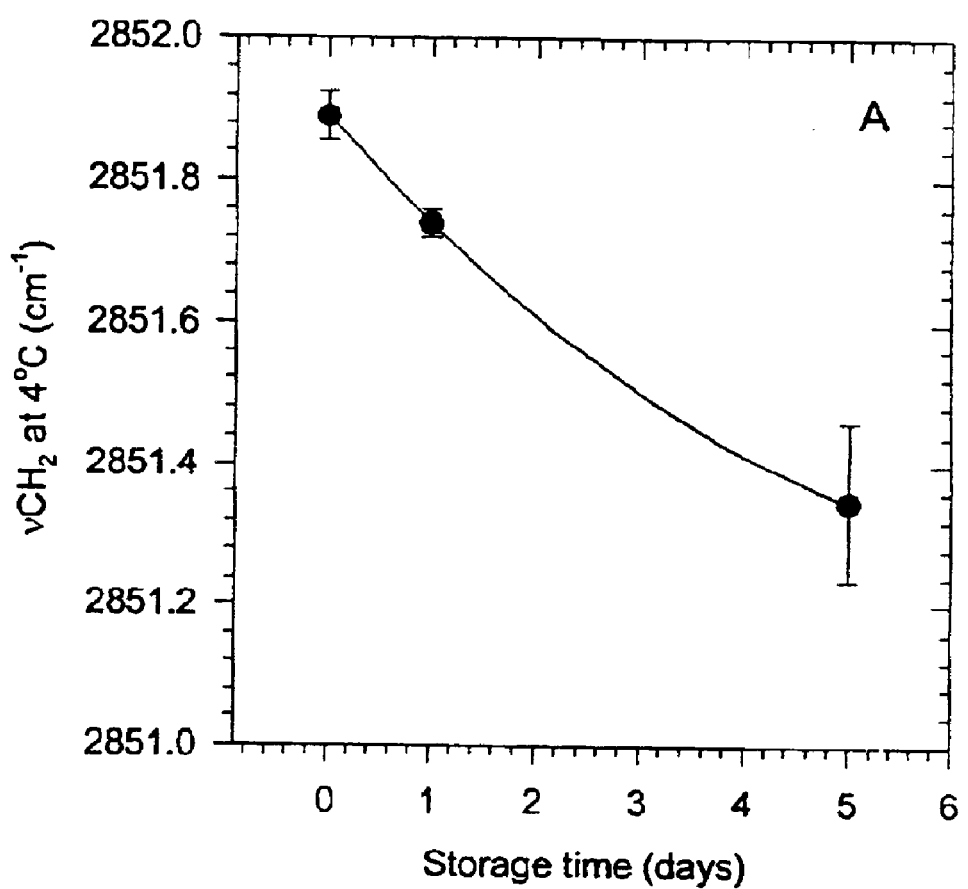
FIG. 37 is a graph illustrating the effect (e.g., storage time) of cold storage on erythrocyte membranes versus the wavenumber of the lipid $CH_2$ stretch vibration at 4° C. during storage at 4° C.
Figure 38:
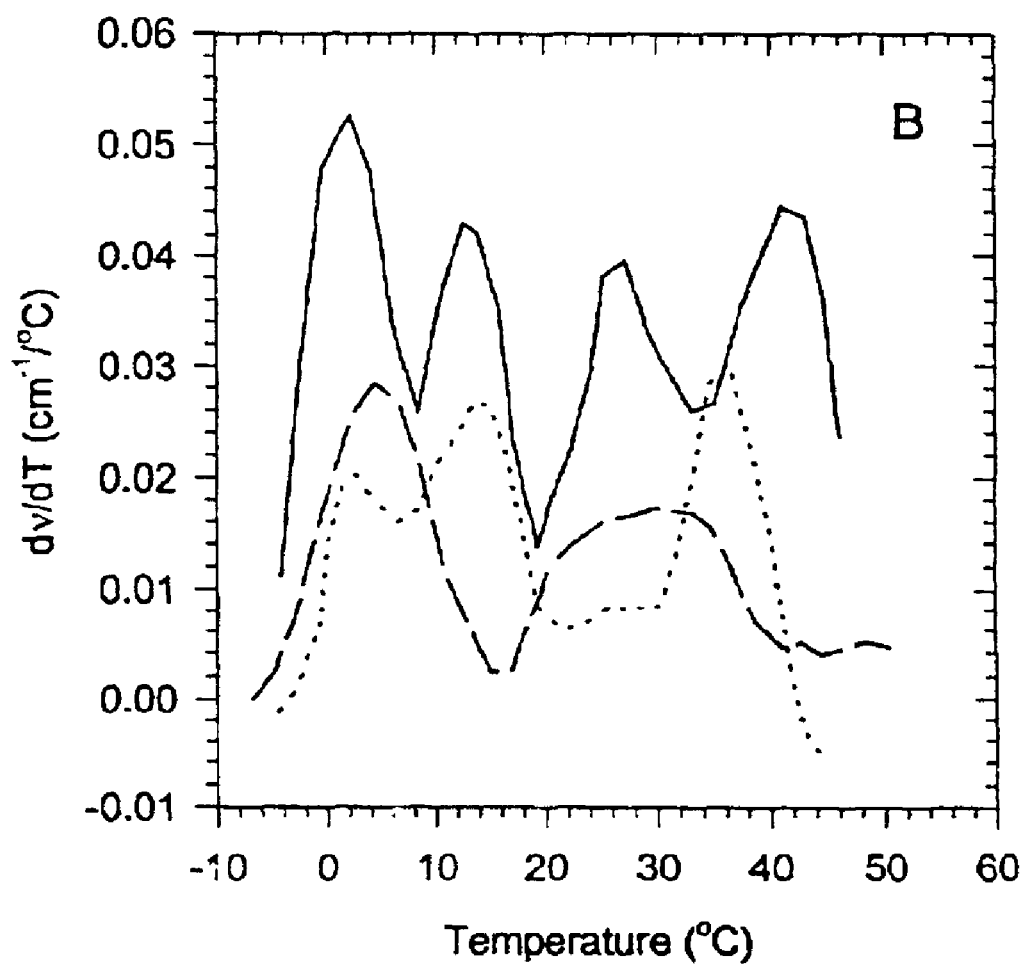
FIG. 38 is a graph illustrating wavenumber versus temperature plots immediately after isolation (dotted line), after 1 day storage (broken line), and after 5 days storage (solid line) at 4° C.

Effect of Storage on Thermotropic Response. Erythrocytes were stored in autologous acid citrate dextrose (ACD) anticoagulated platelet poor plasma at 4° C. Aliquots of the cells were washed three times in cold PBS buffer, and the effect of cold storage on the membrane fluidity was studied, using FTIR. The wavenumber of the lipid band at 4° C. dropped significantly after 5 days of cold storage, as best shown in FIG. 37, suggesting a rigidification of the membrane. In addition, the thermotropic response of the cells also changed during cold storage (see FIG. 38). After one day, the two main transitions shifted to lower temperatures, and after five days storage, multiple sharp phase transitions were observed, indicating a large scale rearrangement of the membrane lipids.

Figure 39:
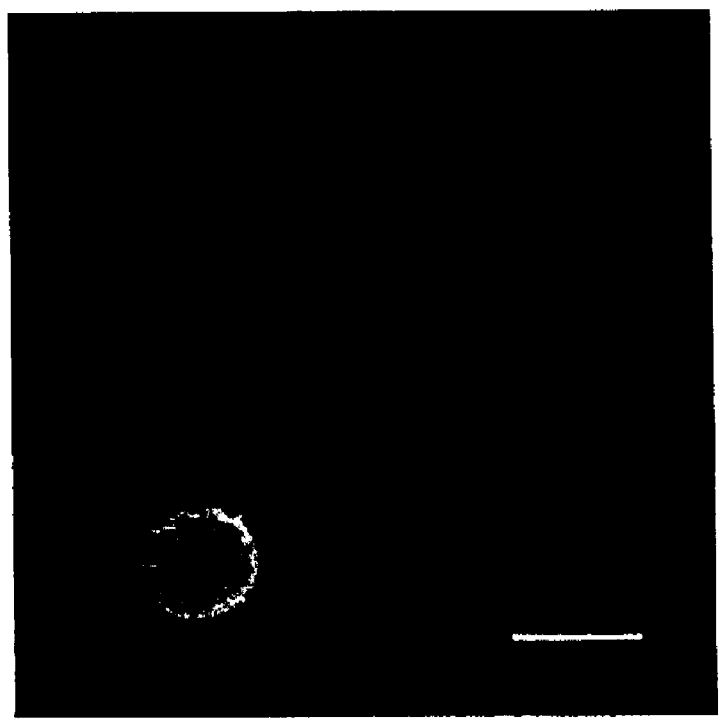
FIG. 39 is an enlarged view of dil-$C_{18}$ labeled erythrocytes distribution after 4 days storage at 4° C., illustrating that the dye remained homogeneously distributed in erythrocyte membranes during cold storage.

Formation of Lipid Domains. Lipid dye dil-$C_{18}$ was used to study if regrouping of lipids during cold storage as suggested by the FTIR experiments, was accompanied by formation large membrane domains or aggregates. Dil-$C_{18}$ preferentially partitions into ordered lipid domains and can be used to investigate lipid phase separation in living cells. FIG. 39 depicts an image of dil-$C_{18}$ labeled erythrocytes after 4 days exposure to 4° C. The dye remained uniformly distributed during cold storage (only the results after 4 days are shown) which suggests that the lipid domains in the membrane are below the resolution limit of the microscope.

Chances in Lipid Compositions. The composition of diacyl phosholipids and the amount of cholesterol in the total lipid extract of human erythrocytes is presented in the following Table IV:

TABLE IV

| Storage Time | FFA | Chol. | PE | PS | PC | SM |
| --- | --- | --- | --- | --- | --- | --- |
| Fresh | | 48.1 ± 2.2 | 6.2 ± 2.7 | 2.6 ± 0.2 | 24.2 ± 0.4 | 18.9 ± 0.3 |
| 1 day storage | 5.0 ± 0.5 | 36.7 ± 0.1 | 7.2 ± 0.2 | 5.1 ± 0.2 | 25.8 ± 0.0 | 20.2 ± 0.0 |
| 5 days storage | 2.4 ± 0.2 | 43.6 ± 1.3 | 6.4 ± 0.2 | 4.2 ± 0.2 | 24.2 ± 0.5 | 18.8 ± 0.3 |

The foregoing Table IV more specifically presents lipid composition of human erythrocytes, with the values representing the mean of two samples express as weight percent of the total lipids and with the abbreviations having the following meaning: Chol, cholesterol; FFA, free fatty acids; PE, phosphatidylethanolamine; PS, phosphatidylserine; PC, phosphatidylcholine; SM, shingomyelin. As shown in Table IV, phosphatidylcholine is the most abundant lipid (24 wt. %). The amounts of PE and PS are 6 and 3 wt. % respectively. Sphingolipids make up 19 wt. % of the lipid composition. The cholesterol content was found to be approximately 50 wt. % in fresh erythrocytes. Even after one day storage, free fatty acids were detected in the erythrocyte membrane, indicating chemical changes in the membrane composition. In addition, the lipid analysis revealed that the amount of cholesterol decreased during in vitro storage at 4° C. The relative amounts of the phospholipids did not change significantly during storage.

Overall Protein Secondary Structure. The overall protein secondary structure of erythrocytes during cold storage was monitored using the IR amide-II band. FTIR measures an average signal of all cellular proteins, but in erythrocytes the amide-II band is dominated by the hemoglobin. The shape of the amide-II band with a major band at 1550 cm$^{-1}$, and only minor contributions of bands at 1535 cm$^{-1}$ and 1565 cm$^{-1}$ suggests a high relative proportion of α-helical content of hemoglobin. No changes in amide-II band profile were observed after 9 days of storage at 4° C.

Discussion

Physical properties of membranes from human erythrocytes were evaluated using FTIR, and it has been demonstrated that substantial changes in the membrane physical properties and lipid composition occur during cold storage. In contrast, the average protein secondary structure of erythrocyte hemoglobin was not affected by cold storage.

The human erythrocyte was the first cell in which it was shown that phospholpipids are organized in domains within the membrane rather than being homogeneuosly distributed. The asymetric distribution with predominantly PS and PE in the inner leaflet and, PC and SM in the outer leaflet was demonstrated using specific phospholipida in the erythrocyte membrane with a more rigid outer leaflet and a more fluid inner leaflet.

Cholesterol modulates lipid intermixing in lipid bilayers: phospholipids which are strongly phase separated in the absence of cholesterol become homogeneously mixed at high (e.g., 50 mol %) cholesterol contents. Therefore, the observation of multiple transitions in erythrocytes is unexpected. However, the specific mixture of sphingolipids and phospholipids in the erythrocyte membrane may explain why multiple phase transitions can be observed at such high cholesterol contents. Mixtures of phospholipids and glycosphingolipids exhibit significant inhomogeneity in lipid mixing even at high (50%) bilayer cholesterol contents.

Cholesterol depletion confirmed that the small inflections that were observed in the thermal profiles of intact cells correspond to real thermal events in the membrane. Three major cooperative transitions became visible in the wavenumber versus temperature plot after cholesterol depletion of erythrocyte membranes.

It is suggested that the transition at 34° C. observed both in intact and in cholesterol depleted cells reflects the melting of the more rigid sphingolipid rich outer leaflet of the membrane because sphingolipids generally exhibit relatively high melting points, ranging from about 25° C. to 45° C. Sheep erythrocyte membranes exhibit a sphinglipid transition between 26° C. and 35° C. It is suggested that the transition at 15° C. reflects the melting of the more fluid inner membrane leaflet. The phase transitions of red cells which were observed are very similar to those of human platelets, which have two transitions at around 15° C. and 30° C.

The transition at 26° C. in the cholesterol depleted cells was most likely masked by the cholesterol in the intact cells, or alternatively, it may reflect a mixed phase due to regrouping of the membrane lipids between the inner and outer membrane leaflet. The data support the concept that cholesterol modulates the membrane fluidity by decreasing the lipid order at low temperatures and by increasing the lipid order at high temperatures.

Thus, the FTIR studies reveal that red blood cells and platelets have similar phase transitions and in both cell types phase separation was observed upon long-term exposure to cold temperatures. But in contrast to platelets, no large membrane aggregates were formed in the erythrocyte membrane during cold storage. It is suggested that the low level of aggregation of microdomains in red blood cells may be responsible for their relative insensitivity to chilling damage. That property could result from the high proportion of cholesterol in red blood cell membranes compared with that seen in platelets.

EXAMPLE 12

Isolation of Erythrocytes, Cholesterol, Depletion, Preparation of Ghosts, and Storage Conditions: Venous blood was collected from healthy adults, with informed consent, according to institutional protocols. Blood was anticoagulated with ACD (citric acid, citrate, dextrose). Whole blood was centrifuged at 320 x g for 8 minutes. Platelets were isolated from the platelet rich plasma and used for other experiments. Platelet poor plasma was added back to the erythrocytes and the mixture was stored at 4° C.

Cells were incubated at 37° C. for one hour in the presence of 10 mM methyl-β-cyclodextrin (MβCD) in order to remove cholesterol from the plasma membranes. Erythrocyte ghosts were prepared. ACD anticoagulated blood was stored in 15 ml polypropylene Falcon tubes at 4° C. Aliquots were taken, and the cells were washed at least three times in cold PBS buffer (100 mM NaCl, 9.4 mM Na$_2$HPO$_4$, 0.6 mM KH$_2$PO$_4$, pH 7.4), prior to further analyses.

Lipid Extraction, Separation and Analysis. Erythrocyte lipids were extracted in methanol/chloroform (1:2, v/v), and incubated on ice for 1 hour. The lipid composition of erythrocytes was analyzed by rod-typed analytical thin layer chromatography using a Latroscan TH-10 from (Lantron Laboratories of Tokyo, Japan). The traces were analyzed using Sigmaplot from Jandel Scientific of San Rafael, Calif. The individual lipids were expressed as weight percent of the total lipids.

FTIR Spectroscopy and Sample Preparation. Infrared spectra were recorded on a Perkin-Elmer 2000 Fourier transform IR-spectrometer as described previously. Red cell pellets were spread between two $CaF_2$ infrared windows in a temperature-controlled cell. Intact cells were cooled to $-5°$ C., kept at this temperature for 15 minutes, and then rewarmed to determine the phase transitions. Forty to 50 spectra were recorded over a temperature range from $-5°$ C. to $+45°$ C., at a heating rate of $5°$ C./min. Four scans were accumulated for each spectrum between 3600–900 $cm^{-1}$ at 4 $cm^{-1}$ resolution.

Data processing consisted of taking the second derivative of the IR-absorbance spectra using a 9 point smoothing favor. Inverted second derivative spectra were normalized on the lipid bamd arpimd 2850 $cm^{-1}$. Band positions were determined as described previously. The wavenumber ($cm^-$1) of the $CH_2$ symmetric stretching vibration was plotted as a function of temperature. The first derivative of the wavenumber versus temperature plots was obtained using Peakfit from Jandel Scientific, San Rafael, Calif. to show inflections more clearly and as a measure of the co-operativity of the transitions. Phase transition temperatures and co-operativity values were determined from the maxima in the first derivative plots. For the protein studies, the spectral region between 1600 and 1500 $cm^{-1}$ selected. This region contains the amide-II absorption band of the protein backbones.

Fluorescence Microscopy. Washed erythrocytes were diluted to a final concentration of $1\times10^8$ cells/ml. They were labeled with dil-$C_{18}$ from Molecular Probes, Inc. of Eugene, Oreg. (2.5 µg/ml) for 60 minutes in the dark at $37°$ C. Aliquots were incubated at $37°$ C. or stored at $4°$ C. The labeled erythrocytes were then fixed with 1% paraformaldehyde for two hours at the corresponding temperatures. The cells were placed on microscope slides and examined with a Zeiss ICM405 inverted microscope (Planachromat 100x/ 1.4 n.a.objective) and photographed with Ektachrome 400 film from Kodak, Rochester, N.Y.

Conclusion

Embodiments of the present invention provide that trehalose, a sugar found at high concentrations in organisms that normally survive dehydration, can be used to preserve biological structures in the dry state. Human blood platelets can be loaded with trehalose under specified conditions, and the loaded cells can be freeze dried with excellent recovery. Additional embodiments of the present invention provide that trehalose may be used to preserve nucleated (eukaryotic) cells.

Eukaryotic cells lines, such as human mesenchymal stem cells and a epithelial 293H cells, have two membrane phase transitions at approximately $15°$ C. and $35°$ C. Further, they are able to take up solutes from an extracellular medium, as indicated by their loading with the fluorescent dye Lucifer yellow CH. This technique may be employed to load cells with an oligosaccharide, preferably trehalose. Trehalose does not interfere with the growth and viability of cells for up to three days. Cells loaded with trehalose and freeze-dried were viable immediately following rehydration and were healthy in that the membranes appeared intact and the nuclei were clearly visible and were of normal morphology. Some cells even attached weakly to the substrate and appeared in relatively good physical shape even after 5 days post-rehydration.

Alcohol-reduced erthrocytes have three membrane phase transitions at approximately $15°$ C., $26°$ C. and $35°$ C. Alcohol (e.g. cholesterol) depletion of erthrocytes resulted in a large increase in the cooperativity of the membrane phase transitions. Any of the membrane phase transitions, especially the phase transitions at around $35°$ C., may be used to load erthrocytes with a protectant (e.g. an oligosaccharide such as trehalose). Alcohol-reduced erthrocytes loaded with a protectant and freeze-dried were viable immediately following rehydration.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope and spirit of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the appended claims.

What is claimed is:

1. A process for loading an oligosaccharide into an erythrocytic cell comprising:

providing an erythrocytic cell having cholesterol;

removing at least a portion of the cholesterol from the erythrocytic cell to produce an erythrocytic cell having a phase transition when the produced erythrocytic cell has a temperature within a temperature range selected from a group of temperature ranges consisting of a low phase-transition temperature range, an intermediate phase-transition temperature range, and a high phase-transition temperature range; and disposing the produced erythrocytic cell in an oligosaccharide solution for loading an oligosaccharide into the erythrocytic cell in vitro.

2. The process of claim 1 wherein said oligosaccharide solution includes said temperature range.

3. The process of claim 1 additionally comprising increasing the loading efficiency of the oligosaccharide into the erythrocytic cell by heating the oligosaccharide solution.

4. The process of claim 1 wherein said low phase-transition temperature range ranges from a temperature greater than about $2°$ C. to a temperature equal to or less than about $20°$ C.

5. The process of claim 1 wherein said intermediate phase-transition temperature range ranges from a temperature greater than about $20°$ C. to a temperature equal to or less than about $30°$ C.

6. The process of claim 1 wherein said high phase-transition temperature range ranges from a temperature greater than about $30°$ C. to a temperature equal to or less than about $50°$ C.

7. The process of claim 6 wherein said high phase transition temperature range ranges from about $30°$ C. to about $40°$ C.

8. The process of claim 6 wherein said high phase transition temperature range ranges from about $32°$ C. to about $38°$ C.

9. The process of claim 1 wherein said oligosaccharide comprises trehalose.

10. The process of claim 1 wherein said loading of the oligosaccharide comprises loading by fluid phase endocytosis.

11. The process of claim 1 wherein said removing at least a portion of the cholesterol comprises removing at least about 10% by wt. of the cholesterol.

12. The process of claim 1 wherein said removing at least a portion of the cholesterol comprises removing at least about 30% by wt. of the cholesterol.

13. The process of claim 1 wherein said produced erythrocytic cell comprises from about 20% by wt. to about 40% by wt. of the cholesterol.

14. The process of claim 1 wherein said produced erythrocytic cell comprises from about 20% by wt. to about 30% by wt. of the cholesterol.

15. An erythrocytic cell produced in accordance with the process of claim 1.

* * * * *